(12) United States Patent
Zender et al.

(10) Patent No.: US 8,137,907 B2
(45) Date of Patent: Mar. 20, 2012

(54) ORTHOTOPIC AND GENETICALLY TRACTABLE NON-HUMAN ANIMAL MODEL FOR LIVER CANCER AND THE USES THEREOF

(75) Inventors: Lars Zender, Hannover (DE); Scott W. Lowe, Cold Spring Harbor, NY (US); Mona S. Spector, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 305 days.

(21) Appl. No.: 12/072,115

(22) Filed: Feb. 21, 2008

(65) Prior Publication Data

US 2009/0029872 A1 Jan. 29, 2009

Related U.S. Application Data

(63) Continuation-in-part of application No. 11/325,218, filed on Jan. 3, 2006, now abandoned.

(60) Provisional application No. 60/641,043, filed on Jan. 3, 2005, provisional application No. 60/686,609, filed on Jun. 1, 2005.

(51) Int. Cl.
C12Q 1/68 (2006.01)
C07H 21/04 (2006.01)
C07K 16/00 (2006.01)
C12P 19/34 (2006.01)

(52) U.S. Cl. ..... 435/6; 536/23.1; 536/24.31; 536/24.33; 530/387.1; 435/91.2

(58) Field of Classification Search .................. None
See application file for complete search history.

(56) References Cited

U.S. PATENT DOCUMENTS

| | | | |
|---|---|---|---|
| 5,075,109 A | 12/1991 | Tice et al. | |
| 5,530,101 A | 6/1996 | Queen et al. | |
| 5,593,676 A | 1/1997 | Bhat et al. | |
| 5,672,485 A | 9/1997 | Foster et al. | |
| 5,686,072 A | 11/1997 | Uhr et al. | |
| 5,928,638 A | 7/1999 | Uchida et al. | |
| 6,111,093 A | 8/2000 | Seed et al. | |
| 6,134,982 A | 10/2000 | Takabatake et al. | |
| 6,165,737 A | 12/2000 | Wang et al. | |
| 6,306,393 B1 | 10/2001 | Goldenberg | |
| 6,583,333 B1 | 6/2003 | Lowe et al. | |
| 2002/0041847 A1 | 4/2002 | Goldenberg | |
| 2002/0086356 A1 | 7/2002 | Tuschl et al. | |
| 2002/0132346 A1 | 9/2002 | Cibelli | |
| 2002/0155604 A1 | 10/2002 | Ledbetter et al. | |
| 2003/0148409 A1 | 8/2003 | Rossi et al. | |
| 2003/0165954 A1 | 9/2003 | Katagiri et al. | |
| 2003/0226159 A1 | 12/2003 | Bachoo et al. | |
| 2004/0006035 A1 | 1/2004 | Macejak et al. | |
| 2004/0029114 A1* | 2/2004 | Mack et al. .................. 435/6 |
| 2004/0039010 A1 | 2/2004 | Grupp et al. | |
| 2004/0045043 A1 | 3/2004 | Finney et al. | |
| 2004/0053411 A1 | 3/2004 | Cullen et al. | |
| 2004/0053869 A1 | 3/2004 | Andrews et al. | |
| 2004/0202658 A1 | 10/2004 | Benyunes | |
| 2005/0003541 A1 | 1/2005 | Katsuki et al. | |
| 2005/0070693 A1 | 3/2005 | Hansen et al. | |
| 2005/0075492 A1 | 4/2005 | Chen et al. | |
| 2005/0143448 A1 | 6/2005 | Grenard et al. | |
| 2005/0191302 A1 | 9/2005 | Arthur et al. | |
| 2005/0233391 A1 | 10/2005 | Spies et al. | |
| 2006/0040391 A1 | 2/2006 | Bailey et al. | |
| 2006/0123494 A1 | 6/2006 | Wu et al. | |
| 2006/0135456 A1 | 6/2006 | Hannon et al. | |
| 2006/0162000 A1 | 7/2006 | Zender et al. | |
| 2006/0240556 A1 | 10/2006 | Cibelli | |
| 2006/0247193 A1 | 11/2006 | Taira et al. | |
| 2006/0286584 A1 | 12/2006 | Duojia | |
| 2006/0294604 A1 | 12/2006 | Fridman et al. | |
| 2007/0033663 A1 | 2/2007 | Katsuki et al. | |
| 2007/0044164 A1 | 2/2007 | Dickins et al. | |
| 2007/0078084 A1 | 4/2007 | Kishore et al. | |
| 2007/0178106 A1 | 8/2007 | Romagne | |
| 2008/0025958 A1 | 1/2008 | Hannon et al. | |

(Continued)

FOREIGN PATENT DOCUMENTS

EP 1092783 4/2001

(Continued)

OTHER PUBLICATIONS

Agrawal et al., "Antisense therapeutics: is it as simple as complementary base recognition?," Mol Med Today. Feb. 2000;6(2):72-81.
Alison & Lovell, "Liver cancer: the role of stem cells." Cell Prolif. vol. 38, pp. 407-421 (2005).
Aoki, et al., "The Akt kinase: Molecular determinants of oncogenicity." Proc. Natl. Acad. Csi.; vol. 95, pp. 14950-14955 (1998).
Bernards et al., "ShRNA libraries and their use in cancer genetics," Nature Methods vol. 3, pp. 701-706 (2006).
Blum, "Molecular therapy and prevention of hepatocellurial carcinoma," Hepatobiliary and pancreatic diseases International, vol. 2, pp. 11-22 (Feb. 1, 2002).
Blum, "Treatment of Hepatocellular carcinoma," Bailliere's Best Partice and reasearch clinical gastroenterology, Bailliere Tindall, London, US, vol. 19, pp. 129-145 (2005).

(Continued)

Primary Examiner — Amy Bowman
(74) Attorney, Agent, or Firm — Wilmer Cutler Pickering Hale and Dorr LLP

(57) ABSTRACT

This invention provides a genetically tractable in situ non-human animal model for hepatocellular carcinoma. The model is useful, inter alia, in understanding the molecular mechanisms of liver cancer, in understanding the genetic alterations that lead to chemoresistance or poor prognosis, and in identifying and evaluating new therapies against hepatocellular carcinomas. The liver cancer model of this invention is made by altering hepatocytes to increase oncogene expression, to reduce tumor suppressor gene expression or both and by transplanting the resulting hepatocytes into a recipient non-human animal.

This invention also relates to the use of RNA interference (RNAi) technology in vivo to efficiently identify genes associated with liver cancer, in particular those encoding tumor suppressors, by knocking out candidate genes using RNAi and observing whether tumors would develop.

18 Claims, 39 Drawing Sheets

U.S. PATENT DOCUMENTS

| | | | |
|---|---|---|---|
| 2008/0221056 A1* | 9/2008 | Baylin et al. | 514/44 |
| 2008/0226553 A1 | 9/2008 | Lowe et al. | |
| 2008/0242622 A1 | 10/2008 | Lowe et al. | |
| 2009/0022685 A1 | 1/2009 | Lowe et al. | |
| 2009/0082298 A1 | 3/2009 | Dickins et al. | |
| 2009/0186839 A1 | 7/2009 | Lowe et al. | |
| 2009/0217404 A1 | 8/2009 | Lowe et al. | |
| 2010/0186097 A1 | 7/2010 | Lowe et al. | |
| 2010/0273660 A1 | 10/2010 | Zender et al. | |
| 2010/0297010 A1 | 11/2010 | Bric et al. | |
| 2010/0310504 A1 | 12/2010 | Lowe et al. | |
| 2011/0015093 A1 | 1/2011 | Fellmann et al. | |
| 2011/0035814 A1 | 2/2011 | Zender et al. | |

FOREIGN PATENT DOCUMENTS

| | | |
|---|---|---|
| EP | 1247865 | 6/2005 |
| WO | WO-91/13974 | 9/1991 |
| WO | WO-94/09363 | 4/1994 |
| WO | WO-95/03770 | 2/1995 |
| WO | WO-96/36360 | 11/1996 |
| WO | WO-99/32619 | 7/1999 |
| WO | WO-99/55886 | 11/1999 |
| WO | WO-00/20025 | 4/2000 |
| WO | WO-00/67796 | 11/2000 |
| WO | WO-01/13945 | 3/2001 |
| WO | WO-01/36646 | 5/2001 |
| WO | WO-01/68836 | 9/2001 |
| WO | WO-02/16620 | 2/2002 |
| WO | WO-02/50118 | 6/2002 |
| WO | WO-02/072762 | 9/2002 |
| WO | WO-03/042382 | 5/2003 |
| WO | WO-03/093441 | 11/2003 |
| WO | WO-2004/022722 | 3/2004 |
| WO | WO-2004/029219 | 4/2004 |
| WO | WO-2004/035782 | 4/2004 |
| WO | WO-2004/074445 | 9/2004 |
| WO | WO-2005/012493 | 2/2005 |
| WO | WO-2005/013886 | 2/2005 |
| WO | WO-2005/017148 | 2/2005 |
| WO | WO-2005/020969 | 3/2005 |
| WO | WO-2006/023848 | 3/2006 |
| WO | WO-2006/074186 | 7/2006 |
| WO | WO-2007/053184 | 5/2007 |
| WO | WO-2007/139985 | 12/2007 |
| WO | WO-2008/021393 | 2/2008 |
| WO | WO-2008/115556 | 9/2008 |
| WO | WO-2008/124133 | 10/2008 |
| WO | WO-2008/143979 | 11/2008 |
| WO | WO-2009/042798 | 4/2009 |
| WO | WO-2009/055724 | 4/2009 |

OTHER PUBLICATIONS

Brummelkamp et al., "A system for stable Expression of Short Interfering RNAs in mammalian Cells," Science, vol. 296, pp. 550-553 (2002).

Chang et al., "Lessons from Nature: MicroRNA-based ShRNA Libraries," Nature Methods, vol. 3, pp. 707-714 (2006).

Chen et al., "Co-expression and regulation of Met and Ron proto-oncogenes in human hepatocellular carnicoma tissues and cell lines," Hepatology, vol. 26, pp. 59-66 (1997).

Comerford et al., "Induction of Hepatocyte proliferation and death by modulation of T-antigen expression," Oncogene, vol. 22, pp. 2515-2530 (2002).

Datta, et al., "Cellular survival: a play in three akts" *Genes Dev.* 13, (1999) pp. 2905-2927.

De Benedetti et al., "eIF-4E expression and its role in malignancies and metastases," Oncogene 23: 3189-3199 (2004).

Di Cristofano et al., "Pten and p27KIPI cooperate in prostate cancer tumor suppression in the mouse," Nature Genetics, vol. 27, pp. 222-224 (2001).

Di Cristofano, et al., "Pten is essential for embryonic development and tumor suppression" *Nature Genetics*, 19, (1998) pp. 348-355.

Dickins et al., "Probing Tumor Phenotypes Using Stable and Regulated Synthetic MicroRNA Precursors," Nature Genetics, 37(11):1289-1295 (2005).

Duckett et al., "A conserved family of cellular genes related to the baculovirus iap gene and encoding apoptosis inhibitors," EMBO J., vol. 15, pp. 2685-2694 (1996).

Elbashir et al., "Analysis of gene function in somatic mammalian cells using small interfering RNAs," Methods , vol. 26, pp. 199-213 (2002).

Fewell et al., "Vector-based RNAi approaches for stable—inducible and genome—wide screens," 2006, Drug Discovery Today 11: 975-982.

Final Office action mailed on Apr. 17, 2007, for U.S. Appl. No. 11/325,218, filed Jan. 3, 2006.

Final Office action mailed on Aug. 18, 2008, for U.S. Appl. No. 11/325,218, filed Jan. 3, 2006.

Final Office action mailed on Aug. 23 2010, for U.S. Appl. No. 10/546,055, filed Aug. 23, 2006.

Final Office action mailed on Jan. 24, 2011, for U.S. Appl. No. 11/893,540, filed Aug. 15, 2007.

Final Office Action mailed on Jan. 6, 2009, for U.S. Appl. No. 11/603,509, filed Nov. 21, 2006.

Final Office Action mailed on May 14, 2010, for U.S. Appl. No. 12/156,957, filed Jun. 5, 2008.

Office Action mailed on Sep. 25, 2007, for U.S. Appl. No. 11/603,509, filed Nov. 21, 2006.

Glinsky,G.V., et al. (2005). Microarray analysis identifies a death from-cancer signature predicting therapy failure in patients with multiple types of cancer. J. Clin. Invest 115,1503-1521.

Guo et al., "Liver repopulation after cell transplantation in mice treated with retrosine and carbon tetrachloride." Transplantation vol. 73, pp. 1818-1824 (2002).

Gupta et al., "Hepatocyte transplantation: emerging insights into mechanisms of liver repopulation and their relevance to potential therapies," Journal of Hepatology, vol. 30, pp. 162-170 (Jan. 1999).

Hanahan, et al., "The hallmarks of cancer," *Cell*, 100 (2000) pp. 57-70.

Hannon, G. J. (2002) RNA interference Nature 418, 244-251.

Hemann et al., "An epi-allelic series of P53 hypomorphs created by stable RNAI produces distinct tumor phenotypes in vivo," Nature Genetics, vol. 33, pp. 396-400 (2003).

Hu et al., "Association of Vimentin overexpression and hepatocellular carcinoma metastasis," Oncogene 23, 298-302 (2004).

Huang, et al., "Targeting mTOR signaling for cancer therapy" *Curr Opin. Pharmacol.*, 3, (2003) pp. 371-377.

Hutvagner et al., "A cellular function for the RNA-Interference Enzyme Dicer in the maturation of the let-7 small temporal RNA," Science, vol. 293, pp. 834-838 (2001).

Hyun, et al., "Loss of PTEN expression leading to high Akt activation in human multiple myelomas" *Blood*, 96, (2000) pp. 3560-3568.

International Search Report mailed on May 16, 2007, for International Patent Application no. PCT/US06/00119 filed Jan. 3, 2006.

Jacobs,J.J., et al.,(1999). Bmi-1 collaborates with c-Myc in tumorigenesis by inhibiting c-Myc-induced apoptosis via INK4a/ARF. Genes Dev. 13,2678-2690.

Johnstone, et al., "Apoptosis: A link between cancer genetics and chemotherapy" *Cell* 108 (2002) pp. 153-164.

Jung et al., "Adenovirus-medited transfer of siRNA against PTTG1 inhibits liver cancer cell growth in vitro and in vivo," Hepatology; vol. 43, pp. 1042-52 (2006).

Lee et al., Maternal or paternal exposure to radiation increases susceptibility to the induction of glutathione S-transferasepositive hepatic foci in offspring rats. Cancer Lett. Oct. 23, 1998;132(1-2):31-6.

Lee et al., "MicroRNA maturation:Stepwise processing and subcellular localization," The EMBO Journal, vol. 21, pp. 4663-4670 (2002).

Liston et al., "The inhibitors of apoptosis: there is more to life than Bcl2," Oncogene 22, pp. 8568-8580 (2003).

Llovet etal. "Hepatocellular carcinoma." Lancet, vol. 362, pp. 1907-1917 (2003).

Lu et al., "In vivo Application of RNA interferences: From Functional Genomics to Therapeutics," 2005, Advances in Genetics 54: 117-142.

Lucito et al., "Representational oligonucleotide microarray analysis: a high-resolution method to detect genome copy number variation." Genome Res. vol. 13, pp. 2291-2305 (2003).

Mayo et al., "PTEN protects p53 from Mdm2 and sensitizes cancer cells to chemotherapy," J. Cell Biol. vol. 277, pp. 5484-5489 (2002).

McCurrach, et al., "bax-deficiency promotes drug resistance and oncogenic transformation by attenuating p53-dependent apoptosis" *Proc. Natl. Acad. Sci. USA*, 94 (1997) pp. 2345-2349.

McManus et al., Gene silencing in mammals by small interfering RNAs, Nature Reviews, vol. 3, pp. 737-747 (2002).

Ngo, V.N., et al., (2006). A loss-of-function RNA interference screen for molecular targets in cancer. Nature 441, 106-110.

Nitou et al., "Purification of fetal mouse hepatoblasts by magnetic beads coated with monoclonal anti-e-cadherin antibodies and their in vitro culture." Exp. Cel Res. vol. 279, pp. 330-343 (2002).

Non Final Office Action mailed on Aug. 9, 2010, for U.S. Appl. No. 12/156,957, filed Jun. 5, 2008.

Non Final Office action mailed on Dec. 11, 2009, for U.S. Appl. No. 10/546,055, filed Aug. 23, 2006.

Non Final Office Action mailed on Dec. 7, 2007, for U.S. Appl. No. 11/444,107, filed May 31, 2006.

Non Final Office action mailed on Jul. 1, 2010, for U.S. Appl. No. 11/893,540, filed Aug. 15, 2007.

Non Final Office action mailed on Jul. 14, 2006 for U.S. Appl. No. 11/325,218, filed Jan. 3, 2006.

Non Final Office Action mailed on Jul. 14, 2009, for U.S. Appl. No. 12/077,737, filed Mar. 19, 2008.

Non Final Office Action mailed on May 24, 2010 for U.S. Appl. No. 12/072,124, filed Feb. 23, 2008.

Non Final Office Action mailed on Oct. 1, 2010, for U.S. Appl. No. 12/497,967, filed Jul. 6, 2009.

Non Final Office Action mailed on Sep. 3, 2009, for U.S. Appl. No. 12/156,957, filed Jun. 5, 2008.

Pang, E., et al., (2005). Karyotypic imbalances and differential gene expressions in the acquired doxorubicin resistance of hepatocellular carcinoma cells. Lab Invest 85, 664-674.

Parkin et al. "Estimating the world cancer burden: Globocan 2000." Int. J. Cancer vol. 94, pp. 153-156 (2001).

Peng et al., "Amplification of the c-myc gene in human hepatocellular carcinoma: biological significance," J. Formos. Med Assoc. 92, 866-870 (1993).

Roymans, et al., "Phosphatidylinositol 3-kinases in tumor progression" *Eur J Biochem*, 268, (2001) pp. 487-498.

Sakai, et al., "PTEN gene alterations in lymphoid neoplasms," *Blood*, 92, (1998) pp. 3410-3415.

Sandgren et al., "Oncogene-induced liver neoplasia in transgenic mice." Oncogene, vol. 4 pp. 715-724. (1989).

Scherer and Rossi, Approaches for the sequence-specific knockdown of mRNA, Nature Biotechnology vol. 21 pp. 1457-1465 (2003).

Schmelzle, et al., "TOR, a central controller of cell growth," *Cell.*, 103, (2000) pp. 253-262.

Schmidt, et al., "Dissecting p53 tumor suppressor functions in vivo," Cancer Cell, vol. 1, pp. 289-298 (2002).

Sebat et al., "Large-scale copy number polymorphism in the human genome." Science vol. 305, pp. 525-528 (2004).

Serrano, et al., "Role of the INK4a locus in tumor suppression and cell mortality" *Cell*, 85 (1997) pp. 27-37.

She et al., "Resistance to Gefitinib in PTEN-Null HER-Overexpressing tumor Cells can be overcome through restoration of PTEN Fuction or Pharmacologic Modulation of Constitutive Phosphatidylinositol 3'-kinase/Akt pathway signaling," Clinical Cancer Research, vol. 9, 4340-4346 (Oct. 2003).

Sherr Charles, "The INKaI ARF Network in Tumor Suppression," Molecular Cell Biology, pp. 731-737 (2001).

Silva et al., "Second-generation ShRNA libraries covering to mouse and human genomes," Nature genetics, vol. 37, pp. 1281-88 (2005).

Steck, et al., "identification of a candidate tumor suppressor gene, MMAC1, at chromosome 10q23.3 that is mutated in multiple advanced cancers" *Nat. Genet.*, 15 (1997) pp. 356-362.

Supplementary European Search report mailed on Dec. 20, 2010 for European Application No. 06717340 filed Jan. 3, 2006.

Suzuki, "High cancer susceptibility and embryonic lethality associated with mutation of the PTEN tumor suppressor gene in mice" *Current Biology*, 8 (1998) pp. 1169-1178.

Thompson and Lyons, "Recent progress in targeting the Raf/MEK/ERK pathway with inhibitors in cancer drug discovery," Current Opinion in Pharmacology 5: 350-356 (2005).

Valencia-Sanchez et al., "Control of translation and mRNA degradation by miRNAs and siRNAs," Genes Dev., vol. 20, pp. 515-524 (2006).

Vivanco, et al., "The Phosphatidylinositol 3-Kinase Akt pathway in human cancer" *Nat. Rev. Cancer*, 2, (2002) pp. 489-501.

Wang et al., "Activation of the Met receptor by cell attachment induces and sustains hepatocellular carcinomas in transgenic mice.", J. Cell Biol. vol. 153 pp. 1023-1034 (2001).

Witt, A. et al. (2006) Functional Proteomics Approach to Investigate the Biological Activities of cDNAs Implicated in Breast Cancer. Journal of Proteome Research 5, 599-610.

Wright and Duckett "Reawakening the cellular death program in neoplasia through the therapeutic blockade of IAP function." J. Clin. Invest. vol. 115, pp. 2673-2678 (2005).

Yang, et al., "The transformation suppressor Pdcd4 is a novel eukaryotic translation initiation factor 4A binding protein that inhitibs translation" *Mol Cell Biol.*, 23, (2003) pp. 26-37.

Zender et al., "Cancer gene discovery in hepatocellular carcinoma," Journal of Hepatology, vol. 52, pp. 921-929 (Jun. 2010).

Zender et al., "Identification and validation of oncogenes in liver cancer using an integrative oncogenomic approach," Cell, vol. 125, pp. 1253-1267 (Jun. 2006).

Zender et al., "Representational oligonucleotide microarray (ROMA) identifies cIAP1/cIAP2 as candidate oncogenese in mouse and Human Hepatocarcinogenesis-validation of cIAP1 as a therapeutic target in liver cancer in a new mouse model of hepatocellular carcinoma," Hepatology, vol. 42, No4, Suppl 1, p. 244A (Oct. 2005).

Zender et al., "Small interfering RNA (SIRNA) and Antisense oligonucleotides (ASO) for Reversion of chemotherapy resistance in hepatoma cells," Journal of Hepatology, vol. 38, Suppl. 02, (Apr. 1, 2003).

Zeng et al., "Use of RNA Polymerase II to transcribe artificial MicroRNAs," Methods in Enzymology, vol. 392, pp. 371-380 (2005).

\* cited by examiner

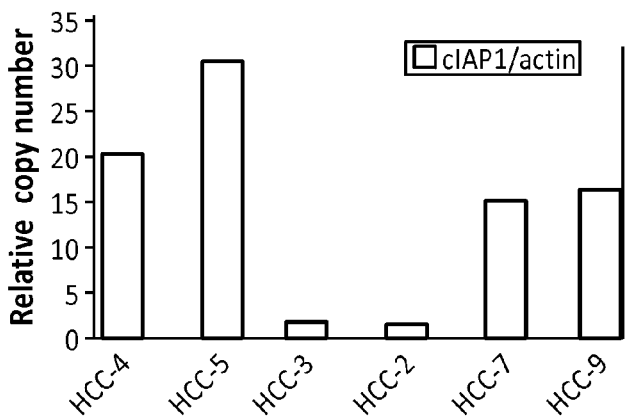
Fig. 2c
| Starting compound lesion | # animals analyzed | c-IAP1/2 amplicon present |
|---|---|---|
| p53-/-;c-myc | 5 | 4 |
| p53+/-;c-myc | 1 | 0 |
| p53+/-,Akt | 1 | 0 |
| p53-/-;Akt | 2 | 0 |
| p53-/-;Ras | 1 | 0 |
Fig. 2d
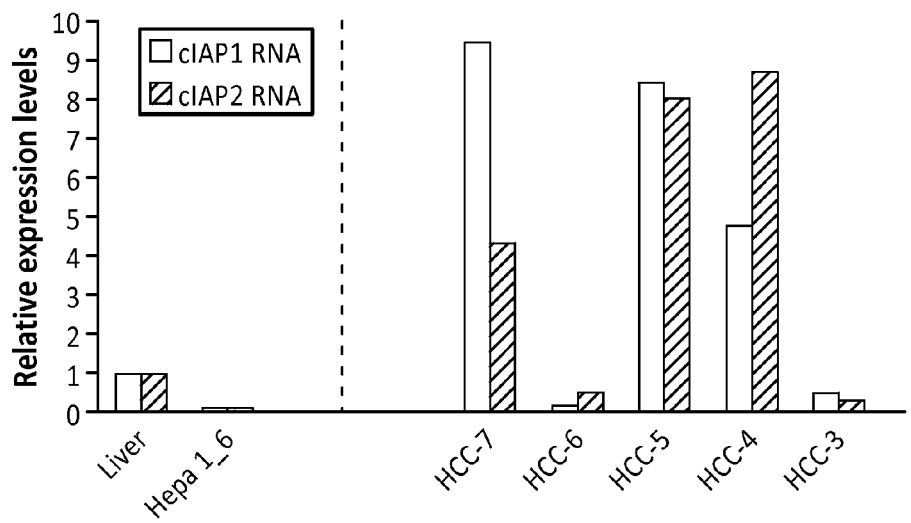
Fig. 2e ROMA arrayCGH analysis of 98 human Hepatocellular carcinomas 59 focal genomic deletions containing 362 genes Identification of 301 mouse homologs 631 shRNAmir available in RNAi Codex mouse library (pSM2c vector)

Compilation of focused "ROMA deletion" library set (pool size n=48)

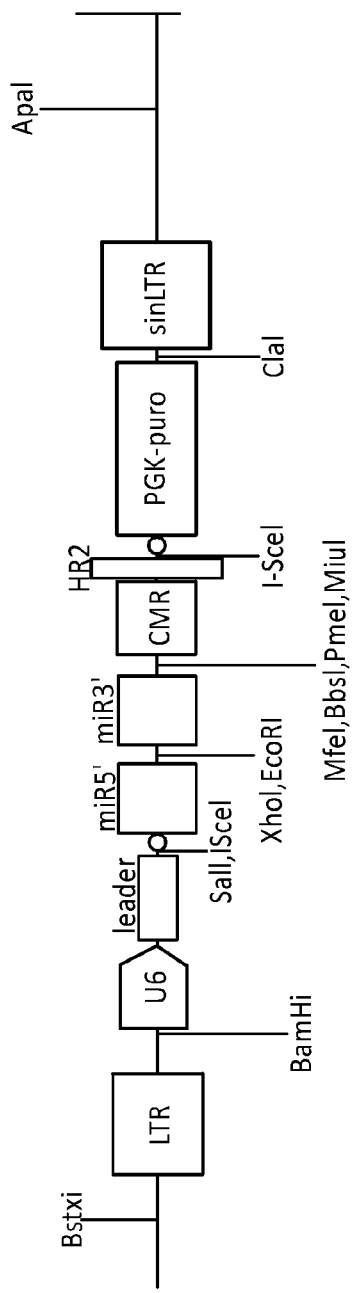
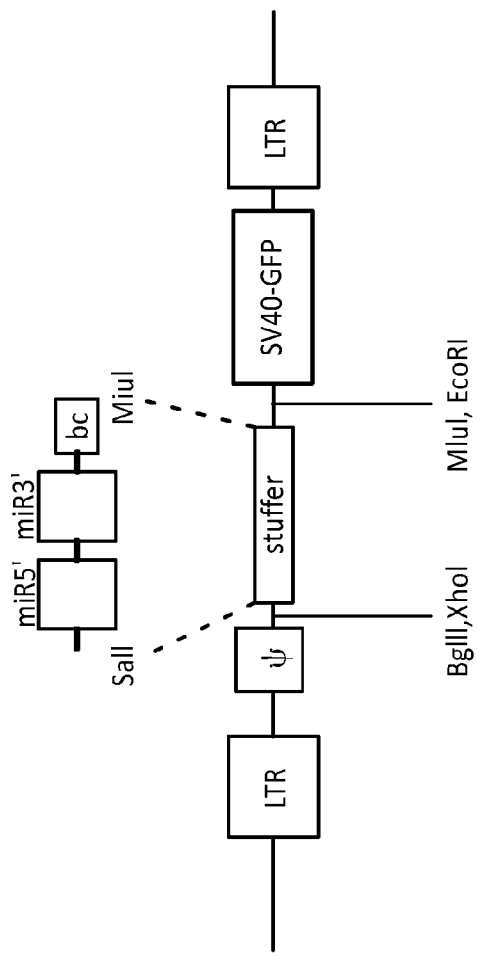
Fig. 14b
Fig. 14c

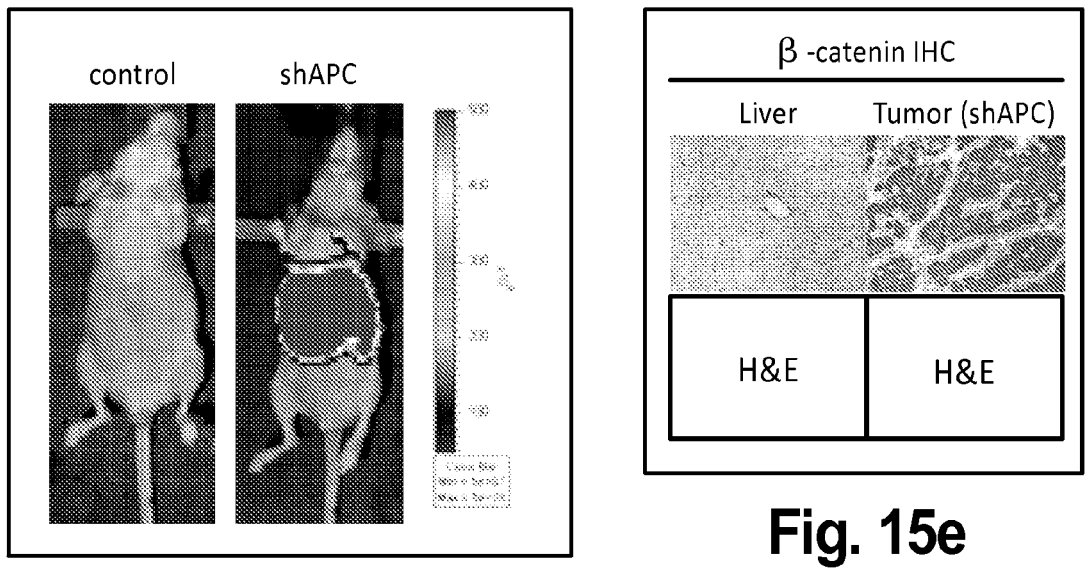
Fig. 15c
Fig. 15e
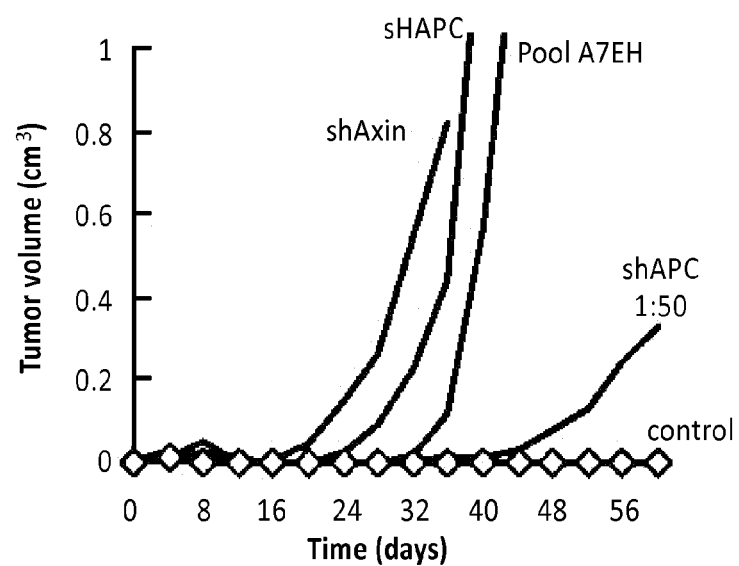
Fig. 15d

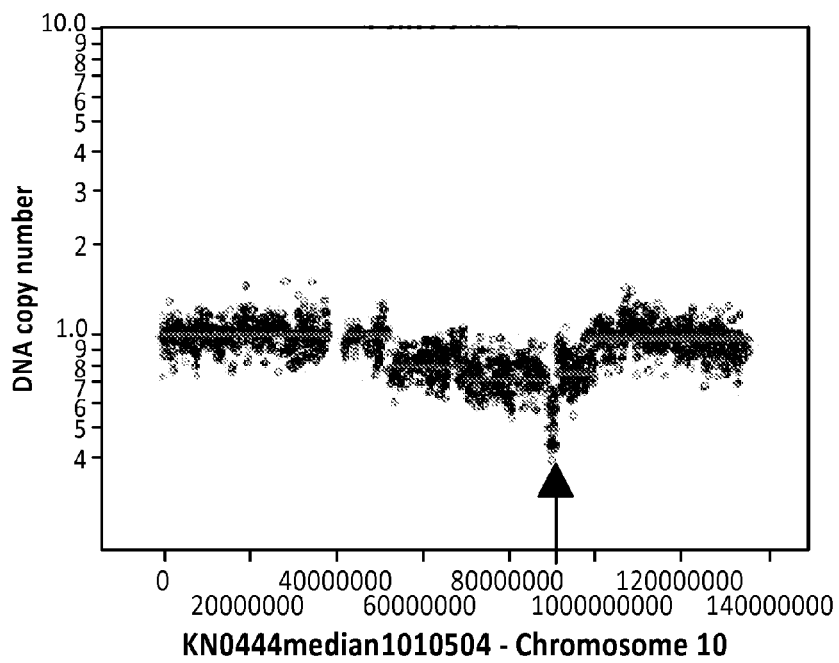
Fig. 16e
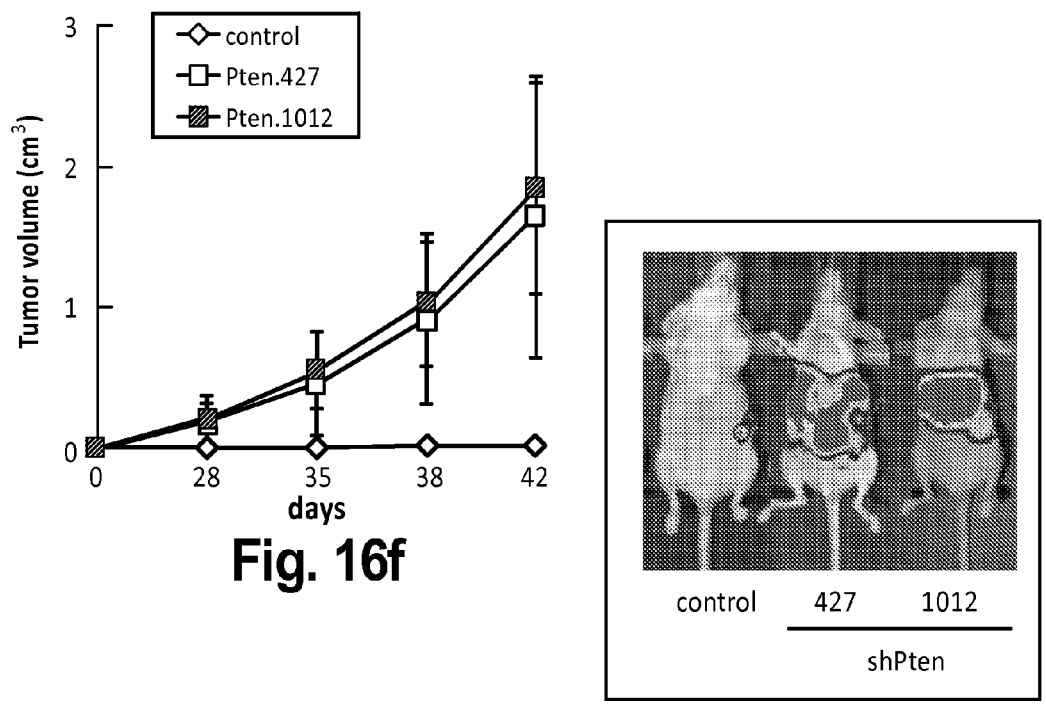
Fig. 16f
Fig. 16g

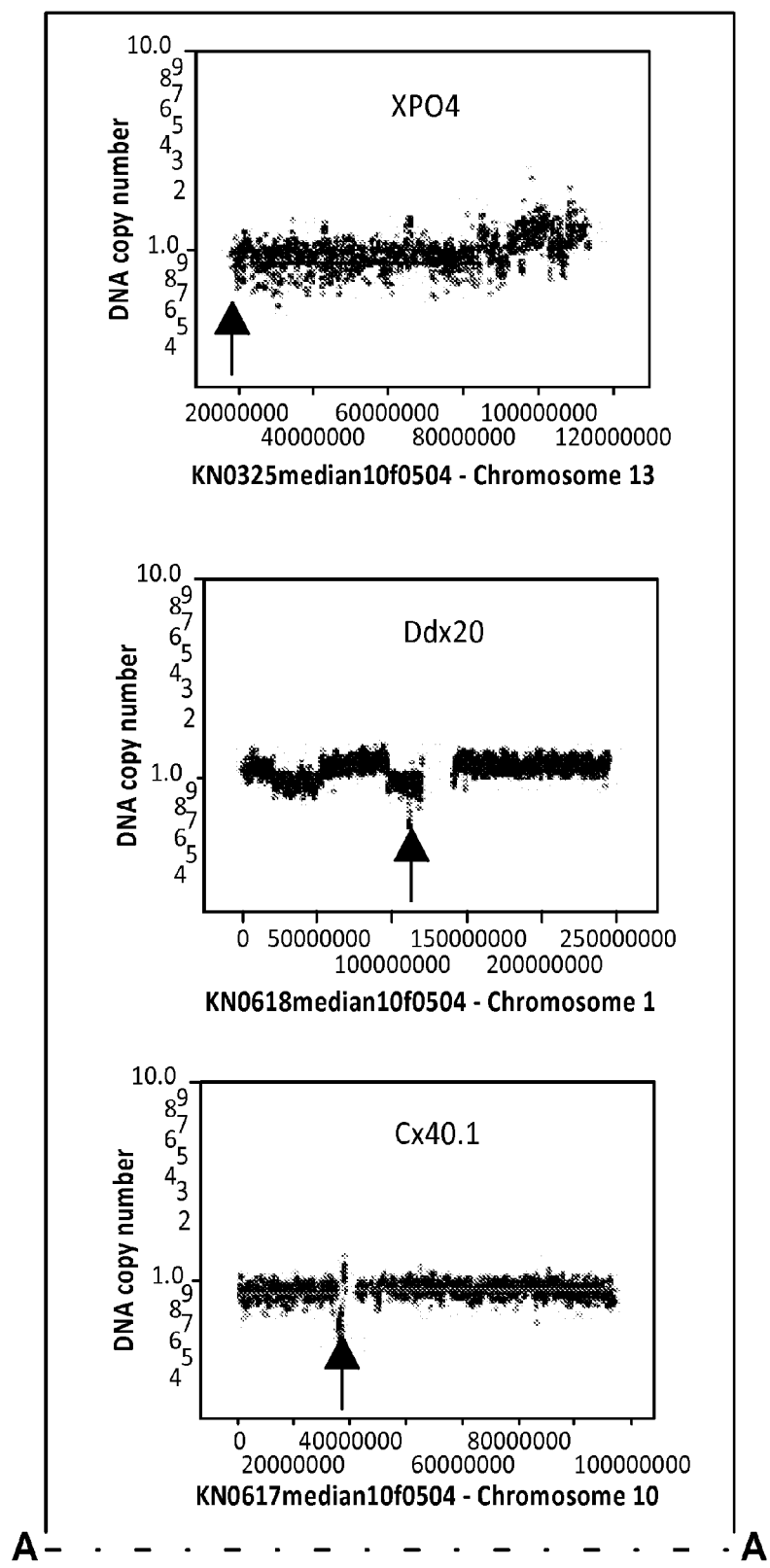
Fig. 17c(1)

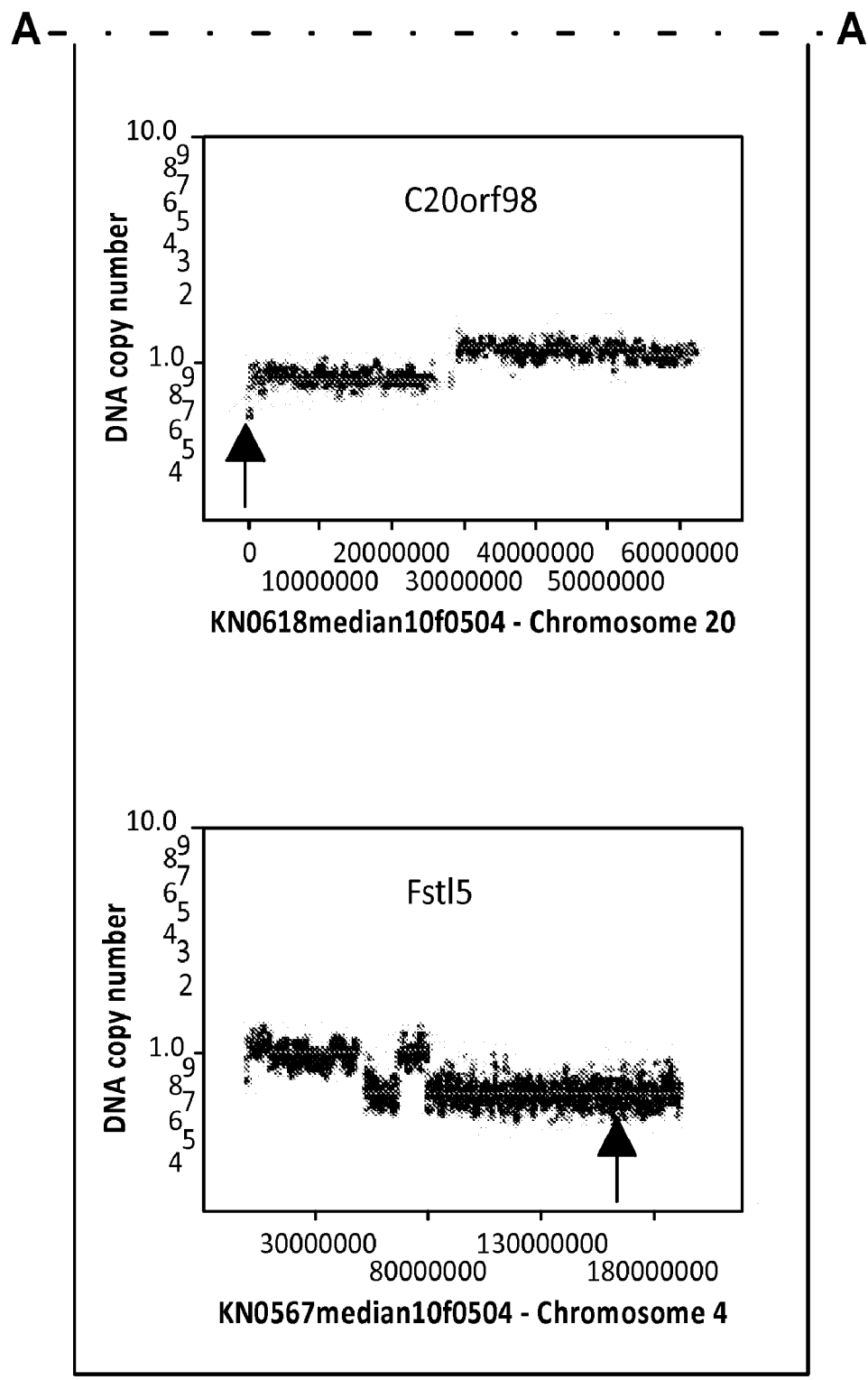
Fig. 17c(2)

ORTHOTOPIC AND GENETICALLY TRACTABLE NON-HUMAN ANIMAL MODEL FOR LIVER CANCER AND THE USES THEREOF

REFERENCE TO RELATED APPLICATIONS

This application is a continuation-in-part of U.S. application Ser. No. 11/325,218, filed on Jan. 3, 2006, which claims priority to U.S. Provisional Application No. 60/641,043, filed on Jan. 3, 2005, and U.S. Provisional Application No. 60/686,609, filed on Jun. 1, 2005. Each of the foregoing applications is hereby incorporated by reference in its entirety.

TECHNICAL FIELD OF THE INVENTION

This invention provides a genetically tractable in situ non-human animal model for liver cancer and specifically hepatocellular carcinoma. The model is useful, inter alia, in understanding the molecular mechanisms of liver cancer, in understanding the genetic alterations that lead to chemoresistance or poor prognosis, and in identifying and evaluating new therapies against hepatocellular carcinomas.

This invention also relates to the use of RNA interference (RNAi) technology in vivo to efficiently identify genes associated with tumorigenesis.

BACKGROUND INFORMATION

Cancer is the second leading cause of death in industrial countries. More than 70% of all cancer deaths are due to carcinomas, i.e., cancers of epithelial organs. Most carcinoma tumors show initial or compulsory chemoresistance. This property makes it very difficult to cure these tumors when they are detected in progressed stages. Primary forms of liver cancers include hepatocellular carcinoma, biliary tract cancer and hepatoblastoma. Hepatocellular carcinoma is the fifth most common cancer worldwide but, owing to the lack of effective treatment options, constitutes the leading cause of cancer deaths in Asia and Africa and the third leading cause of cancer death worldwide. Parkin et al. "Estimating the world cancer burden: Globocan 2000." *Int. J. Cancer* 94, 153-156 (2001).

The risk factors for liver cancer include excessive alcohol intake or other toxins, such as iron, aflatoxin B1 and also the presence of other infections such as hepatitis B and C. Alison & Lovell. "Liver cancer: the role of stem cells." *Cell Prolif.* 38, 407-421 (2005). The only curative treatments for hepatocellular carcinoma are surgical resection or liver transplantation, but most patients present with advanced disease and are not candidates for surgery. To date, systemic chemotherapeutic treatment is ineffective against hepatocellular carcinoma, and no single drug or drug combination prolongs survival. Llovet. et al. "Hepatocellular carcinoma." *Lancet* 362, 1907-1917. (2003). However, despite its clinical significance, liver cancer is understudied relative to other major cancers.

One of the difficulties in identifying appropriate therapeutics for tumor cells in vivo is the limited availability of appropriate test material. Human tumor lines grown as xenographs are unphysiological, and the wide variation between human individuals, not to mention treatment protocols, makes clinical studies difficult. Consequently, oncologists are often forced to perform correlative studies with a limited number of highly dissimilar samples, which can lead to confusing and unhelpful results.

Non-human animal models provide a useful alternative to studies in humans and to human tumor cell lines grown as xenographs, as large numbers of genetically-identical individuals can be treated with identical regimens. Moreover, the ability to introduce germline mutations that affect oncogenesis into these animals increases the power of the models.

To investigate the basic mechanisms of carcinogenesis and to test new potential cancer agents and therapies, however, realistic carcinoma-non-human animal models are urgently needed. So far there have been two major ways to create carcinoma non-human animal models: (i) the generation of transgenic or chimeric non-human animals that express oncogenes under the control of a tissue specific promoter and (ii) carcinomas that were induced by chemical carcinogens. Both approaches have several disadvantages.

Current animal models for cancer are based largely on classical transgenic approaches that direct expression of a particular oncogene to an organ of choice using a tissue specific promoter. See, e.g., Wang et al. "Activation of the Met receptor by cell attachment induces and sustains hepatocellular carcinomas in transgenic mice." *J. Cell Biol.* 153, 1023-1034 (2001). Although such models have provided important insights into the pathogenesis of cancer, they express the active oncogene throughout the entire organ, a situation that does not mimic spontaneous tumorigenesis. Moreover, incorporation of additional lesions, such as a second oncogene or loss of a tumor suppressor, requires genetic crosses that are time consuming and expensive, and again produce whole tissues that are genetically altered. Finally, traditional transgenic and knockout strategies do not specifically target liver progenitor cells, which may be the relevant initiators of the disease.

Cancer therapies that directly target oncogenes are based on the premise that cancer cells require continuous oncogenic signaling for survival and proliferation. Non-human animal models expressing oncogenes in genetic backgrounds that lack, or have down-regulated, tumor suppressor genes can thus serve as valuable tools to study tumor initiation, maintenance, progression, treatment and regression. However, responses to the targeting drugs are often heterogeneous, and chemoresistance and other resistance is a problem. Because most anticancer agents were discovered through empirical screens, efforts to overcome resistance are hindered by a limited understanding of why these agents are effective and when and how they become less or non-effective.

Furthermore, although cancer usually arises from a combination of mutations in oncogenes and tumor suppressor genes, the extent to which tumor suppressor gene loss is required for the maintenance of established tumors is poorly understood.

Variations in both non-human animal strains and promoters used to drive expression of oncogenes complicate the interpretation of cancer mechanistics and treatment analyses. Firstly, intercrossing strategies to obtain non-human animals of the desired genetic constellation are extremely time consuming and costly. Secondly, the use of certain cell-selective promoters can result in a cell-bias for tumor initiation. For example, the mouse mammary tumor virus (MMTV) promoter and the Whey Acidic Protein (WAP) promoter are commonly used to model breast cancer development in mice, and yet may not target all subtypes of mammary epithelia, i.e., stem cell and non-stem cells. Finally, a homogenous expression of the respective oncogene in all epithelial cells of an organ creates an unphysiological condition, as tumors are known to originate within genetic-mosaics.

An additional difficulty in identifying and evaluating the efficacy of cancer agents on tumor cells and understanding the molecular mechanisms of the cancers and their treatment in the current non-human animal models in vivo is the limited availability of appropriate material.

It is therefore important to use a valid model to identify new therapeutics for the treatment of liver cancer.

Investigation of the role of oncogenes or tumor suppressor genes in tumorigenesis can be facilitated by specifically silencing, or preventing from exerting its presence, the particular gene of interest. One such silencing means is through "RNA interference" or "RNAi." RNAi stems from a phenomenon observed in plants and worms whereby double-stranded RNA (dsRNA) blocks gene expression in a specific and post-transcriptional manner. The dsRNA is cleaved by an RNAse III enzyme "DICER" into a 21-23 nucleotide small interfering RNA (siRNA). These siRNAs are incorporated into a RNA-induced silencing complex (RISC) that identifies and silences RNA complimentary to the siRNA. Without being bound by theory, RNAi appears to involve silencing of cytoplasmic mRNA by triggering an endonuclease cleavage, promoting translation repression, or possibly accelerating mRNA decapping (Valencia-Sanchez et al., 2006, *Genes & Development* 20: 515-524). Biochemical mechanisms of RNAi are currently an active area of research.

Three mechanisms of utilizing RNAi in mammalian cells have been described. The first is cytoplasmic delivery of siRNA molecules, which are either chemically synthesized or generated by DICER-digestion of dsRNA. These siRNAs are introduced into cells using standard transfection methods. The siRNAs enter the RISC complex to silence target mRNA expression.

The second mechanism is nuclear delivery, via viral vectors, of gene expression cassettes expressing a short hairpin RNA (shRNA). The shRNA is modeled on micro interfering RNA (miRNA), an endogenous trigger of the RNAi pathway (Lu et al., 2005, *Advances in Genetics* 54: 117-142, Fewell et al., 2006, *Drug Discovery Today* 11: 975-982). The endogenous RNAi pathway is comprised of three RNA intermediates: a long, largely single-stranded primary miRNA transcript (pri-mRNA), a precursor miRNA transcript having a stem-and-loop structure and derived from the pri-mRNA (pre-miRNA), and a mature miRNA. The miRNA gene is transcribed by an RNA polymerase II promoter into the pri-mRNA transcript, which is then cleaved to form the pre-miRNA transcript (Fewell et al., supra). The pre-miRNA is transported to the cytoplasm and is cleaved by DICER to form mature miRNA. miRNA then interacts with the RISC in the same manner as siRNA. shRNAs, which mimic pre-miRNA, are transcribed by RNA Polymerase II or III as single-stranded molecules that form stem-loop structures. Once produced, they exit the nucleus, are cleaved by DICER, and enter the RISC complex as siRNAs.

The third mechanism is identical to the second mechanism, except that the shRNA is modeled on pri-miRNA (shRNAmir), rather than pre-miRNA transcripts (Fewell et al., supra). An example is the miR-30 miRNA construct. The use of this transcript produces a more "physiological" shRNA that reduces toxic effects. The shRNAmir is first cleaved to produce shRNA, and then cleaved again by DICER to produce siRNA. The siRNA is then incorporated into the RISC for target mRNA degradation.

RNAi has been used to successfully identify and suppress target genes associated with tumorigenesis. For example, expression of microRNA-based shRNA specific to Trp53 produces "potent, stable, and regulatable gene knock-down in cultured cells . . . even when present at a single copy in the genome" (Dickins et al., 2005, *Nature Genetics* 37: 1289-1295). The tumors induced by the p53 knockdown regress upon re-expression of Trp53. Id. The suppression of the Trp53 gene expression by shRNA is also possible in stem cells and reconstituted organs derived from those cells (Hemann et al., 2003, *Nature Genetics* 33: 396-400). Moreover, the extent of inhibition of p53 function by the shRNA correlates with the type and severity of subsequent lymphomagenesis. Id.

However, there are conflicting views on which method of introducing and using RNAi mechanism is most effective. Some studies emphasize siRNA's several drawbacks, including transient effects, difficulty in delivery to nondividing primary cells, and concentration-dependent off-target effects. shRNAs expressed from viral vectors "are more versatile, allowing . . . stable integration, germline transmission, and the creation of in vivo animal models (Fewell et al., supra). shRNA is also more suitable for hard-to-transfect cells, due to its infection-based delivery, and has decreased concentration-dependent off-target effects. Id. In comparison with shRNA, shRNAmir is more efficiently processed into siRNA and produces a more consistent silencing of mRNA than shRNA. Id.

Despite the advantages of shRNA, other studies maintain that use of siRNA for RNAi purposes is emerging more rapidly than the use of shRNA (Lu et al., supra), partly because of the "increased effort required to construct shRNA expression systems before selection of active sequences and verification of biological activity are obtained." Id. It is often time consuming and expensive to both construct shRNA expression cassettes and incorporate them into viral delivery systems. Id. On the contrary, use of synthetic oligonucleotides allows for rapid screening and studying of siRNA sequences and matching genes. Id. Moreover, recent studies investigating in vivo applications of RNAi focus on non-viral delivery of siRNA constructs as opposed to viral delivery of shRNA constructs, as viral vectors often raise concerns about safety and immunogenecity (Lu et al., supra; Vohies et al., 2007, *Expert Rev. Anticancer Ther.* 7: 373-382). In sum, there is no established method of RNAi that consistently produces the most effective RNA silencing.

Studies also vary in their use of genome-wide collections of pooled shRNA vectors versus small sets of shRNA vectors that target a specific gene family. The use of large shRNA libraries may lead to difficulties in measuring the relative abundance of each individual shRNA vector in a complex population of cells infected with thousands of vectors. In addition, the smaller scaled experiments allow "screening for relatively labor-intensive phenotypes." Id. Pooled screens also pose several technological hurdles, such as obtaining uniform pools of viruses, creating robust design algorithms that enable gene knockdown at a single-copy level, and preventing large numbers of false positives (Fewell et al., supra). On the other hand, the use of barcodes, or unique sequence of nucleotides incorporated into each shRNA vector, allows for more accurate quantification of specific shRNAs in pooled analyses (Bernards et al., 2006, *Nature Methods* 3: 701-706). Moreover, larger shRNA library screens can be used to select for long-term phenotypes while smaller shRNA screens are mainly limited to "short-term" readouts. Id. Given the various benefits and drawbacks of both large and small scale screens, there is no suggestion that use of one method or the other is the most effective strategy for successful RNAi.

Finally, although certain tumor suppressors such as p53 are well-studied, the importance of other individual tumor suppressors is still unknown. As such, the extent of overall tumor suppressor gene loss required for maintaining tumors is poorly understood. Moreover, although there is potential to utilize Myc overexpression to investigate novel tumor suppressor genes, few scientists have so far been able to do so.

Established approaches for the investigation of novel oncogenes and tumor suppressor genes using RNAi are thus unavailable. As such, the invention described herein will further elucidate the mechanism of tumorigenesis and promote the development of treatment methods based on such understanding.

SUMMARY OF THE INVENTION

The invention provides in vivo and in vitro systems and methods for the study of the effects of tumorigenesis, tumor maintenance, tumor regression and altered expression of a gene activity, on the descendants of embryonic liver progenitor cells, or primary hepatocytes, that have been engineered to produce hepatocellular carcinomas.

The liver cancer model of this invention is made by altering hepatocytes to increase oncogene expression, to reduce tumor suppressor gene expression or both and by transplanting the resulting hepatocytes into a recipient non-human animal. The spontaneous mutations arising in tumors initiated by different oncogenic lesions are compared to alterations observed in human cancers. Preferably, the transplanting is carried out so that the hepatocytes engraft the liver of the animal and a liver cancer tumor develops there from at least one of the altered hepatocytes. Less preferably, the altered hepatocytes are transplanted subcutaneously into a non-human animal so as to develop a tumor.

The non-human animal model of hepatocellular carcinoma embodied herein is useful for identifying molecular targets for drug screening, for identifying interacting gene activities, for identifying therapeutic treatments and for identifying candidates for new therapeutic treatments. The invention also provides methods and non-human animals produced by the methods that are useful for understanding liver cancer and its treatments, and in particular, for identifying and studying inhibitors and activators associated with liver tumor cell growth and growth inhibition, cell death through apoptotic pathways, and changes in apoptotic pathway components that affect drug sensitivity and resistance in tumorigenic cells.

The genetically tractable, transplantable in situ liver cancer model of this invention is characterized by genetically defined hepatocellular carcinomas that are preferably traceable by external green fluorescent protein (GFP) imaging. To further characterize the genetic defects in these tumors, gene expression profiling, e.g., representational oligonucleotide microarray analysis (ROMA), can be used to scan the carcinomas for spontaneous genomic gains and losses in gene copy number. Detecting genomic copy number changes through such high resolution techniques can be useful to identify oncogenes (amplifications or gains) or tumor suppressor genes (deletions or losses). Identification of overlapping genomic regions altered in both human and mouse gene array datasets may further aid in pinpointing of regions of interest that can be further characterized for alterations in RNA and protein expression to identify candidates are most likely to contribute to the disease phenotype and to be the "driver gene" for amplification.

Using "forward genetics" in combination with gene expression profiling (e.g., ROMA) and the non-human animal models of this invention, important insights into the molecular mechanisms of hepatocarcinogenesis, growth, maintenance, regression and remission can be obtained. The models of the invention can directly evaluate the potency of various oncogenes in producing anti-apoptotic phenotypes, and various tumor suppressor genes in producing apoptotic phenotypes. Candidate oncogenes or tumor suppressors can be rapidly validated in the mouse model of the invention by overexpression, or by using stable RNAi technology, respectively. The invention is also useful in analyzing and evaluating genetic constellations that confer chemoresistance or poor prognosis. Furthermore, the invention is useful for identifying and evaluating new therapies for the treatment of carcinomas.

Another aspect of the instant invention is a method of identifying a novel gene that is associated with tumorigenesis, such as a tumor suppressor gene. The method comprises (1) transfecting a plurality of hepatocytes with a library of RNAi molecules, wherein each of the RNAi molecule inhibits expression of a target gene, (2) transplanting the transfected cells into a recipient non-human animal, and (3) identifying the RNAi molecule that give rise to liver cancer in the recipient animal. The RNAi molecule may be identified, for example, by isolating the genomic DNA from the cancer cells, amplifying the transfected RNAi molecule by PCR, and sequencing the amplified DNA.

In certain embodiments, the RNAi library comprises RNAi molecules that inhibit the expression of genes known to be up-regulated or down-regulated in human cancers, such as liver cancer. In certain embodiments, the RNAi library comprises RNAi molecules that inhibit the expression of genes that are deleted in a cancer genome. In particular, the RNAi library may comprise RNAi molecules that inhibit the expression of genes that are located within a recurrent genomic deletion found in two or more cancer genomes.

In another aspect, the invention discloses tumor suppressor genes whose down-regulation is associated with liver cancer, as listed in Table 1, Example 2.

Another aspect of the invention is a method of treating cancer comprising the steps of determining the status in cancerous tissue of one or more of the tumor suppressor genes described herein or identified by the screening method described herein, and if any of the tumor suppressors shows a decreased expression or activity in cancerous tissue in comparison to a control (such as a normal tissue), increasing the expression of said tumor suppressor(s).

In one embodiment, the expression or activity of a tumor suppressor is increased by introducing the tumor suppressor into the cancerous tissue. In a particular embodiment, the tumor suppressor protein or a physiologically active fragment, analog, or mutant thereof is administered. In another particular embodiment, the tumor suppressor gene or a fragment or mutant thereof that encodes a physiologically active polypeptide is introduced into the cancer tissue and expressed. In yet another embodiment, known upstream factors of an identified tumor suppressor is modulated to increase the tumor suppressor expression.

Another aspect of the invention is a method of treating cancer comprising determining in cancerous tissue the expression of one or more tumor suppressor genes described herein or identified by the screening method described herein, the expression of which gene or genes are increased or decreased in comparison to a control (e.g., a normal tissue), and administering a therapeutic agent that is known to be effective in treating such cancers that are associated with the increased or decreased expression of such gene or genes. Alternatively, an aspect of the invention is a method of treating cancer comprising the steps of determining in cancerous tissue the expression of one or more tumor suppressor genes described herein or identified by the screening method described herein, the expression of which gene or genes are decreased in comparison to a control (e.g., a normal tissue), and administering a therapeutic agent that is known not to antagonize the gene or genes identified herein.

In another aspect, the invention discloses a method for identifying a subject who is suffering from or susceptible to liver cancer, comprising: determining the expression level of one or more identified tumor suppressor genes. A decrease in the expression level of the tumor suppressor gene, as compared to a control, is indicative of a subject suffering from or susceptible to liver cancer.

Yet another aspect of the invention is a pharmaceutical composition comprising a therapeutic agent for the treatment of cancer, which composition has specific utility to treat such cancer that has certain status regarding one or more tumor suppressors identified using the method described herein.

One embodiment of the invention is a pharmaceutical composition for the treatment of cancer in which the expression or activity of said tumor suppressor is less than a control (e.g., in normal tissue), comprising a tumor suppressor protein or a physiologically active fragment, analog, or mutant thereof. Another particular embodiment is a pharmaceutical composition for the treatment of cancer in which the expression or activity of a tumor suppressor is less than a control (e.g., in normal tissue), comprising a tumor suppressor gene or a fragment or mutant thereof that encodes a physiologically active polypeptide is introduced into the cancer tissue and expressed. In yet another embodiment, a pharmaceutical composition comprises one or more therapeutic agents that modulate known upstream factors of an identified tumor suppressor to increase the tumor suppressor expression.

The invention further relates to a hepatocyte transfected with an RNAi molecule, wherein the expression of the RNAi molecule transforms the hepatocyte into a cancer cell. In certain embodiments, the hepatocyte is a c-myc/p53−/− embryonic hepatocyte.

The invention further relates a non-human animal model comprising: (1) a hepatocyte transfected with an RNAi molecule, wherein the expression of the RNAi molecule causes the animal to develops liver cancer.

Figure 1A:
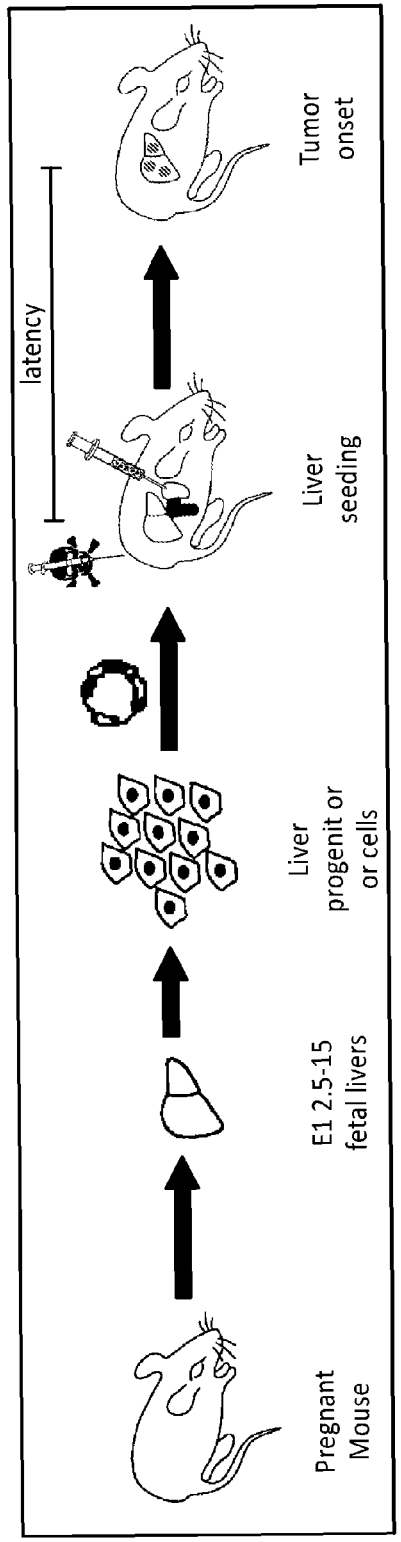
FIG. 1: Development and characterization of a new orthotopic, genetically tractable mouse model for hepatocellular carcinoma. (a) Schematic outline of two claims of producing a non-human animal liver cancer model of this invention. E-Cadherin+ mouse hepatoblasts are isolated from day 13-15 mouse liver using the MACS® indirect labeling system in combination with the ECCD-1 E-Cadherin antibody. Purified hepatoblasts are grown in short term primary-culture on irradiated NIH-3T3 feeder layers. The hepatoblasts are infected with GFP-tagged murine stem cell virus (MSCV) based retroviruses expressing oncogenes of interest (e.g., the H-ras oncogene) and/or expression cassettes for short hairpin RNAs directed against tumor suppressor genes (e.g., p53). After viral transduction, infected hepatoblasts are either injected into the spleens of retrorsine-conditioned recipient mice or subcutaneously into NCR nu/nu mice. Retrorsine efficiently blocks the cell cycle of hepatocytes and additionally causes a moderate liver damage by triggering apoptosis in a small number of hepatoblasts. Using this approach, after intrasplenic transplantation, genetically modified hepatocytes migrate via the portal vein into the recipient liver and engraft the organ. Transplanted hepatoblasts harboring the defined genetic lesions clonally expand and hepatocellular carcinomas develop in the liver. Tumor onset and growth kinetics can be monitored by external whole body GFP-imaging as all viral vectors carry a GFP expression cassette. (b) Transplanted hepatoblasts engraft the recipient liver and are morphologically indistinguishable from the host hepatocytes (H&E). Immunofluorescence with a primary antibody directed against GFP allows detection of the transplanted hepatocytes (middle). DAPI counterstaining (right). (c) p53 deficient liver progenitor cells transduced with different oncogenes (myc, akt or H-rasV12) give rise to orthotopic liver carcinomas after intrahepatic seeding. Detection of intrahepatic liver carcinomas by whole body, external GFP-tumor imaging (top panel) or direct imaging of the respective explanted tumor bearing livers (bottom panel). Tumors can be detected by either external GFP imaging (upper panel) or direct GFP-imaging of the explanted liver (lower panel). (d) Kaplan-Meier curve for survival times of mice transduced with different oncogenes (myc, akt, H-rasV12). All groups succumb to death much earlier than mice injected with p53−/− control vector alone. (e) Cells from primary murine liver carcinomas (p53−/−; myc) were grown briefly in culture. In situ liver carcinomas were generated by direct subcapsular injection of the cells into the left liver lobe. Shown are GFP-tumor imaging (left) and a photograph of the in situ tumors (right) day 42 post-injection.
Figure 1B:
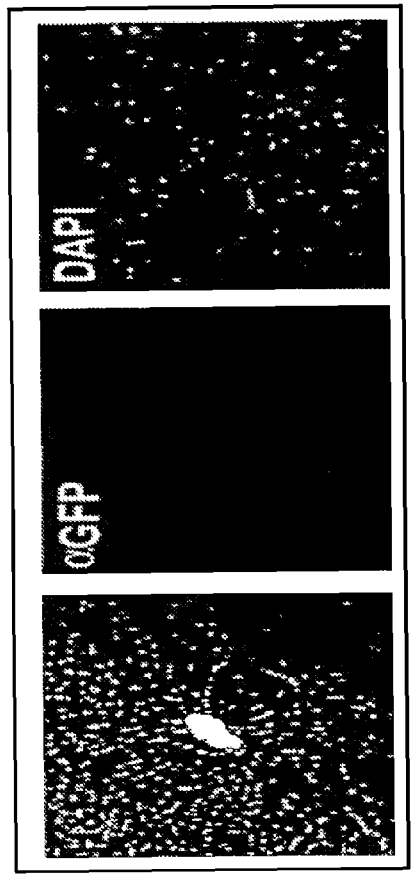

Single probe resolution of chromosome 15 reveals increased copy number for Rnf19 and myc. (c) Genome-wide profiles of three independent HCCs (Tu-7, Tu-9, Tu-13) derived from p53−/−; myc embryonic hepatoblasts are overlaid and reveal a recurrent overlapping DNA amplification on chromosome 9. (d) Single probe resolution of the amplicon on chromosome 9qA1; minimal overlap region contains genes indicated.

FIG. 9: ROMA identifies amplification of the human syntenic region 11q22 in HCC and other cancers. (a) Genome-wide profile of a human HCC reveals an amplification on chromosome 7 containing the c-MET gene and 3 regions amplified on chromosome 11. (b) Single probe resolution of chromosome 11; 11q13 contains CCND1; B' contains no known genes; 11q22 contains the genes depicted. (c) Single probe resolution of chromosome 11 of a representative esophageal tumor. 11q22 contains same genes as shown in b. (d) Genome-wide profile of an ovarian carcinoma reveals chromosome 11 amplification. (e) Single probe resolution of the 11q22 amplicon shows a lack of amplification of the MMP cluster.

FIG. 10: cIAP1 is overexpressed in tumors containing elevated cIAP1 gene copy number (a) cIAP1 and cIAP2 are overexpressed in murine HCCs as determined by quantitative realtime RT-PCR analysis. *denotes tumors with elevated cIAP1 gene copy number. (b) cIAP1 protein is overexpressed in outgrown murine HCC tumor cells containing the 9qA1 amplicon as assayed by immunoblotting using a monoclonal anti-cIAP antibody (top panel) or a polyclonal anti-cIAP1/2 antiserum (middle panel). Tubulin served as a loading control. (c) Quantitative real-time RT-PCR analysis of cIAP1 and cIAP2 expression in human HCCs. (d) Quantitative real-time RT-PCR analysis of cIAP1 and cIAP2 expression in a subset of human esophageal carcinomas. *denotes tumor with elevated cIAP1 gene copy number (c+d).

FIG. 11: cIAP1 overexpression in p53−/−; myc hepatoblasts suppresses p53 independent forms of apoptosis induced by different death stimuli. (a) Expression of myc-tagged-cIAP1 in p53−/−; myc liver progenitor cells (right lane) was confirmed by western blot analysis using a monoclonal anti-cIAP1 antibody. Left lane (V) is lysate from cells infected with vector alone. (b) cIAP1 expression protects hepatoblasts from apoptosis mediated by serum withdrawal. p53−/− hepatoblasts, double infected with myc+cIAP1 or myc+vector were grown in the serum conditions indicated for 48 hrs. Apoptosis was measured using the Cell Death Detection ELISAPLUS (Roche). Error bars denote the standard deviation of three measurements per data point (B-D). (c) cIAP1 protects against spontaneous cell death mediated by contact inhibition. p53−/− hepatoblasts (myc+cIAP1 or myc+vector) were grown to confluence and apoptosis was measured [as in (B)] 24 hours later. (d) cIAP1 protects against FasL triggered cell death but not TNFa or TRAIL mediated cell death of liver progenitor cells. p53−/− hepatoblasts (myc+cIAP1 or myc+vector) were treated with 125 ng/ml TRAIL, 5 ng/ml TNFa or increasing concentrations of FasL (25, 50, 100 ng/ml) together with 2.5 ug/ml cycloheximide for 12 hrs. Apoptosis was measured as in (b). (e) cIAP1 increases short and long-term viability following FasL treatment. p53−/− hepatoblasts (Myc+cIAP1 or Myc+vector) were treated with 50 ng/ml FasL for 36 hrs. Representative phase contrast photographs (upper panel, left) depict floating, apoptotic cells (arrow) and viable, attached cells (right, arrowhead). Cells that underwent the same treatment were cultured for 5 more days without FasL and stained with crystal violet to visualize clonogenic survival (lower panel).

FIGS. 12. cIAP1 enhances the tumorigenicity of Myc overexpressing p53−/− hepatoblasts. (a) p53−/− hepatoblasts were double-infected with myc plus myc-tagged-cIAP1 or myc plus vector and were subcutaneously injected into the rear flanks of nude mice (n=6 for each group). Tumor size was assessed by caliper measurement. Shown is a representative of three independent experiments. (b) Immunoblot of tumor lysates for cIAP1 protein level. Protein lysates from 6 representative tumors overexpressing myc-tagged-cIAP1 (lanes 8-13) and control vector tumors (lanes 5-7) were probed with anti-cIAP1 antibody. Cells lysates from cultured myc-tagged-cIAP1 expressing hepatoblasts (M, lane 2) or vector alone (V, lane 1) and from 9qA1 amplicon containing cells (A+, lane 4) were loaded for comparison to indicate exogenously expressed, myc-tagged-cIAP1 (75 kD) and endogenous cIAP1 (65 kD). A− is lysate from amplicon negative cells of the same genotype (p53−/−; myc). Tubulin is used as a loading control. (c) cIAP1 does not enhance the tumorigenicity of H-rasV12 overexpressing p53−/− hepatoblasts. n=6 for each group. (d) Immunoblot of tumor lysates from 3 representative mice of each group shown in (C) probed with anti-clAP1 antibody. (e) clAP1 does not enhance the tumorigenicity of Akt overexpressing p53−/− hepatoblasts. (f) Immunoblot of tumor lysates from 3 representative mice of each group shown in (e) probed with anti-clAP1 antibody.

FIG. 13. Tumors bearing the 9qA1 amplicon show delayed growth upon clAP1 and clAP2 suppression. (a) Hepatoma cells outgrown from a 9qA1 amplicon positive, p53−/−; Myc tumor, were double infected with shRNAs targeting clAP1 and clAP2 or control vectors (V), or no vector (−). Expression of clAP1 and clAP2 is significantly reduced as shown on the immunoblots that were probed with a monoclonal anti-clAP1 antibody (top panel) and a polyclonal anti-clAP1/2 antibody (second panel). The levels of XIAP were not reduced (third panel). Equal amounts of protein were loaded as assessed by tubulin levels. *denotes a non-specific band. (b) Stable suppression of clAP1 and clAP2 slows tumor growth of p53−/−; myc mouse hepatoma cells that contain the 9qA1 amplicon. Tumorigenicity of the cells described in (a) after injection into the rear flanks of nude mice. Growth of subcutaneous tumors was assessed by caliper measurement. (c) Stable suppression of clAP1 and clAP2 does not slow tumor growth of p53−/−; myc mouse hepatoma cells that do not contain the 9qA1 amplicon. (d) Stable suppression of p53 does not slow tumor growth of p53−/−; myc mouse hepatoma cells that contain the 9qA1 amplicon.

FIG. 14. In vivo RNAi screening to identify new tumor suppressor genes in liver cancer. (a) Schematic illustration of an in vivo RNAi screening protocol according to the teachings of the invention. (b) and (c) Shuffling of SalI/MluI fragments (containing shRNAmir and a unique barcode sequence for every shRNA) from the low complexity pSM2c library pools (b) into an MSCV based retroviral vector which has been optimized for in vivo use (c).

Figure 15A:
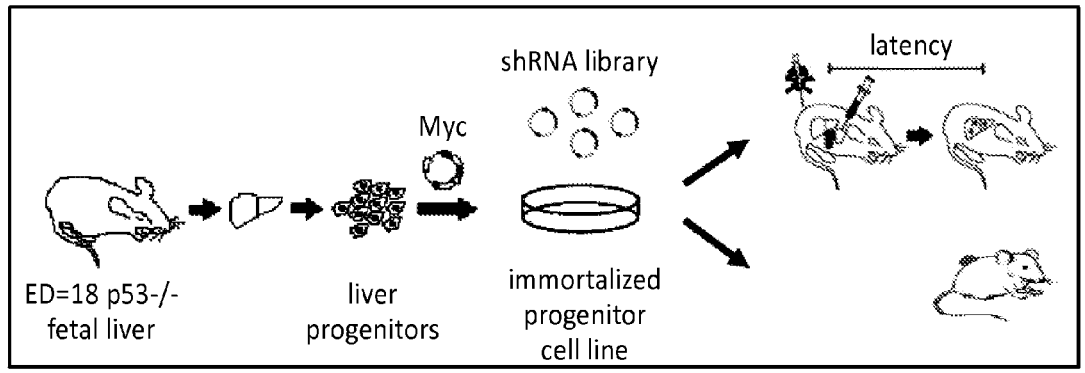
Figure 15B:
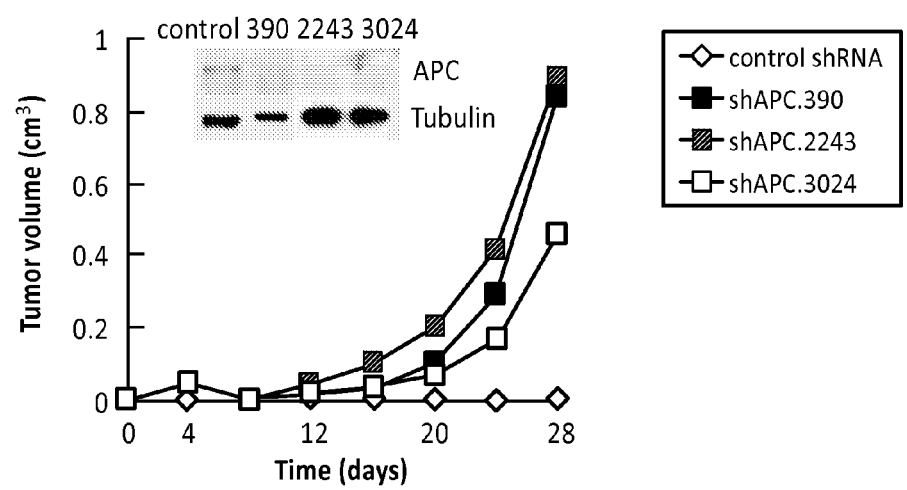

FIG. 15 shows that shRNAmir molecules targeting the APC tumor suppressor gene trigger tumor growth.

FIG. 16 shows the identification of new tumor suppressor genes in liver cancer, using in vivo RNAi screening. shRNAmir molecules targeting PTEN trigger the growth of liver carcinomas.

FIG. 17 shows the functional validation of candidate tumor suppressor genes.

FIG. 18 shows that the loss of Xpo4 promotes tumorigenesis.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, cell and cancer biology, virology, immunology, microbiology, genetics and protein and nucleic acid chemistry described herein are those well known and commonly used in the art.

The methods and techniques of the present invention are generally performed according to conventional methods well known in the art and as described in various general and more specific references that are cited and discussed throughout the present specification, unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2003); Harlow and Lane, *Antibodies: A Laboratory Manual*, Cold Spring Harbor Laboratory Press, Cold Spring Harbor, N.Y. (1990); Coffin et al., *Retroviruses*, Cold Spring Harbor Laboratory Press; Cold Spring Harbor, N.Y. (1997); Bast et al., *Cancer Medicine*, 5th ed., Frei, Emil, editors, BC Decker Inc., Hamilton, Canada (2000); Lodish et al., *Molecular Cell Biology*, 4th ed., W. H. Freeman & Co., New York (2000); Griffiths et al., *Introduction to Genetic Analysis*, 7th ed., W.H. Freeman & Co., New York (1999); Gilbert et al., *Developmental Biology*, 6th ed., Sinauer Associates, Inc., Sunderland, Mass. (2000); and Cooper, *The Cell—A Molecular Approach*, 2nd ed., Sinauer Associates, Inc., Sunderland, Mass. (2000). All of the above and any other publications, patents and published patent applications referred to in this application are specifically incorporated by reference herein.

I. Animal Models for Liver Cancer

The genetically tractable, transplantable in situ liver or hepatocellular cancer model of the invention offers unique advantages. This invention employs the proliferative capacity of the liver to enable the altered hepatocytes to reconstitute liver tissue. Large amounts of primary epithelial cells can be isolated according to standardized protocols either from adult mouse livers or from embryonic mouse livers. The primary culture conditions for embryonic, as well as adult primary hepatocytes, are based on well-established protocols and are less complex compared to other epithelial primary cultures. A sample of the primary cells can be used for RT-PCR characterization for liver specific markers to rule out overgrowing by non-parenchymal cells.

Primary adult or embryonic hepatocyte cultures can be genetically modified by infection with lentiviral- or retroviral vectors carrying various genetic alterations, including oncogenes or short hairpin RNAs against tumor suppressor genes. Virally transduced primary hepatocytes can efficiently engraft the livers of non-human animals after transplantation into their portal vein or spleen. In the case of certain genetic configurations, mice developed hepatocellular carcinomas that could be visualized by whole body fluorescence imaging. For example, introduction of a myc retrovirus into p53 deficient hepatocytes produced highly aggressive tumors that show many features of human hepatocellular carcinoma. Overall, it provides rapid generation of genetically defined hepatocellular carcinomas.

The invention embodies a method of making a non-human animal bearing a liver cancer using transplanted hepatocytes altered to increase oncogene expression, to reduce tumor suppressor gene expression or both. Preferably, the hepatocytes are virally transduced with a vector expressing an oncogene or a short hairpin RNA against a tumor suppressor gene and subsequently transplanted into a recipient non-human animal wherein the animal develops liver cancer tumors from at least one of the hepatocytes with altered gene expression.

As used herein, a non-human animal includes any animal, other than a human. Examples of such non-human animals include without limitation: aquatic animals, e.g., fish, sharks, dolphins and the like; farm animals, e.g., pigs, goats, cows, horses, rabbits and the like; rodents, e.g., rats, guinea pigs and mice; non-human primates, e.g., baboons, chimpanzees and monkeys; and domestic animals, e.g., cats and dogs. Rodents are preferred. Mice are more preferred.

The non-human animals can be wild type or can carry genetic alterations. For example, they may be immunocompromised or immunodeficient, e.g., a severe combined immunodeficiency (SCID) animal.

As used herein, hepatocytes include all descendants of embryonic liver progenitor cells. Preferably, primary hepatocytes are used in the methods and models of this invention. Primary hepatocytes from adult non-human animals or embryonic liver progenitor cells can be isolated using standard and conventional protocols. In short term primary culture the hepatocytes can be virally transduced with vectors carrying oncogenes and/or expression cassettes for short hairpin RNAs directed against tumor suppressor genes. Such transductions may be effected using standard and conventional protocols.

The term vector refers to a nucleic acid molecule capable of transporting another nucleic acid to which it has been linked. One type of vector is a plasmid, which refers to a circular double stranded DNA loop into which additional DNA segments may be ligated. A preferred type of vector for use in this application is a viral vector, wherein additional DNA segments may be ligated into a viral genome that is usually modified to delete one or more viral genes. Certain vectors are capable of autonomous replication in a host cell into which they are introduced (e.g., vectors having an origin of replication which functions in the host cell). Other vectors can be integrated stably into the genome of a host cell upon introduction into the host cell, and are thereby replicated along with the host genome. Preferred viral vectors include retroviral and lentiviral vectors. Moreover, certain preferred vectors are capable of directing the expression of nucleic acid sequences to which they are operatively linked. Such vectors are referred to herein as recombinant expression vectors or simply, expression vectors. Preferably, the vector carries marker cassettes, more preferably, GFP expression cassettes, so that the course of transduction, engrafting and tumor growth and remission may be observed. Preferably, the vector also carries a ubiquitous promoter to permit expression or up-regulation of oncogenes in all cell types of epithelium (i.e., stem cell and non-stem cell compartments).

As used herein, viral transduction refers to a general method of gene transfer. As embodied herein, viral transduction is used for establishing stable expression of genes in culture. Viral transduction and long-term expression of genes in cells, preferably cultured hepatocytes, is preferably accomplished using viral vectors.

After viral transduction the cells are preferably injected into the spleen of the recipient non-human animal, preferably a rodent and most preferably a mouse, that are preferably pretreated with a liver cell cycle inhibitor. Using this approach, the genetically modified or altered hepatocytes migrate via the portal vein into the recipient liver and engraft the organ. An additional proliferation stimulus to the liver can preferably be given after hepatocyte transplantation by serial administration of $CCl_4$.

Non-human animals harboring hepatocellular carcinomas of different genetic constellations produced by the altered hepatocytes can be characterized with regard to time to tumor onset and survival time. Tumors of different genetic constellations can also be histologically examined and classified by experienced pathologists.

As used herein, an altered hepatocyte refers to a change in the level of a gene and/or gene product with respect to any one of its measurable activities in a hepatocyte (e.g., the function which it performs and the way in which it does so, including chemical or structural differences and/or differences in binding or association with other factors). An altered hepatocyte may be effected by one or more structural changes to the nucleic acid or polypeptide sequence, a chemical modification, an altered association with itself or another cellular component or an altered subcellular localization. Preferably, an altered hepatocyte may have "activated" or "increased" expression of an oncogene, "repressed" or "decreased" expression of a tumor suppressor gene or both.

The increased expression of an oncogene refers to a produced level of transcription and/or translation of a nucleic acid or protein product encoded by an oncogenic sequence in a cell. Increased expression or up regulation of an oncogene can be non-regulated (i.e., a constitutive "on" signal) or regulated (i.e., the "on" signal is induced or repressed by another signal or molecule within the cell). An activated oncogene can result from, e.g., over expression of an encoding nucleic acid, an altered structure (e.g., primary amino acid changes or post-transcriptional modifications such as phosphorylation) which causes higher levels of activity, a modification which causes higher levels of activity through association with other molecules in the cell (e.g., attachment of a targeting domain) and the like.

The decreased expression of a tumor suppressor gene refers to an inhibited, inactivated or down regulated level of transcription and/or translation of a nucleic acid or protein product encoded by a tumor suppressor gene sequence in a cell. Reduced expression of a tumor suppressor gene can be non-regulated (i.e., a constitutive "off" signal) or regulated (i.e., the "off" signal is activated or repressed by another signal or molecule within the cell). As preferred herein, a repressed tumor suppressor gene can result from inhibited expression of an encoding nucleic acid (e.g., most preferably a short hairpin RNA using RNA interference approaches, see supra). Reduced expression of a tumor suppressor gene can also result from an altered structure (e.g., primary amino acid changes or post-transcriptional modifications such as phosphorylation) which causes reduced levels of activity, a modification which causes reduced levels of activity through association with other molecules in the cell (e.g., binding proteins which inhibit activity or sequestration) and the like.

A short hairpin RNA refers to a segment of RNA that is complementary with a portion of one or more target genes (i.e. complementary with one or more transcripts of one or more target genes). When a nucleic acid construct encoding a short hairpin RNA is introduced into a cell, the cell incurs partial or complete loss of expression of the target gene. In this way, a short hairpin RNA functions as a sequence specific expression inhibitor or modulator in transfected cells. The use of short hairpin RNAs facilitates the down-regulation of tumor suppressor genes and allows for analysis of hypomorphic alleles. The short hairpin RNAs that are useful in the invention can be produced using a wide variety of RNA interference ("RNAi") techniques that are well known in the art. The invention may be practiced using short hairpin RNAs that are synthetically produced as well as microRNA (miRNA) molecules that are found in nature and can be remodeled to function as synthetic silencing short hairpin RNAs. A preferred claim of the invention is the use of a short hairpin RNA that mediates inhibition of a oncogenic signal, preferably a tumor suppressor gene and thus apoptotic signaling in a cell. Preferably, the short hairpin RNAs are against cIAP1 and cIAP2.

Other methods of RNA interference may also be used in the practice of this invention. See, e.g., Scherer and Rossi, *Nature Biotechnology* 21:1457-65 (2003) for a review on sequence-specific mRNA knockdown of using antisense oligonucleotides, ribozymes, DNAzymes, RNAi and siRNAs. See also, International Patent Application PCT/US2003/030901 (Publication No. WO 2004/029219 A2), filed Sep. 29, 2003 and entitled "Cell-based RNA Interference and Related Methods and Compositions".

As used herein the term liver or hepatocellular cancer tumor refers to a group of cells which are committed to a hepatocellular lineage and which exhibit an altered growth phenotype. The term encompasses tumors that are associated with hepatocellular malignancy (i.e., HCC) as well as with pre-malignant conditions such as hepatoproliferative and hepatocellular hyperplasia and hepatocellular adenoma, which include proliferative lesions that are perceived to be secondary responses to degenerative changes in the liver.

The non-human animals of the invention are useful in the study of the impact of genotype on pathology or treatment response in vivo. Thus, the methods and models of the invention have implications for understanding disease progression in human liver carcinomas of specific genetic origin. The invention is also useful for determining the efficacy of a therapy in treating liver cancer. For example, a potential therapy may be administered to a non-human animal, produced by the methods embodied herein, and the non-human animal monitored for liver tumor formation, growth, progression or remission. Often, increased time to tumor formation or growth indicates sensitivity of the tumor to the therapy.

Genomic analysis of human carcinomas can be performed by gene expression profiling, e.g., ROMA. Such analysis in the tumors produced according to the invention has revealed a low signal to noise ratio of profiled genes, suggesting that the majority of detected genetic alterations in human tumors (having a high signal to noise ratio) may not be originally involved in tumor development but may be a by-product of tumor development. The analysis of mouse tumors produced according to the invention has shown that these tumors have a low signal to noise ratio, suggesting that a higher proportion of the identified lesions are specifically involved in tumor initiation/progression. Thus, the analysis of mouse tumors by gene expression profiling can serve as a filter for the "noisy" human tumors. Results obtained from mouse profiling using ROMA can be aligned with ROMA data obtained from human hepatocellular carcinomas. Overlapping amplifications or deletions then can be prioritized for further evaluation.

Tumors showing specific amplifications of candidate oncogenes in gene expression profiles can be outgrown in culture. Using stable RNAi, efficient knockdown of these genes can be achieved. Tumor cells with stable knockdown of a previously amplified gene can be re-transplanted into the mouse model of the current invention. Using this approach new therapeutic targets for hepatocellular carcinoma and related carcinomas can be obtained and the specific consequences of knocking down an amplified gene with regard to tumor growth or metastases can be studied. Drug therapies that specifically inhibit the identified targets can be developed.

Therapies that may be tested and evaluated in the methods and models of this invention include both general and targeted therapies. As used herein, a general therapy can be, for example, a pharmaceutical or chemical with physiological effects, such as pharmaceuticals that have been used in chemotherapy for cancer. Chemotherapeutic agents inhibit proliferation of tumor cells, and generally interfere with DNA replication or cellular metabolism. See, e.g., *The McGraw-Hill Dictionary of Chemical Terms* (Parker, S., Ed., McGraw-Hill, San Francisco (1985)). Chemotherapeutic agents may or may not have been characterized for their target of action in cells. However, this invention and its methods and models allow evaluation of such therapies for defined genetic alterations.

A targeted therapy refers to a therapy that directly interferes with a specific gene Preferably, a targeted therapy directly interferes with the expression of a gene involved in liver cancer. The effectiveness of a targeted therapy can be determined by the ability of the therapy to inhibit an oncogene or activate a tumor suppressor gene.

Figure 2A:
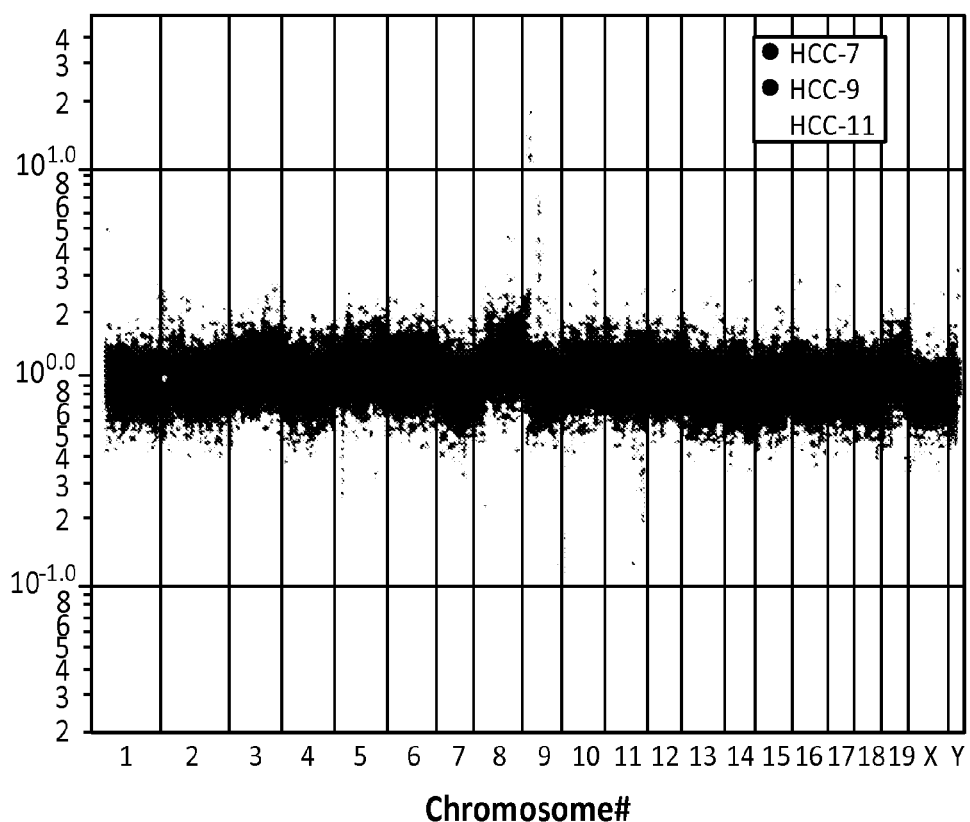
FIG. 2: Genome-wide analysis of copy number alterations in mouse hepatocellular carcinoma (HCC). DNA from tumors and subjected to 85K ROMA. Plotted is the normalized log-ratio for each oligo probe and ordered according to genome position, derived from the May 2004 freeze of the draft mouse genome sequence (http://www.genome.ucsc.edu). (a) Representative profiles of 3 mouse HCCs. HCC-7 and HCC-9, both derived from p53−/−; c-myc hepatoblasts, contain an amplification on chromosome 9. HCC-11, derived from p53−/−; Akt hepatoblasts, does not. (b) Expanded view of chromosome 9 reveals a 1.9 Mb amplicon (HCC-9) and a 1.2 Mb (HCC-7) amplicon containing the c-IAP-1 and c-IAP-2 genes. (c) Quantitative PCR with primers specific for the c-IAP-1 gene revealed higher copy numbers for 2 additional p53−/−; c-myc HCCs (HCC-13 and HCC-14), while non-c-myc tumors (HCC-15 and HCC-17) have a normal IAP copy number. (d) Summary of c-IAP-1/2 amplification relative to genetic background. (e) c-IAP-1 and c-IAP-2 mRNA levels are elevated in tumors containing the amplicon. Levels of IAP RNA relative to actin were determined by quantitative RT-PCR and normalized to normal liver.
Figure 2B:
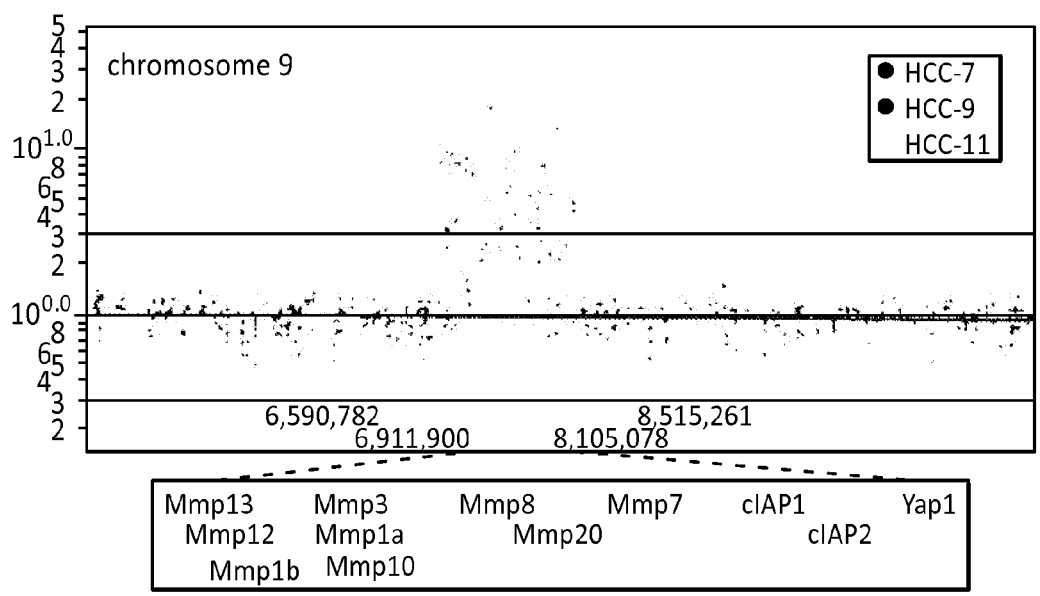
Figure 3A:
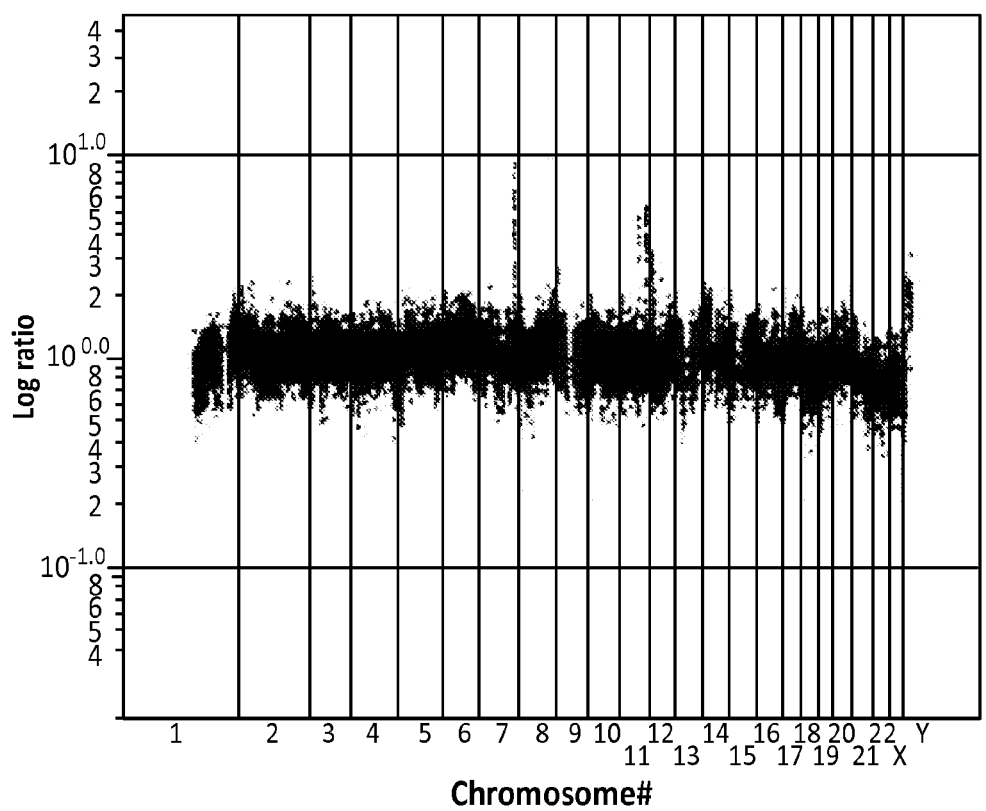
FIG. 3: Genome-wide analysis of a human hepatocellular carcinoma analyzed with 36K ROMA. (a) The three peaks indicate amplicons containing the MET-oncogene, Cyclin D and c-IAP1/2 (left to right). (b) Expanded view of chromosome 11 showing the amplicons containing cyclin D and c-IAP1/2. (c) 1/25 human HCCs have elevated c-IAP-1 and c-IAP-2 gene copy numbers as determined by quantitative PCR off genomic DNA. (d) c-IAP-1 and/or c-LAP-2 mRNA levels are elevated in 4/25 HCCs as determined by quantitative RT-PCR.
Figure 3B:
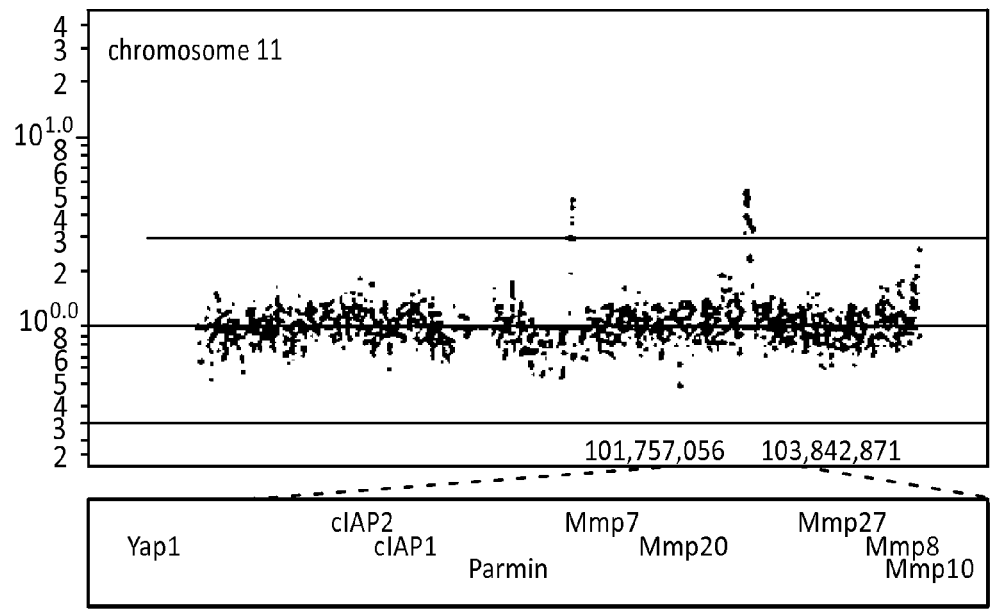
Figure 3C:
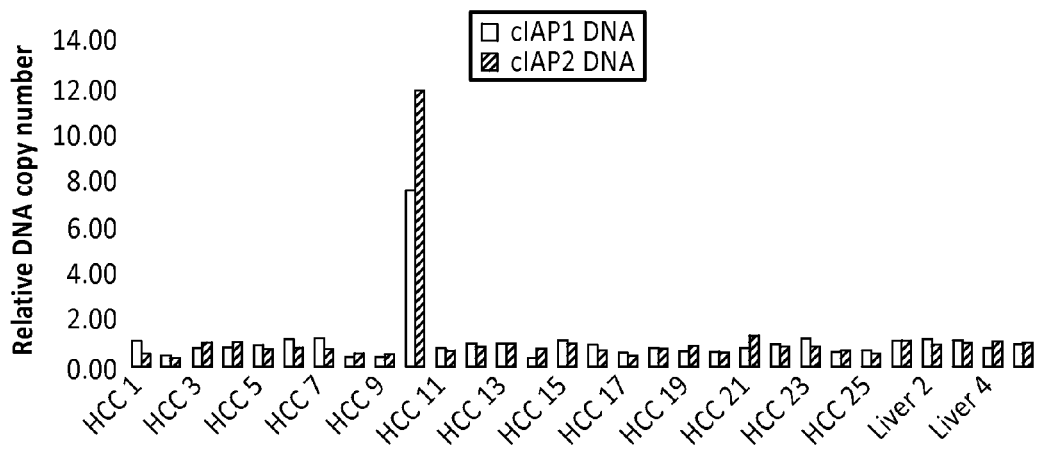
Figure 3D:
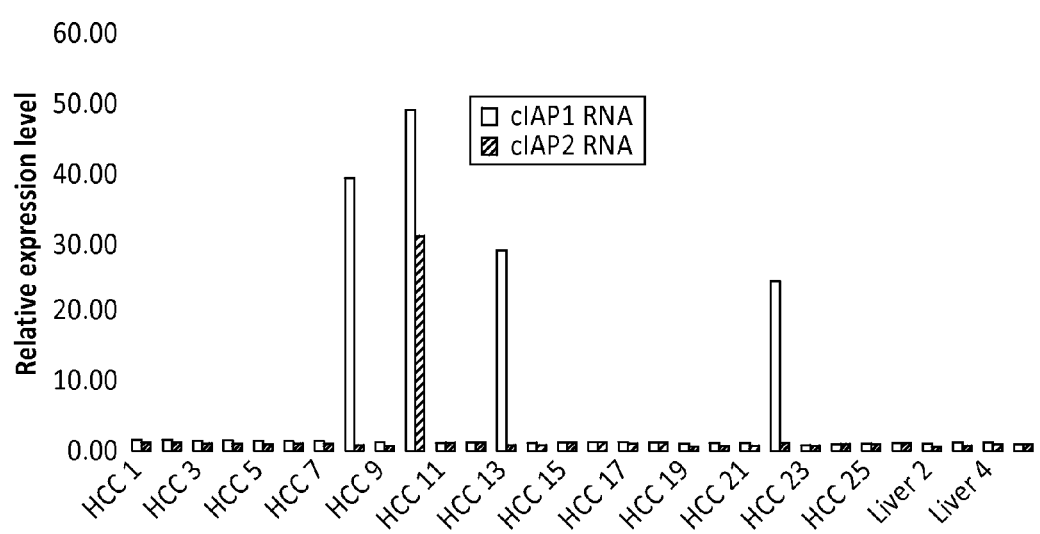
Figure 4A:
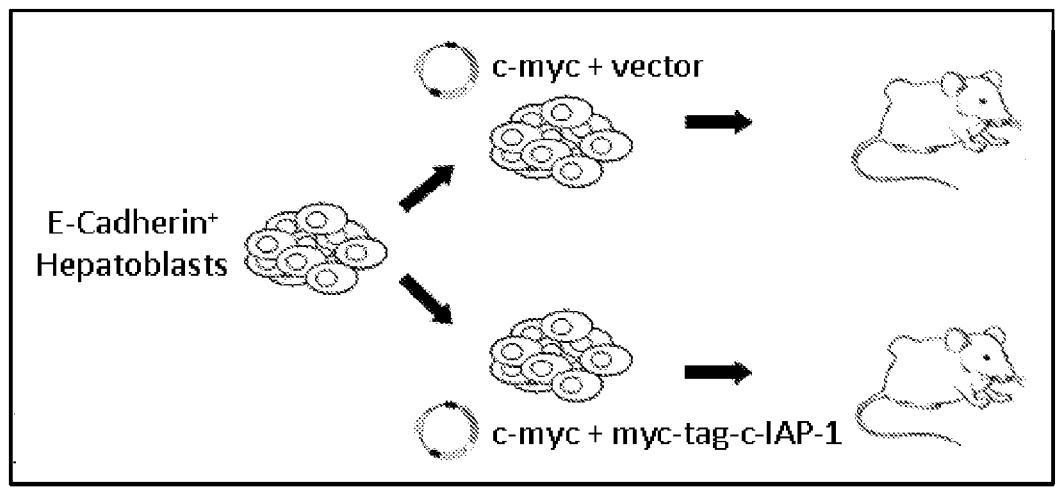
FIG. 4: c-IAP-1 overexpression accelerates tumor growth. (a) Schema of the approach to investigate the oncogenic properties of c-IAP-1 in vivo. E-Cadherin+hepatoblasts were either double-infected with c-myc+control vector or c-myc+myc-tag-c-IAP-1. 10×106 cells were subcutaneously injected into irradiated NCR nu/nu mice. (b) Overexpression of c-IAP-1 in primary liver cells was confirmed by western blot analysis using an α-myc-tag antibody. (c) Four out of six c-myc+c-IAP-1 double infected tumors show accelerated tumor growth compared to c-myc+vector. Tumor size was assessed by caliper measurement of subcutaneously growing tumors. (d) All tumors showing accelerated growth contain the c-LAP-1 provirus as assayed by PCR. All analyzed tumors contain c-myc-provirus DNA. (e) Representative example of an accelerated c-IAP1+c-myc double infected tumor (left) compared to a c-myc+vector infected tumor (right). External GFP-imaging of the tumors (bottom) was performed at the same time post-injection.
Figure 4B:
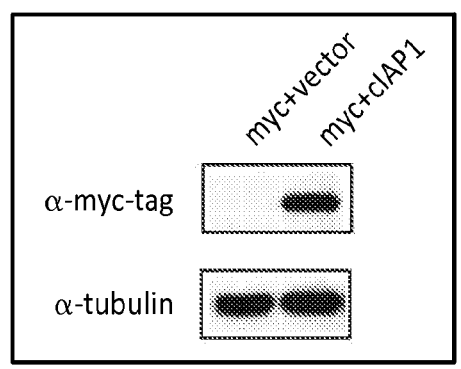
Figure 4C:
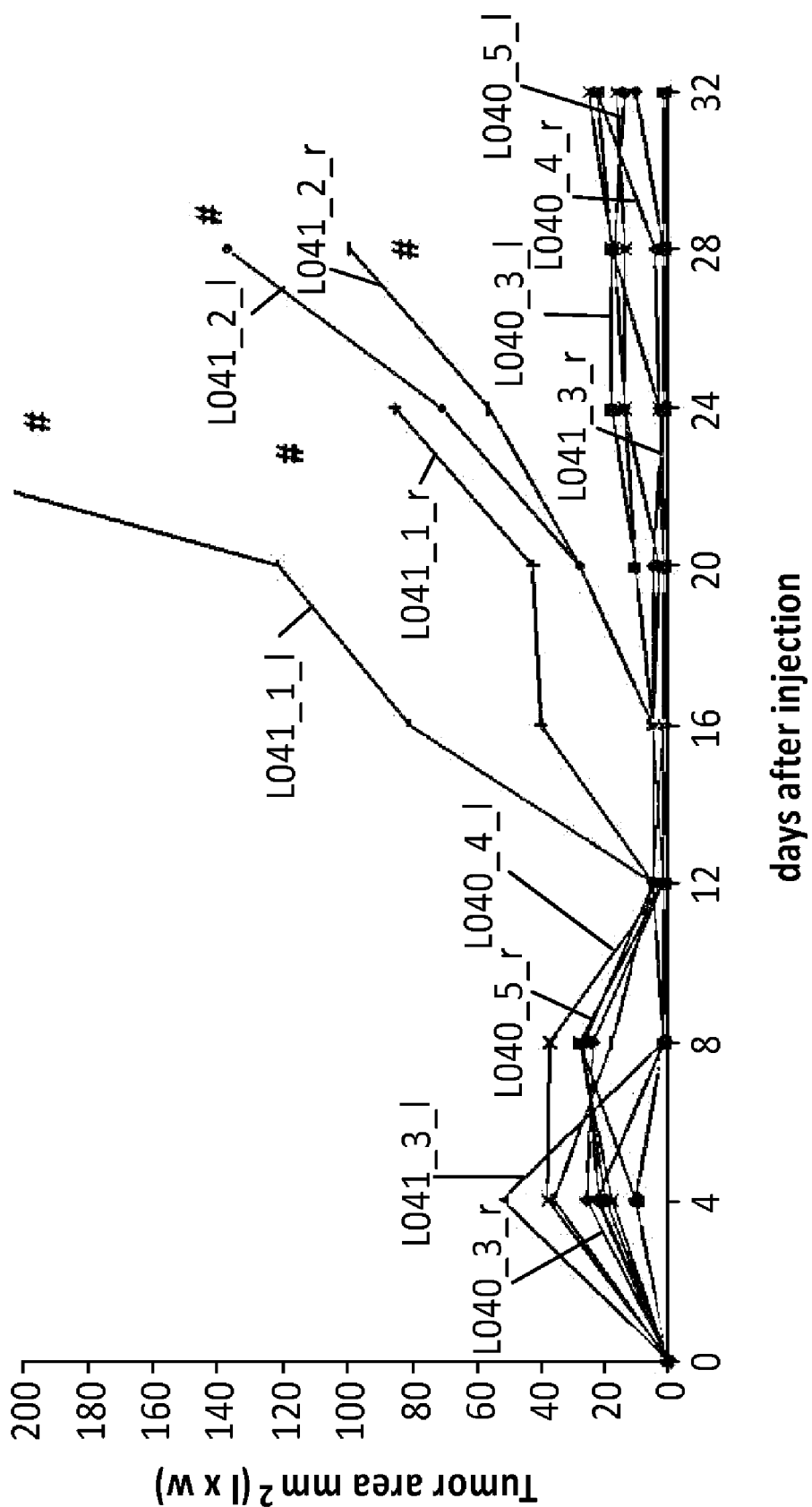
Figure 4D:
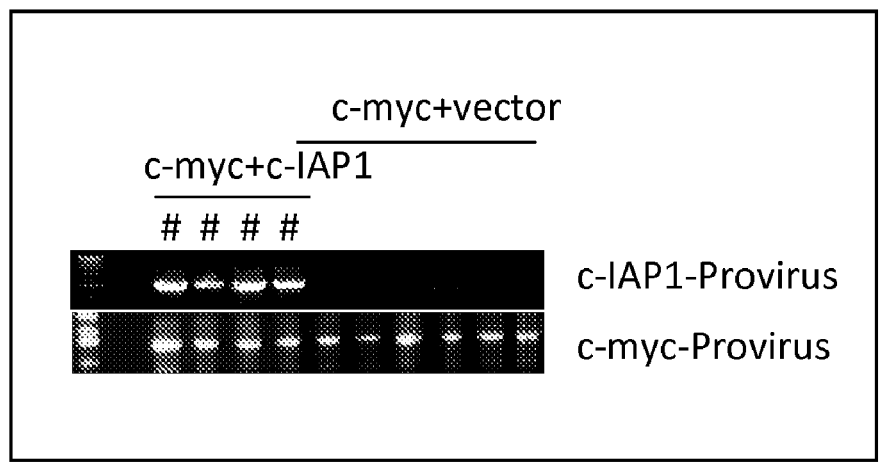
Figure 4E:
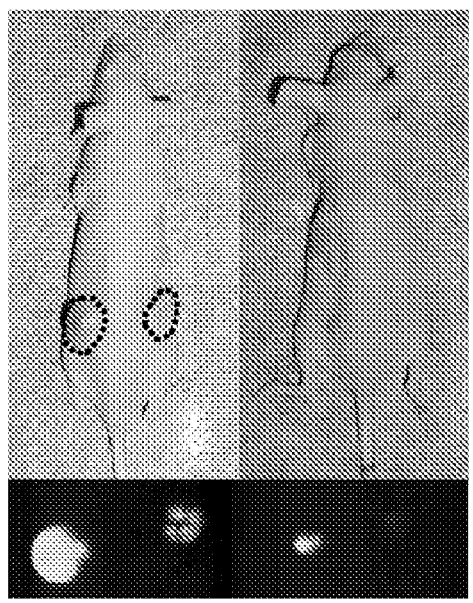
Figure 5C:
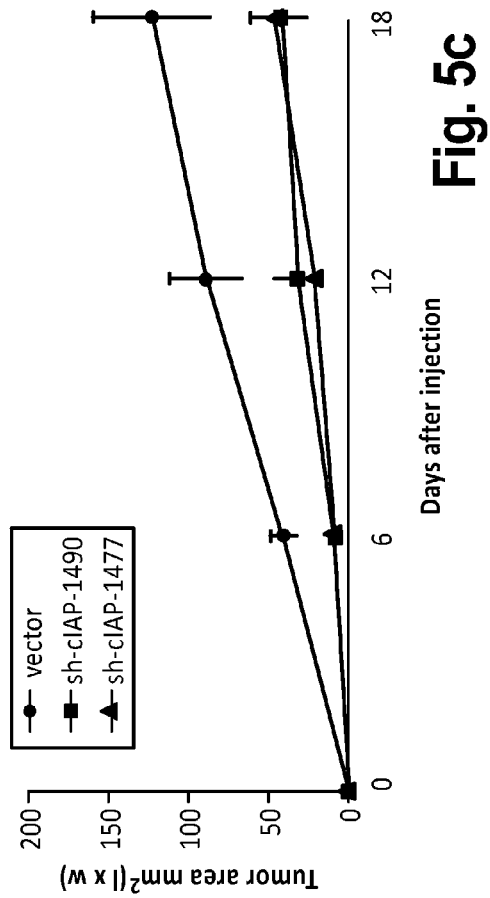
FIG. 5: Suppression of c-IAP-1 in HCC cells slows tumor growth. (a) Schema for testing knock-down of c-IAP-1 expression in vivo. Cells from tumors containing the c-IAP1/2 amplicon are outgrown briefly and infected either with a retrovirus expressing a short hairpin (miR30 design) RNA directed against c-IAP-1 or with control vector. After puromycin-selection, cells were injected subcutaneously into NCR nu/nu mice. (b) One out of four short hairpins directed against c-IAP-1 suppresses c-IAP-1 expression. NIH 3T3 cells were transiently transfected with pcDNA-myc tag-c-LAP-1 together with the respective hairpin. Western blot was performed using an α-myc-tag antibody. c-IAP-1-hairpin "1477" shows >95% knockdown (c) Tumors with stable RNAi mediated knockdown of c-IAP-1 show decelerated tumor growth compared to control vector infected tumors. Growth of subcutaneous tumors was assessed by caliper measurement. (d) Representative example of a slower growing tumor with c-IAP-1 knockdown (right) compared to a control vector infected tumor. External GFP-imaging of the tumors (top panel) was done at the same time post-injection.
Figure 5D:
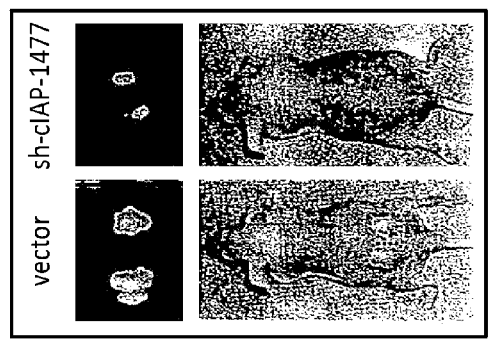
Figure 5A:
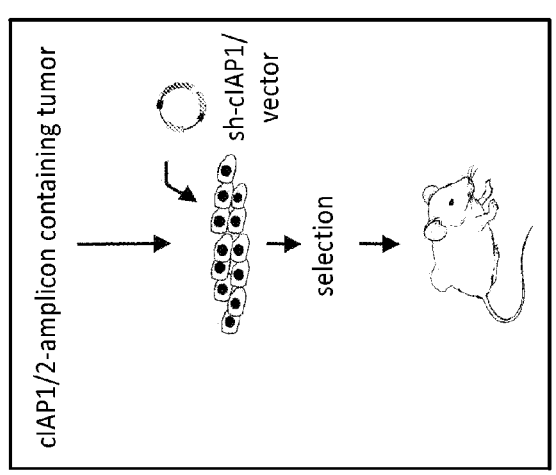
Figure 5B:
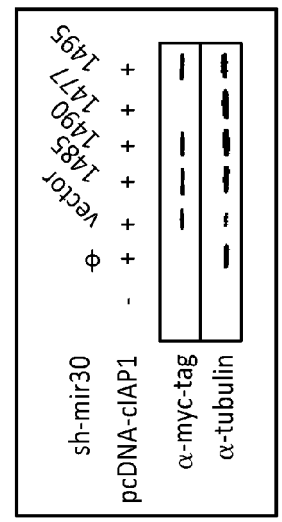
Figure 6A:
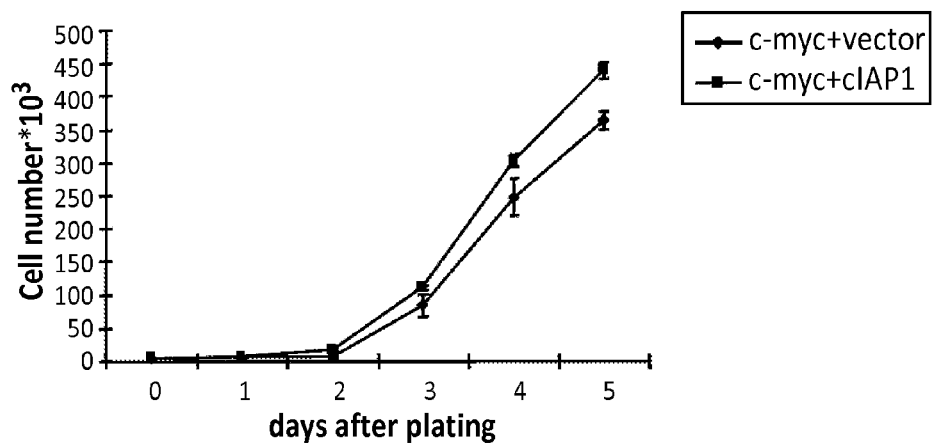
FIG. 6: Influence of c-IAP-1 overexpression on proliferation and apoptosis in cultured hepatoblasts. (a) ECadherin+ hepatoblasts were infected with a neomycin selectable retrovirus overexpressing c-myc and a puromycin selectable retrovirus overexpressing c-IAP-1 or control vector. After neomycin/puromycin selection cells were plated at 4.5×103 cells/cm2 and growth rate was assessed by daily counting of the total cell number. c-IAP-1 overexpressing cells have a slight growth advantage. (b) c-myc+c-IAP-1 or c-myc+vector double infected
Figure 6B:
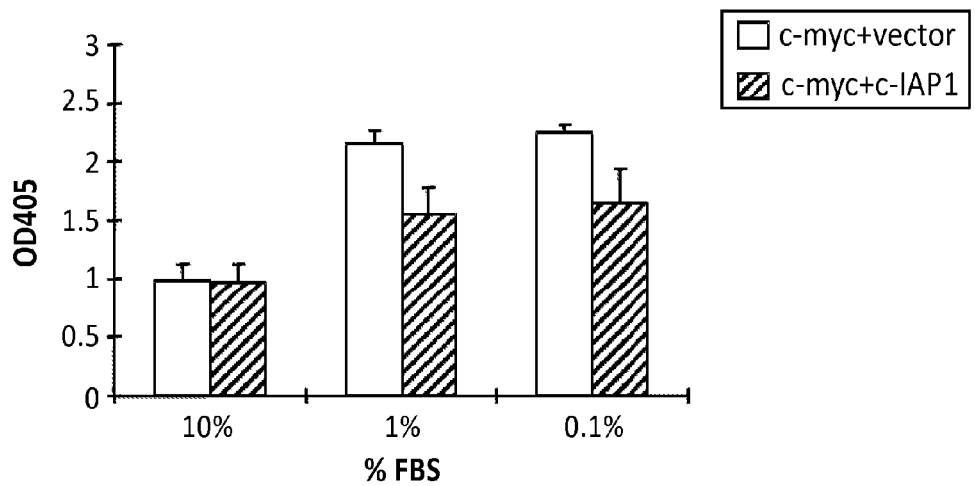
Figure 6C:
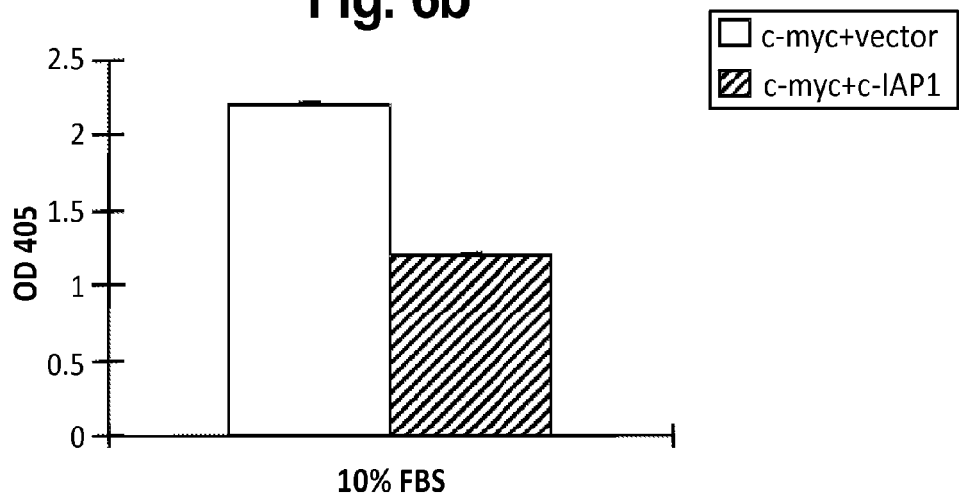
Figure 7:
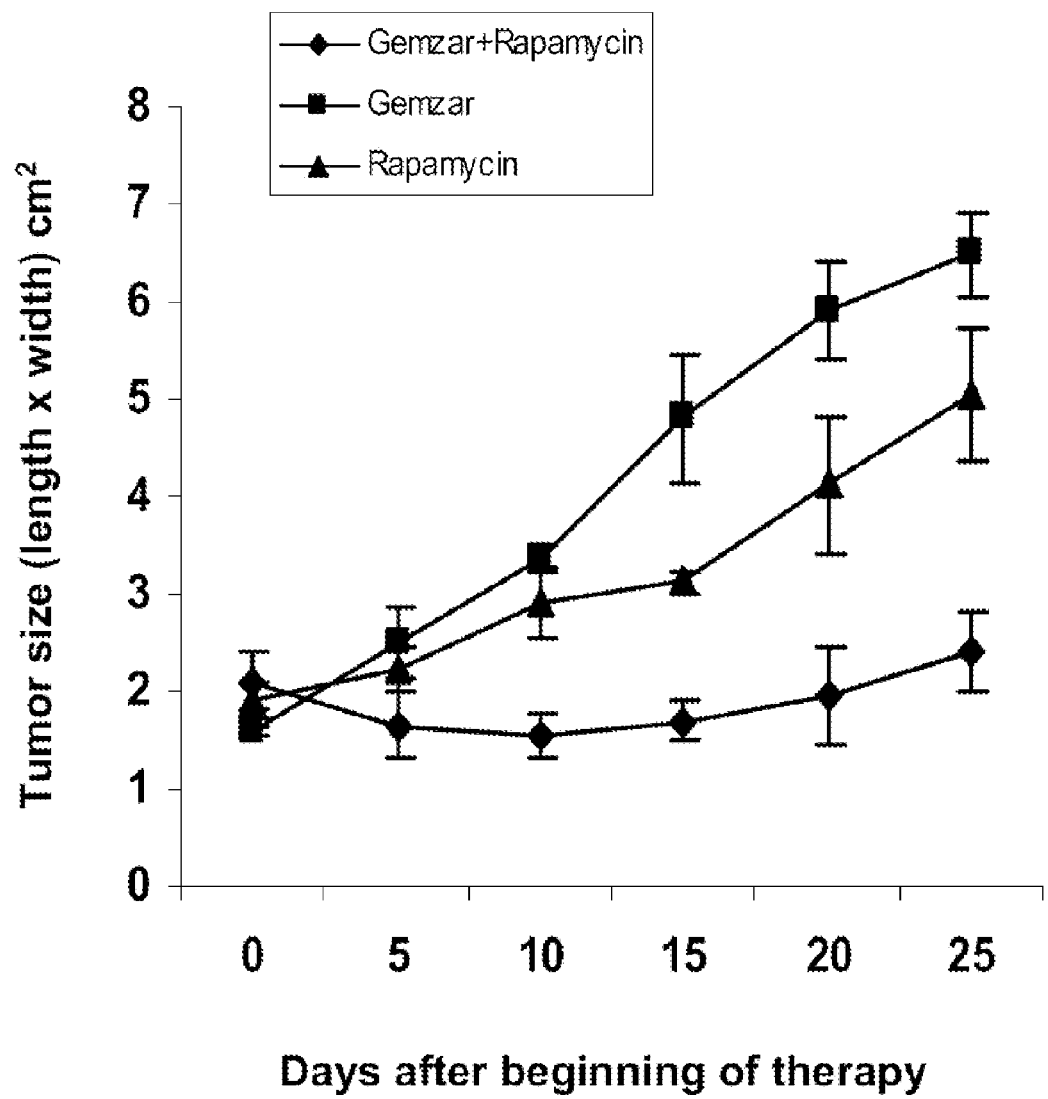
FIG. 7: An example of subcutaneous liver cancer model of this invention on the genetic constellation p53−/−+Akt-overexpression and its uses in evaluating tumor therapy. Akt is an apoptotic regulator that is activated in many cancers and may promote drug resistance in vitro (Mayo et al., "PTEN protects p53 from Mdm2 and sensitizes cancer cells to chemotherapy," *J. Biol. Chem.* 277: 5484-5489 (2002)). The graph shows that the tumor's intrinsic chemoresistance against the cancer drug Gemcitabine® (brand name "Gemzar" in the Figure) can be reversed by application of a downstream effector of Akt, the mTOR (mammalian target of rapamycin) inhibitor Rapamycin.

Most preferably, the therapies are used and evaluated in combination. For example, as shown in FIG. 7, upon onset of liver cancer tumors, animals can be treated with Gemcitabine ("Gemzar"), a chemotherapeutic agent that is an antimetabolite that functions as a mild chemotherapeutic to interfere with the growth of cancer cells. As shown in FIG. 7, it has virtually no effect on tumor growth of the particular tumor tested in FIG. 7. The tumor embodied in FIG. 2 can also be treated with Rapamycin, a targeted therapy that inhibits the mammalian target of rapamycin (mTOR). It has some effect on the tumor growth. In combination, however, as depicted in FIG. 7, the two therapies control tumor growth.

The size and growth of tumors after therapy can be monitored by a wide variety of ways known in the art. Preferably, whole body fluorescence imaging is used because the preferred viral vectors of this invention carry a GFP expression cassette. See, e.g, Schmitt et al., "Dissecting p53 tumor suppressor functions in vivo," *Cancer Cell* 1:289-98 (2002). Tumors can also be examined histologically. Paraffin embedded tumor sections can be used to perform immunohistochemistry for cytokeratins and ki-67 as well as TUNEL-staining. The apoptotic rate of hepatocytes can be analyzed by TUNEL assay according to published protocols. Di Cristofano et al., "Pten and p27KIP1 cooperate in prostate cancer tumor suppression in the mouse," *Nature Genetics*, 27:222-224 (2001).

Beyond having important implications for understanding liver cancer, the evaluations and observations made possible by the methods and models of this invention provide insight into the utility of targeted approaches in cancer therapy.

Throughout this specification and claims, the word "comprise" or variations such as "comprises" or "comprising", will be understood to imply the inclusion of a stated integer or group of integers but not the exclusion of any other integer or group of integers.

II. In Vivo RNAi Screening to Identity New Genes Associated with Liver Cancer

RNAi has been widely used to silence or inhibit the expression of a target gene. RNAi is a sequence-specific post-transcriptional gene silencing mechanism triggered by dsRNA. It causes degradation of mRNAs homologous in sequence to the dsRNA. The mediators of the degradation are 21-23-nucleotide siRNAs generated by cleavage of longer dsRNAs by DICER, a ribonuclease III-like protein. Molecules of siRNA typically have 2-3-nucleotide 3' overhanging ends resembling the RNAse III processing products of long dsRNAs that normally initiate RNAi. When introduced into a cell, they assemble an endonuclease complex (RISC), which then guides target mRNA cleavage. As a consequence of degradation of the targeted mRNA, cells illustrating the specific phenotype associated with the suppression of the corresponding protein product are obtained. If the protein that is knocked down possesses an activity that attenuates cell growth, such knock down will result in unbridled growth of the cells.

The small size of siRNAs, compared with traditional antisense molecules, prevents activation of the dsRNA-inducible interferon system present in mammalian cells. This helps avoid the nonspecific phenotypes normally produced by dsRNA larger than 30 base pairs in somatic cells. See, e.g., Elbashir et al., 2002, *Methods Enzymol.* 26: 199-213; McManus and Sharp, 2002, *Nature Reviews* 3: 737-747; Hannon, 2002, *Nature* 418: 244-251; Brummelkamp et al., 2002, *Science* 296: 550-553; Tuschl, 2002, *Nature Biotechnology*

20: 446-448; U.S. Application US2002/0086356 A1; WO 99/32619; WO 01/36646; and WO 01/68836.

RNAi is also possible via gene expression cassettes expressing shRNA or shRNAmir. shRNA and shRNAmir are modeled on intermediate constructs of miRNA. Both are cleaved by DICER to form siRNAs and interact with the RISC complex in the same manner as siRNA.

Libraries. In one embodiment, RNAi molecules useful to practice methods of the invention comprise a library that include RNAi molecules targeting potential tumor suppressor genes. Examples of known tumor suppressors are p53, BRCA1, BRCA2, APC, p16$^{INK4a}$, PTEN, NF1, NF2, and RB1. Additionally, potential tumor suppressor genes may be identified, for example, by identifying genomic deletions in a cancer genome. In particular, genes located within a recurrent genomic deletions from various cancer samples may be considered as potential candidate tumor suppressor genes.

shRNA and miRNA. When a nucleic acid construct encoding a short hairpin RNA is introduced into a cell, the cell incurs partial or complete loss of expression of the target gene. In this way, a short hairpin RNA functions as a sequence-specific expression inhibitor or modulator in transfected cells. The use of short hairpin RNAs facilitates the down-regulation of the target gene and allows for analysis of hypomorphic alleles. Short hairpin RNAs useful in the invention can be produced using a wide variety of well known RNAi techniques. The invention may be practiced using short hairpin RNAs that are synthetically produced as well as microRNA (miRNA) molecules that are found in nature and can be remodeled to function as synthetic silencing short hairpin RNAs. DNA vectors that express perfect complementary short hairpin RNAs (shRNAs or shRNAmirs) are commonly used to generate functional siRNAs.

In certain embodiments, the siRNA useful to practice the invention or a precursor molecule thereof, may be a shRNA or a shRNAmir, both modeled on miRNA intermediates. shRNA and shRNAmir are sequences of RNA that make tight hairpin turns (stem-loop structure) that can be used to silence gene expression. miRNAs are single-stranded RNA molecules of about 21-23 nucleotides and are part of an endogenous RNAi system. miRNAs are usually processed from two RNA intermediates: a primary miRNA (pri-miRNA) transcript and a precursor miRNA (pre-miRNA). The precursor transcripts are converted into short stem-loop structures, and then to functional miRNAs. Many miRNA intermediates can be used as models for shRNA or shRNAmir, including without limitation a miRNA comprising a backbone design of miR-15a, -16, -19b, -20, -23a, -27b, -29a, -30b, -30c, -104, -132s, -181, -191, -223. See US 2005-0075492 A1 (incorporated herein by reference).

MicroRNAs (miRNAs) are endogenously encoded RNAs that are about 22-nucleotide-long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Importantly, miRNAs are expressed in a highly tissue-specific or developmentally regulated manner, and this regulation is likely key to their predicted roles in eukaryotic development and differentiation. Analysis of the endogenous role of miR-NAs will be facilitated by techniques that allow the regulated over-expression or inappropriate expression of authentic miRNAs in vivo. Their ability to regulate the expression of siRNAs will greatly increase their utility both in cultured cells and in vivo. Thus, one can design and express artificial miR-NAs based on the features of existing miRNA genes, such as the gene encoding the human miR-30 miRNA. These miR30-based shRNAs and shRNAmirshave complex folds, and, compared with simpler stem/loop style shRNAs, are more potent at inhibiting gene expression in transient assays. Moreover, they are associated with less toxic effects in cells.

miRNAs are first transcribed as part of a long, largely single-stranded primary transcript (pri-miRNA) Lee et al., 2002, *EMBO J.* 21: 4663-4670). This pri-miRNA transcript is generally, and possibly invariably, synthesized by RNA polymerase II and therefore is normally polyadenylated and may be spliced. It contains an ~80-nt hairpin structure that encodes the mature ~22-nt miRNA as part of one arm of the stem. In animal cells, this primary transcript is cleaved by a nuclear RNaseIII-type enzyme called Drosha (Lee et al., 2003, *Nature* 425: 415-419) to liberate a hairpin miRNA precursor, or pre-miRNA, of ~65 nt. This pre-miRNA is then exported to the cytoplasm by exportin-5 and the GTP-bound form of the Ran cofactor (Yi et al., 2003, *Genes & Development* 17: 3011-3016). Once in the cytoplasm, the pre-miRNA is further processed by Dicer, another RNaseIII enzyme, to produce a duplex of ~22 bp that is structurally identical to an siRNA duplex (Hutvagner et al., 2001, *Science* 293: 834-838). The binding of protein components of the RNA-induced silencing complex (RISC), or RISC cofactors, to the duplex results in incorporation of the mature, single-stranded miRNA into a RISC or RISC-like protein complex, while the other strand of the duplex is degraded (Bartel, 2004, *Cell* 116: 281-297).

The miR-30 architecture can be used to express miRNAs or siRNAs from RNA polymerase II promoter-based expression plasmids. See also Zeng et al., 2005, *Methods Enzymol.* 392: 371-380 (incorporated herein by reference).

In some instances the precursor miRNA molecule may include more than one stem-loop structure. The multiple stem-loop structures may be linked to one another through a linker, such as, for example, a nucleic acid linker, a miRNA flanking sequence, other molecule, or some combination thereof.

In certain embodiments, useful interfering RNAs can be designed with a number of software programs, e.g., the OligoEngine siRNA design tool available at www.oligoengine.com. The siRNAs of this invention may be about, e.g., 19-29 base pairs in length for the double-stranded portion. In some embodiments, the siRNAs are shRNAs having a stem of about 19-29 base pairs and a nucleotide loop of about 4-34 bases. Preferred siRNAs are highly specific for a region of the target gene and may comprise a 19-29 base pair fragment of the mRNA of a target gene, with at least one, but preferably two or three, ase airbp mismatch with a nontarget gene-related sequence. In some embodiments, the preferred siRNAs do not bind to RNAs having more than three base pair mismatches with the target region.

In certain embodiments, artificial miRNA constructs based on miR-30 (microRNA 30) may be used to express precursor miRNA/shRNA. For example, Silva et al., 2005, *Nature Genetics* 37: 1281-88, have described extensive libraries of pri-miR-30-based retroviral expression vectors that can be used to down-regulate almost all known human (at least 28,000) and mouse (at least 25,000) genes (see RNAi Codex, a single database that curates publicly available RNAi resources, and provides the most complete access to this growing resource, allowing investigators to see not only released clones but also those that are soon to be released, available at http://codex.cshl.edu). Although such libraries are driven by RNA polymerase III promoters, they can be easily converted to the subject RNA polymerase II-driven promoters (see the Methods section in Dickins et al., 2005, *Nature Genetics* 37: 1289-95; also see page 1284 in Silva et al., 2005 supra).

In certain embodiments, the subject precursor miRNA cassette may be inserted within a gene encoded by the subject vector. For example, the subject precursor miRNA coding sequence may be inserted within an intron, the 5'- or 3'-UTR of a reporter gene, etc.

Other methods of RNAi may also be used in the practice of this invention. See, e.g., Scherer and Rossi, 2003, *Nature Biotechnology* 21: 1457-65 for a review on sequence-specific mRNA knockdown using antisense oligonucleotides, ribozymes, DNAzymes. See also, International Patent Application PCT/US2003/030901 (Publication No. WO 2004-029219 A2), filed Sep. 29, 2003 and entitled "Cell-based RNA Interference and Related Methods and Compositions." See also Fewell et al. supra, for a description of inducible shRNA, in which the vector does not express the shRNA unless a specific reagent is added. Several studies investigating the function of essential genes using RNAi rely on inducible shRNA. For example, shRNAmir constructs can be created based on a tetracycline-responsive promotor system, such that shRNA expression is regulated by changing doxycycline levels.

Vector. In an embodiment of the present invention, a library of RNAi molecules are introduced into a plurality of hepatocytes, using a vector known in the art. In certain embodiments, the vector is a viral vector. Exemplary viral vectors include adenoviral vectors, lentiviral vectors, or retroviral vectors. Many established viral vectors may be used to transfect foreign constructs into cells. The definition section below provides more details regarding the use of such vectors.

To facilitate the monitoring of the target gene knockdown, and the formation and progression of the cancer, cells harboring the RNAi-expressing construct may additionally comprise a marker construct, such as a fluorescent marker construct. The marker construct may express a marker, such as green fluorescent protein (GFP), enhanced green fluorescent protein (EGFP), Renilla Reniformis green fluorescent protein, GFPmut2, GFPuv4, yellow fluorescent protein (YFP), enhanced yellow fluorescent protein (EYFP), cyan fluorescent protein (CFP), enhanced cyan fluorescent protein (ECFP), blue fluorescent protein (BFP), enhanced blue fluorescent protein (EBFP), citrine and red fluorescent protein from discosoma (dsRED). Other suitable detectable markers include chloramphenicol acetyltransferase (CAT), luciferase lacZ (β-galactosidase), and alkaline phosphatase. The marker gene may be separately introduced into the cell harboring the shRNA construct (e.g., co-transfected, etc.). Alternatively, the marker gene may be linked to the shRNA construct, and the marker gene expression may be controlled by a separate translation unit under an IRES (internal ribosomal entry site). In a preferred embodiment, the marker is a green fluorescent protein (GFP).

To facilitate the quantification of specific RNAi molecules in a complex population of cells infected with an entire library of RNAi molecules, each RNAi construct may additionally comprise a barcode. A barcode is a unique nucleotide sequence (generally 19-mer), linked to each shRNA. The barcode can be used to monitor the abundance of each shRNA via microarray hybridization (Fewell et al., supra). In a preferred embodiment, each shRNA construct also comprises a unique barcode. For more information on the use of barcodes in shRNA pooled analyses, see Bernards et al., 2006, *Nature Methods* 3: 701-706, and Chang et al., 2006, *Nature Methods* 3: 707-714.

Transfection. In certain embodiments, a plurality of hepatocytes are transfected with a library of RNAi molecules, wherein each RNAi molecule targets a gene whose down-regulation is potentially associated with tumorigenesis, and the transfected cells are transplanted into an animal model. If an RNAi construct inhibits the expression of a tumor suppressor gene, the animal model receiving the transfected hepatocyte(s) may develop liver cancer (sometimes in conjunction with down-regulation of another tumor suppressor gene, or with the over-expression of an oncogene). Preferably, the liver cancer is recognizable by fluorescence or other detectable markers. From the tumors that arise, genomic DNA may be isolated, and the integrated hairpins may be amplified using polymerase chain reaction, cloned back into a vector, and then identified by sequencing.

Various methods may be used to determine the growth or viability of recipient cells expressing an RNAi-expressing construct in vitro. Such assays may be conducted using commercially available assay kits or methods well known to one or ordinary skill in the art. For example, cell viability can be determined by MTT assay or WST assay. The effect of the target gene knockdown can also be determined using cellular proliferation assays or cellular apoptosis/necrosis assays. In vitro cellular proliferation assays can be performed by determining the amount of cells in a culture over time. Cell numbers may be evaluated using standard techniques. Cellular apoptosis can be measured, for example, using a commercial apoptosis assay kit such as VYBRANT Apoptosis Assay Kit #3 (Molecular Probes). Cells can also be stained with P1 or DAP1 to detect apoptotic nuclei.

In certain embodiments, recipient cells expressing an RNAi construct (e.g., a shRNA) against a target gene are sorted based on a selectable marker whose expression substantially matches the expression of the RNAi molecule. In one exemplary embodiment, the selectable marker is fluorescence-based. In one exemplary embodiment, the selectable marker is GFP. In one embodiment, cells harboring the selectable marker are sorted using fluorescence-activated cell sorting (FACS). FACS is a powerful system which not only quantifies the fluorescent signal but also separates the cells that contain preselected characteristics (such as fluorescence intensity, size and viability) from a mixed population. Laser light is directed at individual cells as they flow through the FACS. A light scatter pattern is generated when the dense nuclear material of the cell interferes with the path of the laser beam.

Recipient cells expressing an RNAi construct (e.g., a shRNA) against a target gene may be subsequently transplanted into a recipient non-human animal. Alternatively, after transfection, the cells may be injected subcutaneously into a recipient non-human animal. The size and growth of tumors in the recipient, the survival of tumor-free recipients, and overall survival of the recipient may then be observed to investigate the effect of target-gene-knockdown in vivo. The size and growth of tumors may be examined by any of many known methods in the art, such as histological methods, immunohistochemical methods, TUNEL-staining, etc. In certain embodiments, the non-human animal is a mouse. In certain embodiments, the recipient animal is an immuno-compromised animal, such as a nude mouse.

Validation. Identified RNAi molecules may be validated by introduction into cells and assessment for knockdown, which may be done by immunoblotting or QPCR. If positive, the individual RNAi molecule may be further evaluated for their activities in animal models.

The candidate genes may be further assessed by in vitro or in vivo to ascertain the mechanism by which knockdown of these putative genes is tumorigenic. Such processes will elucidate whether the tumorigenesis is due to apoptotic defects or proliferation advantage. For example, response to growth factor withdrawal, DNA damage response to cytotoxic drugs, or activity of downstream targets would be further examined. In addition, deletions or mutations in human tumors can be explored and compared, using, for example, the ROMA database and human tumor samples.

III. Diagnosis and Treatment

Another aspect of the invention is a method of treating cancer comprising the steps of determining the status in cancerous tissue of one or more of the tumor suppressor genes described herein or identified by the screening method described herein, and if the expression or activity of any of the tumor suppressors is reduced in cancerous tissue in comparison to a control (e.g., a normal tissue), increasing the expression or activity of said tumor suppressor(s).

In one embodiment, the expression of a tumor suppressor is increased by introducing the tumor suppressor into the cancerous tissue. In a particular embodiment, the tumor suppressor protein or a physiologically active fragment, analog, or mutant thereof is administered. In another particular embodiment, the tumor suppressor gene or a fragment or mutant thereof that encodes a physiologically active polypeptide is introduced into the cancer tissue and expressed. In yet another embodiment, known upstream factors of an identified tumor suppressor is modulated to increase the tumor suppressor expression.

More specifically, an embodiment of the invention is a method for treating cancer comprising the steps of determining the status in cancerous tissue of one or more of the tumor suppressors described in Table 1 of Example 2. In one exemplary embodiment, the tumor suppressor is exportin 4 (Xpo4).

Another aspect of the invention is a method of treating cancer comprising: determining in cancerous tissue the expression of one or more tumor suppressor genes described herein or identified by the screening method described herein, the expression of which gene or genes are increased or decreased in comparison to a control (e.g., a normal tissue), and administering a therapeutic agent that is known to be effective in treating such cancers that are associated with the increased or decreased expression of such gene or genes. Alternatively, an aspect of the invention is a method of treating cancer comprising: determining in cancerous tissue the expression of one or more tumor suppressor genes described herein or identified by the screening method described herein, the expression of which gene or genes are decreased in comparison to a control (e.g., a normal tissue), and administering a therapeutic agent that is known not to antagonize the gene or genes identified herein.

More particularly, an embodiment of this aspect of the invention can be practiced using the tumor suppressor genes listed in the Table 1 of Example 2, or any other genes that are identified using the screening method described herein. More particularly, said tumor suppressor gene is Xpo4.

The expression level of a tumor suppressor gene be measured by mRNA level, protein level, activity level, or other quantity reflected in or derivable from the gene or protein expression data. For example, the mRNA level of a tumor suppressor gene may be measured using microarray technology that is well known in the art. Briefly, in a typical microarray experiment, a microarray is hybridized with differentially labeled RNA or DNA populations derived from two different samples. Most commonly, RNA (either total RNA or mRNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample is labeled with one fluor while cDNA derived from a second sample is labeled with the second fluor. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Alternatively, the mRNA level a tumor suppressor gene can be measured by polymerase chain reaction (PCR), a technique well known in the art. Briefly, one or more sets of oligonucleotide primers are annealed to a target sequence of interest, and the annealed primers are extended simultaneously to generate double-stranded (ds) copies of the target sequence. The primers are extended by a thermal-stable polymerase (McPherson, M. Ed. (1995) PCR 2: A Practical Approach, IRL Press at Oxford University Press, Oxford). The primers may be about 5-50 nucleotides in length. Real-time polymerase chain reaction, also called quantitative real time PCR (QRT-PCR) or kinetic polymerase chain reaction, may be highly useful to determine the expression level of a target gene because the technique can simultaneously quantify and amplify a specific part of a given polynucleotide. The QRT-PCR procedure follows the general pattern of polymerase chain reaction, but the DNA is quantified after each round of amplification. Two common methods of quantification are the use of fluorescent dyes that intercalate with double-strand DNA, and modified DNA oligonucleotide probes that fluoresce when hybridized with a complementary DNA. QRT-PCR can be combined with reverse transcription polymerase chain reaction to quantify low abundance messenger RNA (mRNA), enabling one to quantify relative gene expression at a particular time, or in a particular cell or tissue type.

The expression level of tumor suppressor may also be measured by protein level using any art-known method. Traditional methodologies for protein quantification include 2-D gel electrophoresis, mass spectrometry and antibody binding. Preferred methods for assaying target protein levels in a biological sample include antibody-based techniques, such as immunoblotting (western blotting), immunohistological assay, enzyme linked immunosorbent assay (ELISA), radioimmunoassay (RIA), or protein chips. Gel electrophoresis, immunoprecipitation and mass spectrometry may be carried out using standard techniques, for example, such as those described in Molecular Cloning A Laboratory Manual, $2^{nd}$ Ed., ed. by Sambrook, Fritsch and Maniatis (Cold Spring Harbor Laboratory Press: 1989), Harlow and Lane, Antibodies: A Laboratory Manual (1988 Cold Spring Harbor Laboratory), G. Suizdak, Mass Spectrometry for Biotechnology (Academic Press 1996), as well as other references cited herein.

The expression level of a tumor suppressor gene can also be measured by the activity level of the gene product using any art-known method.

In certain embodiments, it may be useful to compare the expression level of a tumor suppressor gene to a control. The control may be a measure of the expression of the tumor suppressor gene in a quantitative form (e.g., a number, ratio, percentage, graph, etc.) or a qualitative form (e.g., band intensity on a gel or blot, etc.). A variety of controls may be used. Levels of a tumor suppressor gene expression from a healthy individual may also be used as a control. Alternatively, the control may be expression levels of tumor suppressor gene from the individual being treated at a time prior to treatment or at a time period earlier during the course of treatment. Still other controls may include expression levels present in a database (e.g., a table, electronic database, spreadsheet, etc.).

IV. Pharmaceutical Composition

Yet another aspect of the invention is a pharmaceutical composition comprising a therapeutic agent for the treatment of cancer, which composition has specific utility to treat such cancer that has certain status regarding one or more tumor suppressors identified using the method described herein.

One embodiment of the invention is a pharmaceutical composition for the treatment of cancer in which the expression of said tumor suppressor is less than a control (e.g., in normal tissue), comprising a tumor suppressor protein or a physiologically active fragment, analog, or mutant thereof. Another particular embodiment is a pharmaceutical composition for the treatment of cancer in which the expression or activity of a tumor suppressor is less than a control (e.g., in normal tissue), comprising a tumor suppressor gene or a fragment or mutant thereof that encodes a physiologically active polypeptide is introduced into the cancer tissue and expressed. In yet another embodiment, a pharmaceutical composition comprises one or more therapeutic agents that modulate known upstream factors of an identified tumor suppressor to increase the tumor suppressor expression.

More particularly, an embodiment of this aspect of the invention can be practiced using the tumor suppressor genes listed in the Table 1 of Example 2, or any other genes that are identified using the screening method described herein. More particularly, said tumor suppressor gene is Xpo4.

EXEMPLIFICATIONS

The invention now being generally described, it will be more readily understood by reference to the following examples, which are included merely for purposes of illustration of certain aspects and embodiments of the present invention, and are not intended to limit the invention.

Example 1

Generation and Transplantation of Genetically Altered Liver Progenitor Cells

To determine whether genetically modified hepatoblasts could colonize recipient livers, a protocol was used that optimizes engraftment of transplanted cells in the recipient liver. Embryonic hepatoblasts express high E-Cadherin levels on their cell surface, which enables these cells to be isolated to high purity from fetal livers using magnetic bead selection. (Nitou et al. "Purification of fetal mouse hepatoblasts by magnetic beads coated with monoclonal anti-e-cadherin antibodies and their in vitro culture." *Exp. Cell Res.* 279, 330-343. (2002)). These cells express markers characteristic of bi-potential oval cells, the presumed cellular target of transformation in the adult rodent liver.

Animals were pretreated with retrorsine, an alkaloid that exerts a strong and persistent block of native hepatocyte proliferation and increases the competitive advantage of transplanted cells. Ten days after the last retrorsine treatment, $2\times10^6$ GFP-tagged E-Cadherin$^+$ liver progenitor cells were delivered to the liver by intrasplenic injection. Using this protocol, one week after injection approximately one percent of the host liver consisted of "seeded" GFP-positive cells that were embedded within the normal liver architecture (FIG. 1C).

Generation of Liver Carcinomas from Transplanted Liver Progenitor Cells

Hepatoblasts were isolated from p53−/− fetal livers and the cells were transduced with retroviruses co-expressing Myc (c-myc), activated Akt (Akt1), or oncogenic Ras (H-rasV12) (each of which affect signaling pathways altered in human liver cancer) and a GFP reporter. As above, these transduced cell populations were transplanted into retrorsine treated mice (see FIG. 1A). To further facilitate expansion of the transplanted cells, recipient mice were treated with CCl4 (Guo et al. "Liver repopulation after cell transplantation in mice treated with retrorsine and carbon tetrachloride." *Transplantation* 73, 1818-1824. (2002)) and monitored for signs of disease by abdominal palpation of the liver and whole body fluorescence imaging. Although p53−/− hepatoblasts were not tumorigenic in our system, each of the cell populations that also expressed an oncogene eventually produced GFP-positive tumors in the livers of recipient mice (FIG. 1C, top).

Figure 1C:
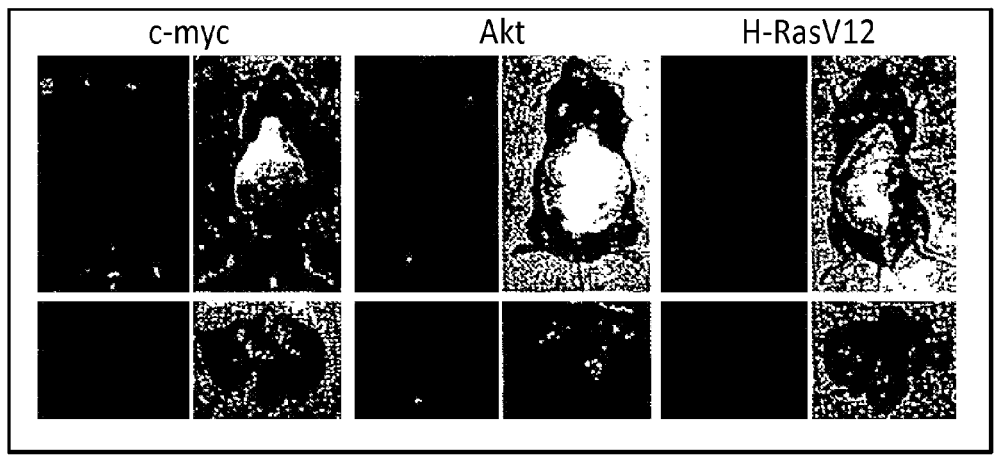
Figure 1D:
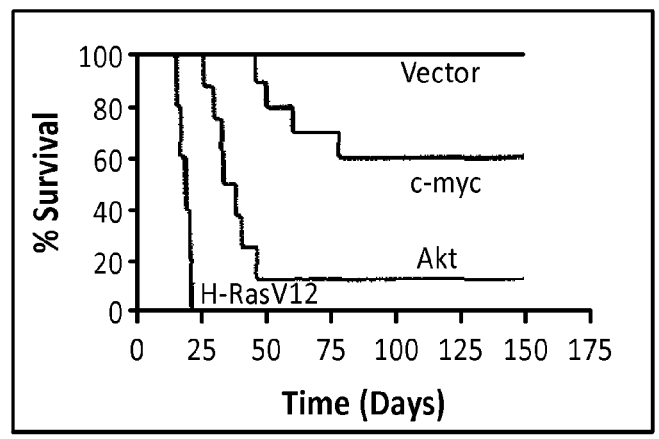
Figure 1E:

Gross pathological analysis of explanted livers revealed that Myc-expressing tumors differ significantly from those expressing Akt or Ras (FIG. 1C, bottom). First, Myc-expressing tumors grow primarily as unilocular tumors, whereas Akt- and Ras-derived tumors show aggressive, multilocular and infiltrative intrahepatic growth. Second, the innate tumorigenicity of p53−/− liver progenitor cells expressing Myc was significantly lower than those expressing Akt or Ras; thus, Akt or Ras trigger the development of liver carcinomas with an efficiency of nearly 100%, while Myc produced tumors at a penetrance around 40% (FIG. 1D). In most instances, GFP-positive cells derived from these tumors could be readily grown in culture, and subsequently formed secondary tumors upon sub-cutaneous injection into immunocompromised mice or direct intrahepatic injection into syngeneic recipients (data not shown).

Murine Liver Carcinomas Histopathologically Resemble Features of Human HCC

To determine whether the murine tumors produced from liver progenitors resemble human liver cancer, a panel of hematoxylin/eosin (H&E) stained sections derived from primary Myc-induced murine hepatomas were examined by an experienced liver pathologist. These tumors were classified as moderately well to poorly differentiated HCCs with a mostly solid, sometimes mixed solid/trabecular growth pattern. A smaller proportion of tumors revealed growth patterns resembling trabecular or pseudoglandular HCC (data not shown). All tumors examined stained positive for cytokeratin 8, confirming they were derived from the liver lineage. Furthermore, transplanted tumors retained their HCC histology when injected orthotopically into the liver, or subcutaneously into immunocompromised mice (data not shown). These findings confirm that ex vivo manipulated liver progenitor cells can produce tumors that recapitulate the histopathology of human HCC.

ROMA Identifies Spontaneous Mutations in a Subset of Murine Liver Carcinomas

Epithelial cancers require a series of genetic alterations during clonal evolution to an advanced disease. To molecularly characterize the murine HCCs described above, spontaneously acquired lesions in those cancers were analyzed using representational oligonucleotide microarray analysis (ROMA), a genome-wide scanning method capable of identifying copy number alterations in tumor cells at high resolution (Lucito et al. "Representational oligonucleotide microarray analysis: a high-resolution method to detect genome copy number variation." *Genome Res.* 13, 2291-2305. (2003)). Each human or mouse ROMA array consisted of 85K oligonucleotide probes designed to the UCSC April/2003 draft assembly of human genome and the UCSC February/2003 mouse genome, respectively, allowing genome scanning at a theoretical resolution of ~35 kb.

Figure 8A:
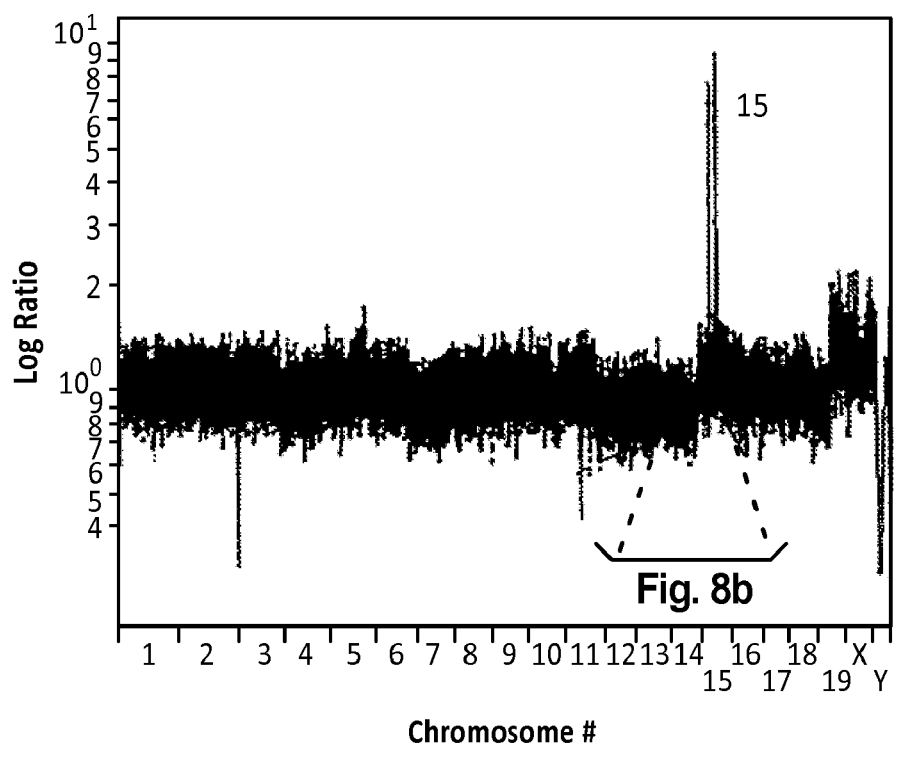
FIG. 8: ROMA identifies localized DNA amplifications in murine HCCs. (a) Genome-wide profile of a tumor derived from p53−/−; ras embryonic hepatoblasts reveals 2 amplifications on chromosome 15. Data plotted is the normalized log ratio for each probe (85K), sorted by chromosome position, of copy number for tumors relative to a normal reference DNA. (b)
Figure 8B:
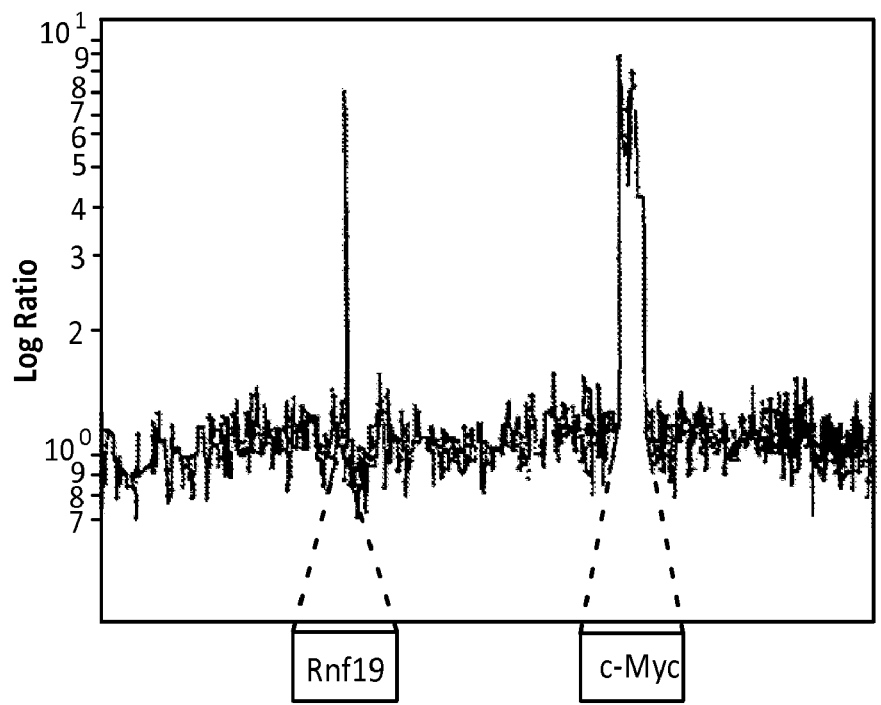

Genomic representations were produced from DNA obtained from several murine liver tumors and from normal mice tissue of the same genetic background, fluorescently labeled and hybridized to microarrays. The data derived after scanning was normalized as described (Sebat et al. "Large-scale copy number polymorphism in the human genome." *Science* 305, 525-528. (2004)). Even though all tumors were derived from cells harboring two defined genetic lesions, some displayed a small number of focal copy number alterations. For example, a ras-expressing tumor harbored two focal amplifications on chromosome 15 (FIG. 8A), including a 250 Kb amplicon that contains Rnf19 and a 2 Mb amplicon containing c-myc (FIG. 8B). While Rnf19 has not been previously linked to tumorigenesis, c-myc amplification is a common event in human liver cancer and, furthermore, c-myc cooperates with oncogenic ras in transgenic models of HCC (Sandgren et al. "Oncogene-induced liver neoplasia in transgenic mice." *Oncogene* 4, 715-724. (1989)). That a mutation affecting an established liver oncogene can occur spontaneously in these tumors underscores the relevance of the model of the present invention, and suggests that further analyses would reveal other genes involved in human cancer.

Recurrent Amplification of Chromosome 9qA1 in Myc-Expressing HCCs

Figure 8C:
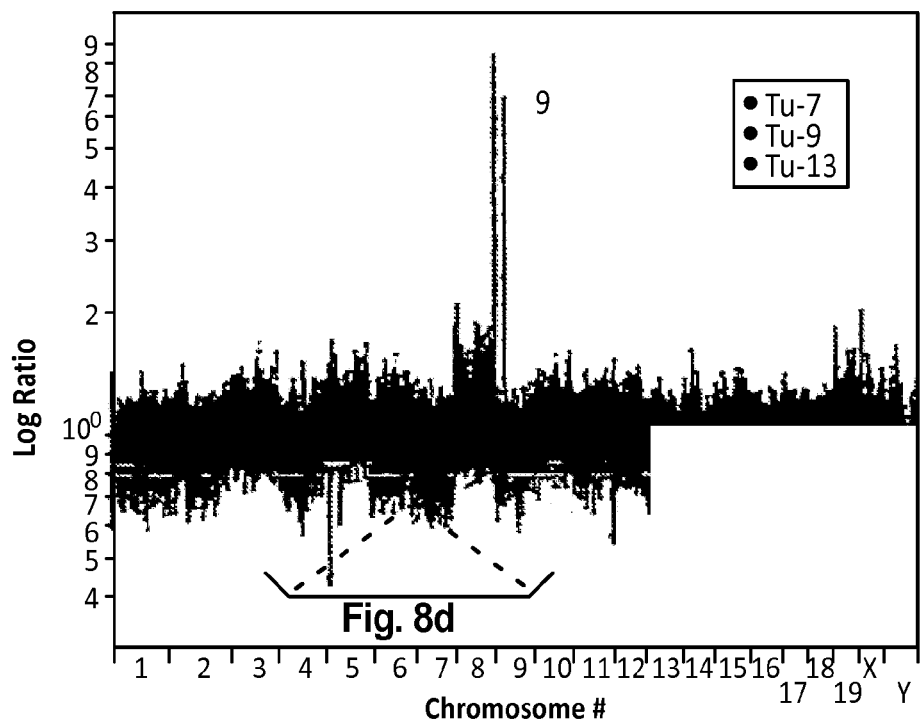
Figure 8D:
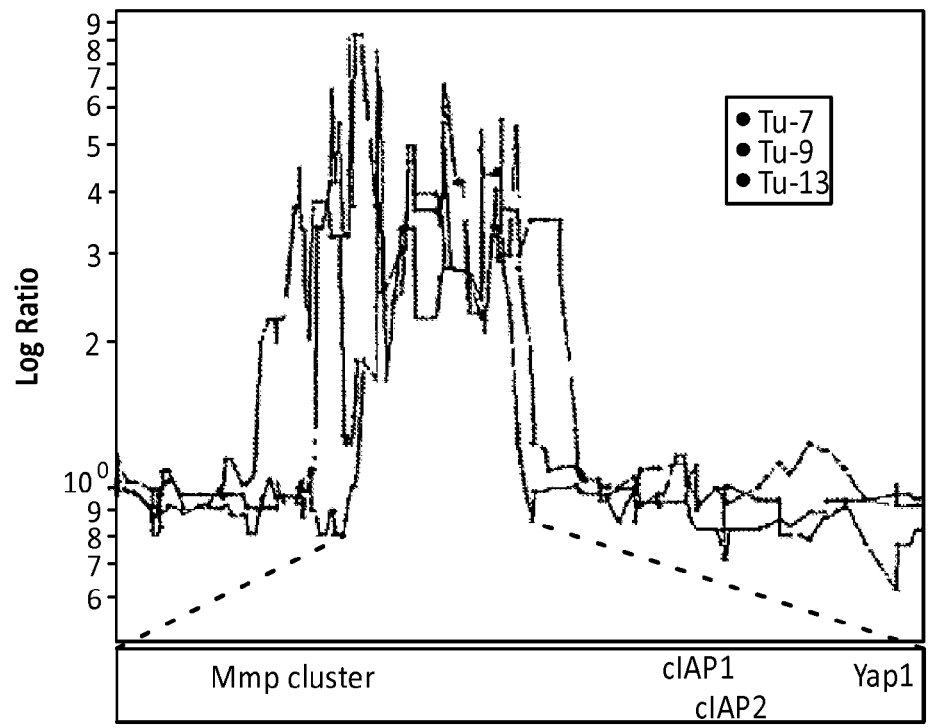

ROMA was also performed on seven independently derived Myc-expressing HCCs, and identified a focal amplicon on mouse chromosome 9qA1 in three of these tumors (FIG. 8C). As shown in a high resolution view (FIG. 8D), the minimal overlapping region was approximately 1 Mb and contained genes encoding for several matrix metalloproteinases (MMPs), Yap 1, cIAP1 (Birc2), and cIAP2 (Birc3) as annotated in the UCSC genome browser. An EST to Porimin also maps to this region. Amplification of this region was confirmed by genomic Q-PCR using a probe targeting the middle of the 9qA1 amplicon within the cIAP1 gene, a technique that also identified the 9qA1 amplicon in a fourth myc-expressing tumor (data not shown). Remarkably, 9qA1 was never found amplified in 15 other liver carcinomas expressing either Ras or Akt. These observations suggest that at least one of the genes in the 9qA1 region cooperates with myc and p53 loss to promote hepatocarcinogenesis.

Comparative Oncogenomics Reveals Lesions in Common Between Murine and Human Cancers In parallel to the analysis of murine HCCs, ROMA was conducted on 25 human HCC samples. These human tumors showed more complex alterations than the murine HCCs, yet we were able to detect copy number alterations affecting genes previously linked to HCC. For example, three tumors had a chromosome 11 amplification containing CCND1 (cyclin D1), two had a chromosome 7 amplification containing c-MET, and one had a deletion of chromosome 9 harboring the CDKN2A (INK4a/ARF) locus (data not shown).

Figure 9A:
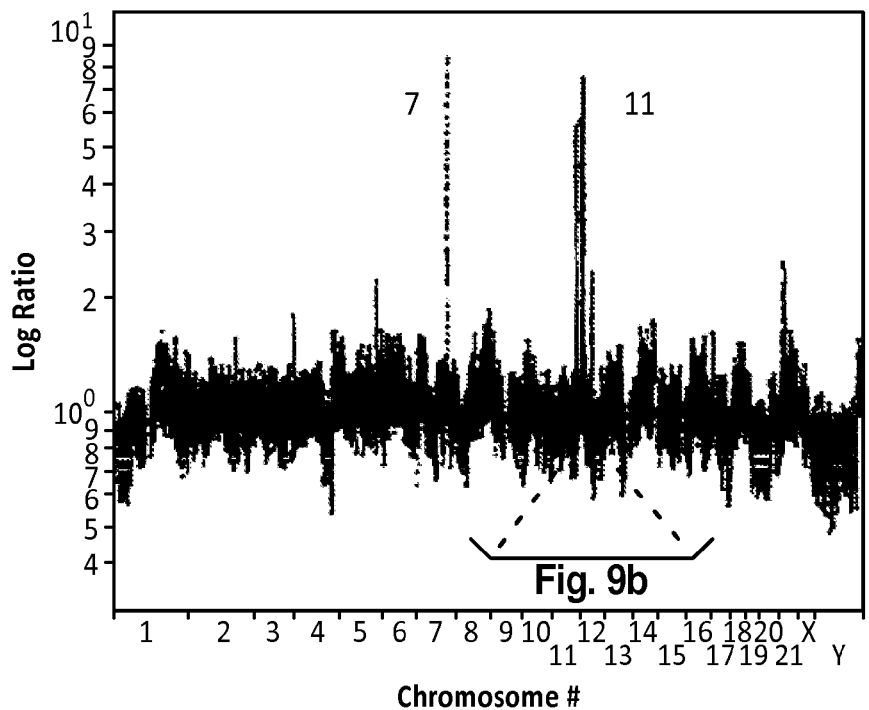
Figure 9B:
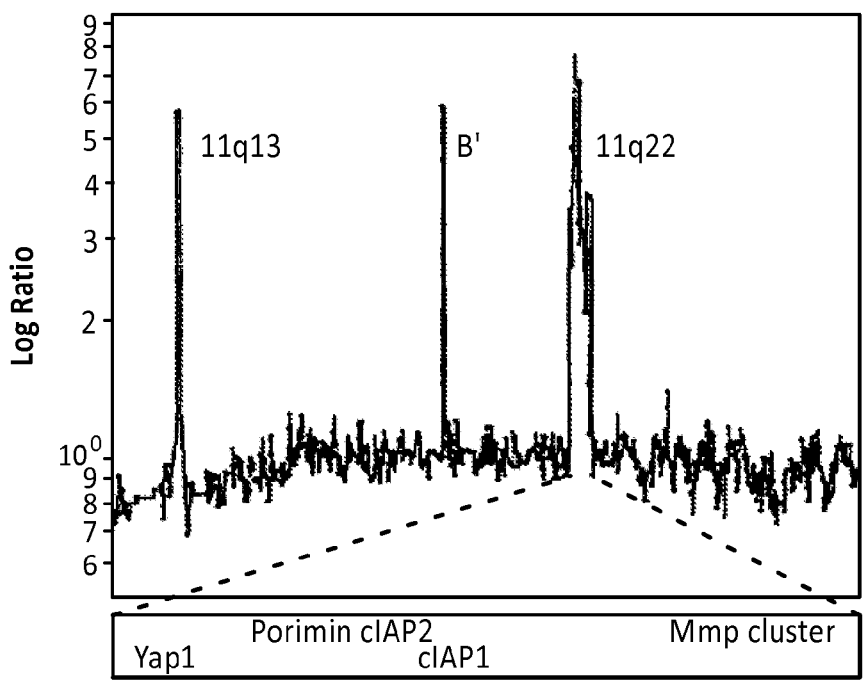
Figure 9C:
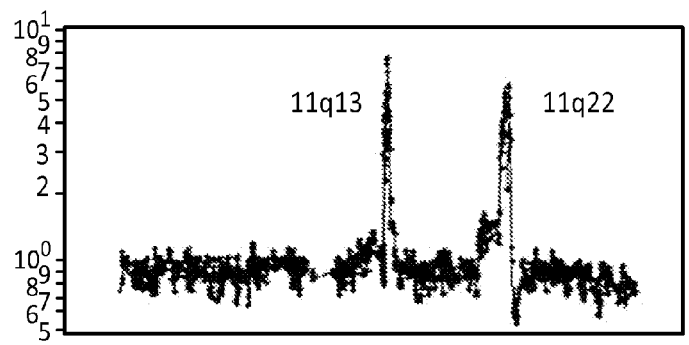

FIG. 9A shows a genome-wide profile of a liver tumor with a c-MET amplification (left peak) on chromosome 7, and three sharply delineated amplifications on chromosome 11 (FIG. 9B), including CCND1, B' (containing no known genes), and 11q22. Only focal gains or losses<5 MB were included in the analysis. Interestingly, the amplified region of human chromosome 11q22 is syntenic to mouse 9qA1, the region amplified in murine HCCs described above. Through the use of ROMA and/or genomic quantitative PCR to the cIAP1 and cIAP2 loci, we detected this same amplicon in a panel of human esophageal cancers (FIG. 9C, 4 of 53 tested; data not shown), indicating that it occurred in gastrointestinal malignancies derived from developmentally related organs. Much like the chromosome 9 amplicon in murine HCCs, the boundaries of this 11q22 amplicon include genes encoding several matrix metalloproteinases, Porimin, Yap1, cIAP1 and cIAP2.

Figure 9D:
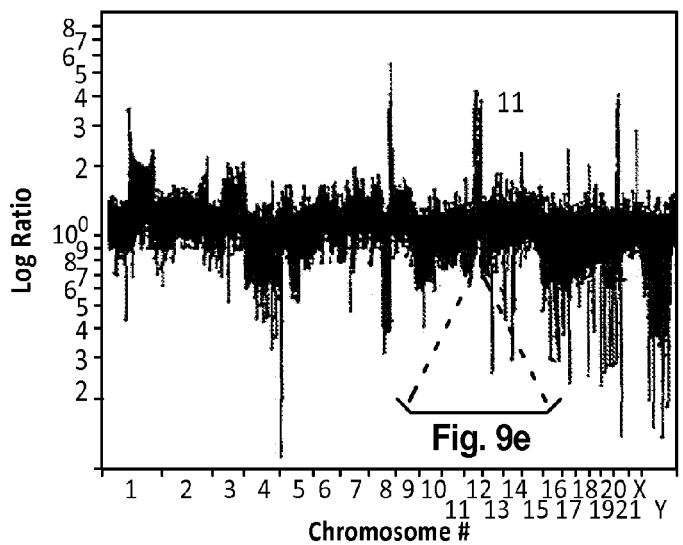
Figure 9E:
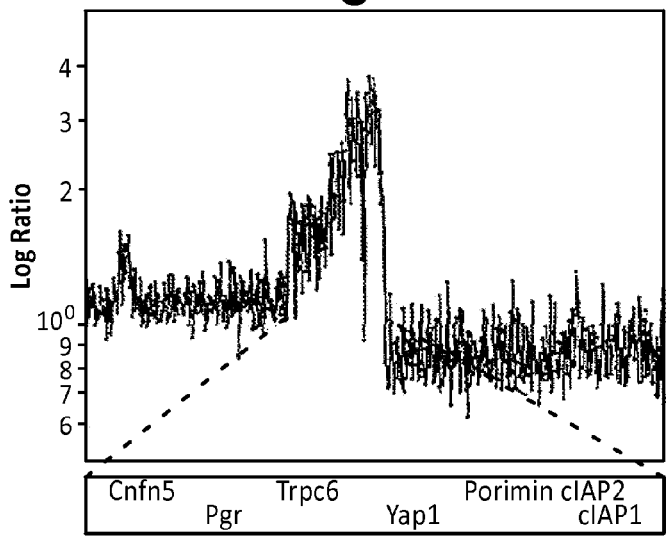
Figure 10A:
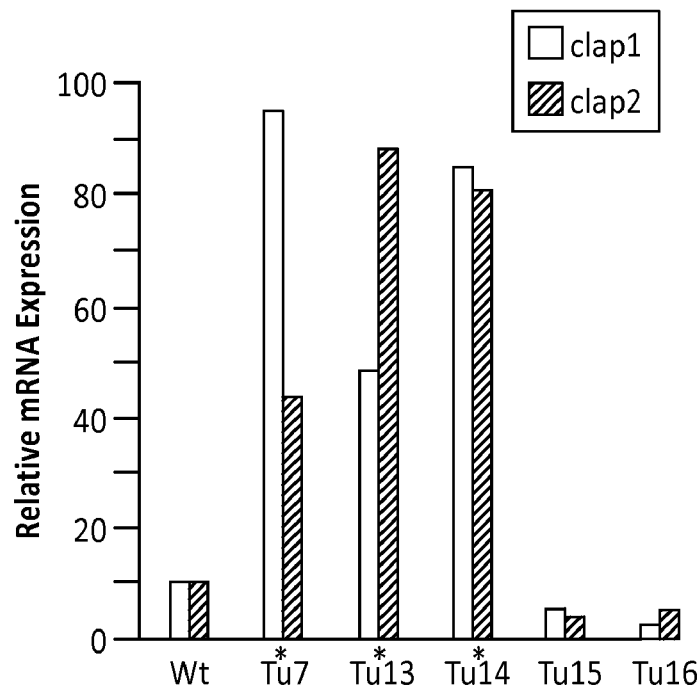
Figure 10B:
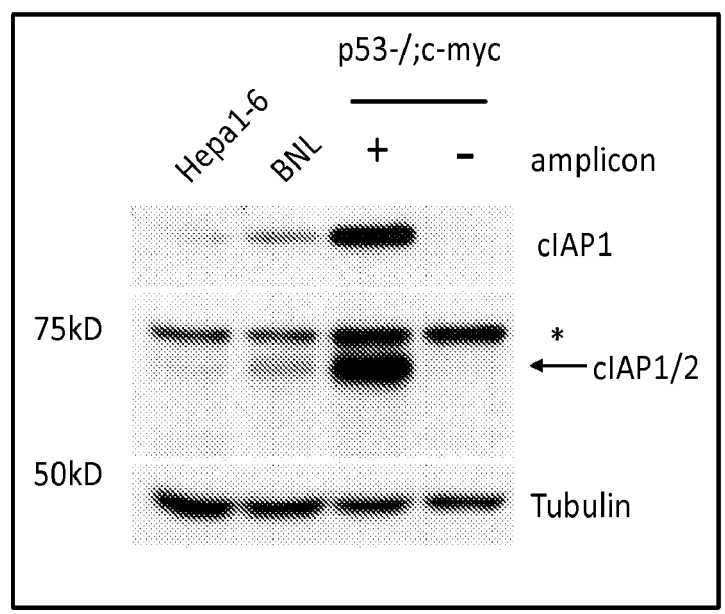
Figure 10C:
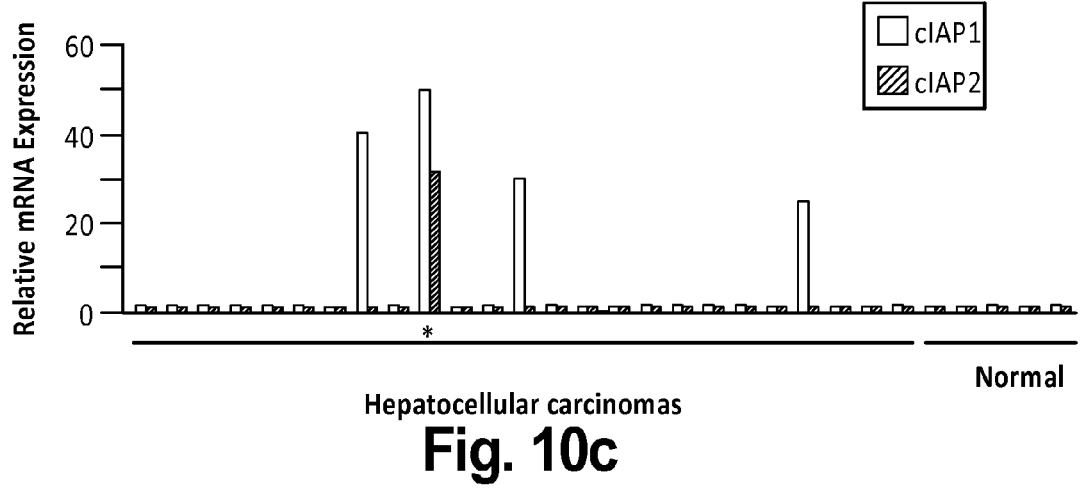
Figure 10D:
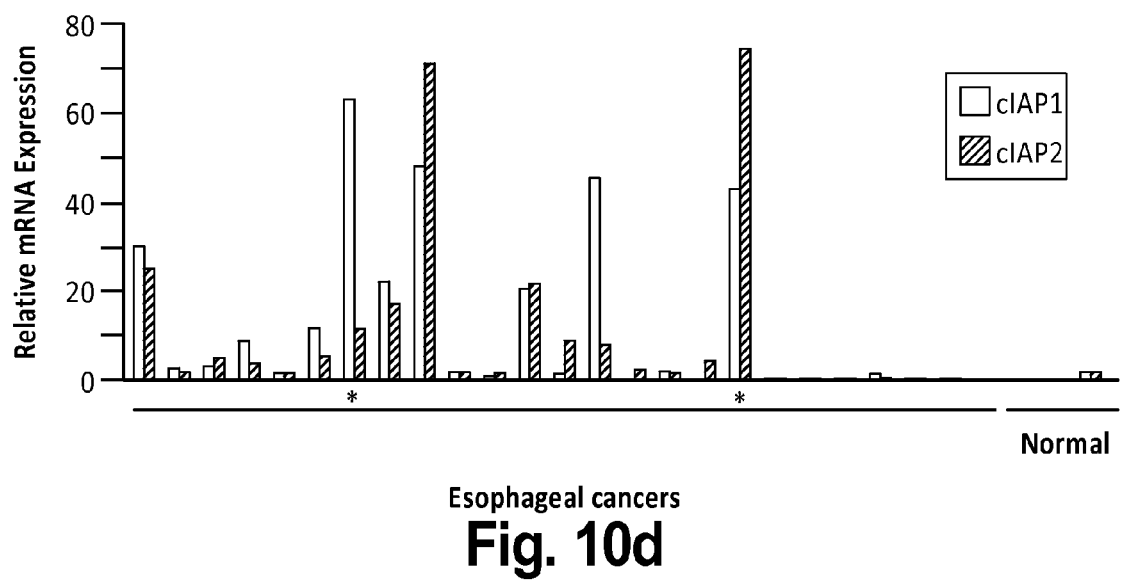

The human 11q22 amplicon has previously been observed at low frequency in other human cancers, although no driver gene has been decisively identified. While it represents only one of many low frequency events in these tumors, our cross-species comparison suggests that a gene(s) in the amplified region is crucial for tumorigenesis in certain contexts. In an attempt to further narrow down potential candidates, a series of other cancers that were previously analyzed by ROMA were examined to identify the minimal region of overlap. FIGS. 9D and 9E show an example of an ovarian carcinoma harboring an 11q22 amplicon that was particularly informative: although this tumor is genomically unstable, the MMPs are excluded from this 11q22 amplification suggesting that overexpression of this cluster is not the key selected driving event. Therefore, the genes contained within the epicenter of the amplicon are Porimin, Yap1, cIAP1 and cIAP2.

cIAP1 is Consistently Overexpressed in Tumors Harboring the Murine 9qA1 and Human 11q22 Amplicons One criterion for establishing whether a gene in an amplicon might contribute to tumorigenesis is that it shows elevated expression in the tumor. RT-Q-PCR analysis was conducted on a series of tumors to examine which genes in the mouse 9qA1 and human 11q22 amplicons were consistently overexpressed. The murine p53−/−; myc HCCs that contain the 9qA1 amplicon consistently overexpressed cIAP1 and cIAP2 mRNA, and cIAP1 protein (FIGS. 10A and B). These genes were not upregulated in tumors without the amplicon. Both genes were overexpressed in the human HCC and esophageal tumors harboring the 11q22 amplicon, but also in a substantial number of tumors without cIAP1/cIAP2 copy number elevation (FIGS. 10C and D; 4 of 25 HCC; 15 of 50 esophageal). Interestingly, cIAP1 was the only cIAP overexpressed in human HCCs without 11q22 amplification (FIG. 10C), hinting that this gene might have a particularly important role in this disease. Based on these analyses, cIAP1 is a likely driver gene in liver cancer.

cIAP1 has Oncogenic Properties

Inhibitor of apoptosis (IAP) proteins were originally identified in baculovirus because of their potential to inhibit cell death of infected cells. Similar to their viral counterparts, overexpression of cellular lAPs can inhibit apoptosis induced by different stimuli. Although lAPs have been shown to bind and inhibit caspases, it is controversial as to whether they are important regulators of apoptosis in mammalian cells. Furthermore, although indirect evidence point towards lAPs playing a role in oncogenesis (Wright & Duckett. "Reawakening the cellular death program in neoplasia through the therapeutic blockade of IAP function." *J. Clin. Invest* 115, 2673-2678. (2005)), there remains no direct evidence that these genes actively contribute to tumor initiation or maintenance.

Figure 11A:
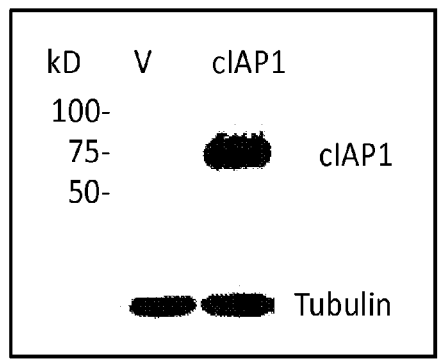
Figure 11B:
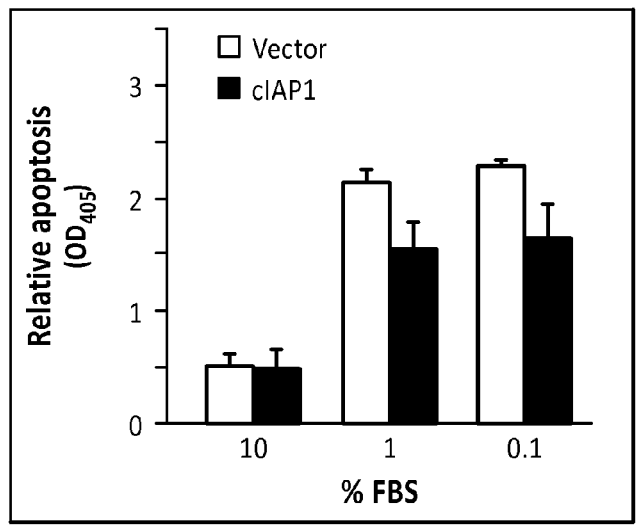
Figure 11C:
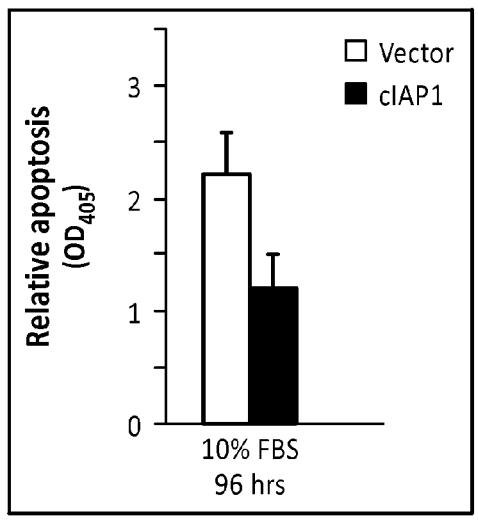
Figure 11D:
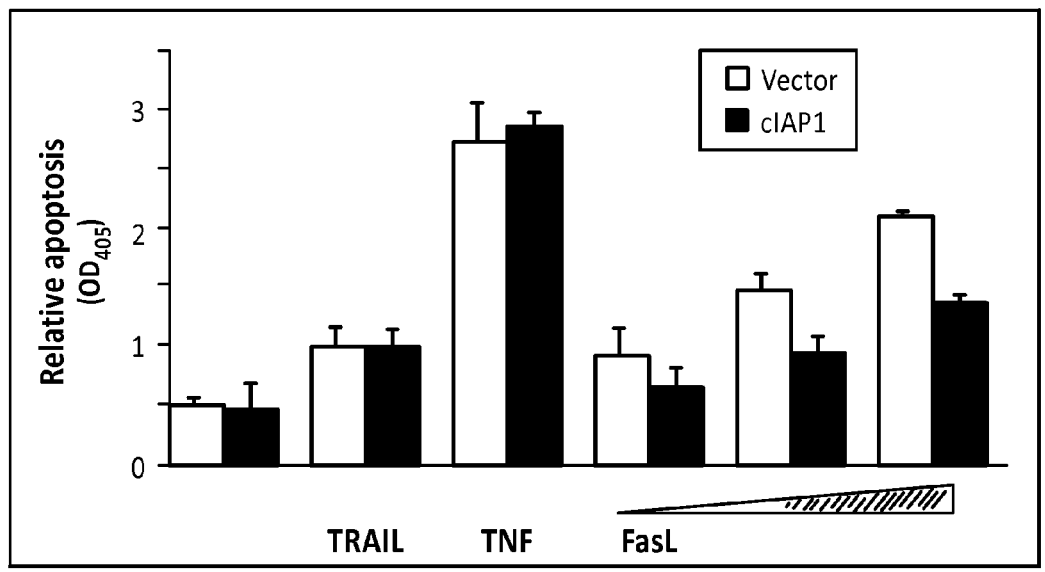
Figure 11E:
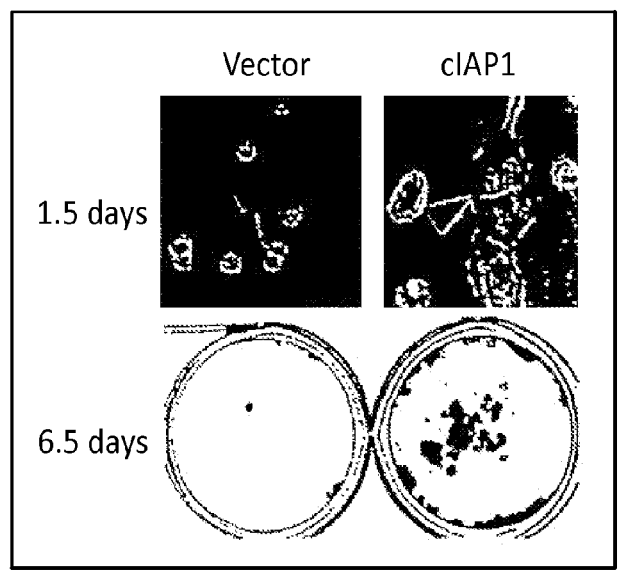

A significant advantage of profiling the genomes of defined murine tumors is that candidate genes can be validated in the genetic context, in which the mutation spontaneously arose during tumorigenesis. Our studies identified the 9qA1 amplicon in tumors derived from p53−/− hepatoblasts expressing Myc but not in other configurations, suggesting these cells would be ideal for evaluating the oncogenic properties of cIAP1. Therefore, p53−/−; myc liver progenitor cells expressing cIAP1 or a control vector were produced using retroviral mediated gene transfer, and the resulting cell populations were examined for transgene expression (FIG. 11A) and subjected to different apoptotic triggers. In this cell type, cIAP1 overexpression conferred a modest protection from growth factor withdrawal and spontaneous cell death at confluence (FIG. 11B and 11C). Surprisingly, cIAP1 had no effect on apoptosis induced by the death ligands TRAIL and TNFa (FIG. 11D), although it did confer substantial short and long-term protection from Fas-mediated apoptosis (FIG. 11D and E). Thus, cIAP1 can suppress apoptosis in murine hepatoblasts in vitro.

Figure 12A:
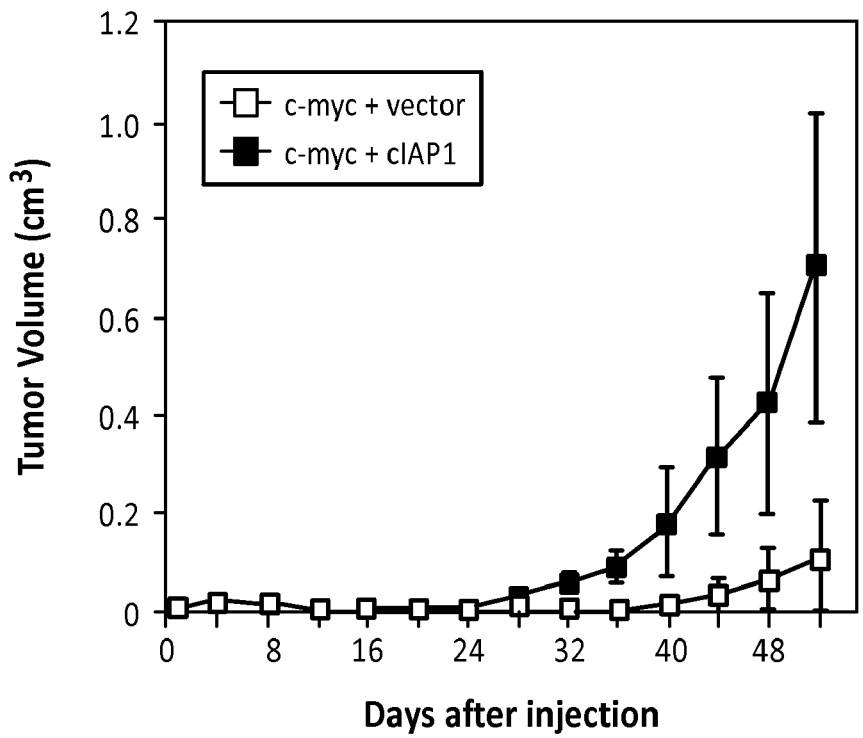
Figure 12B:
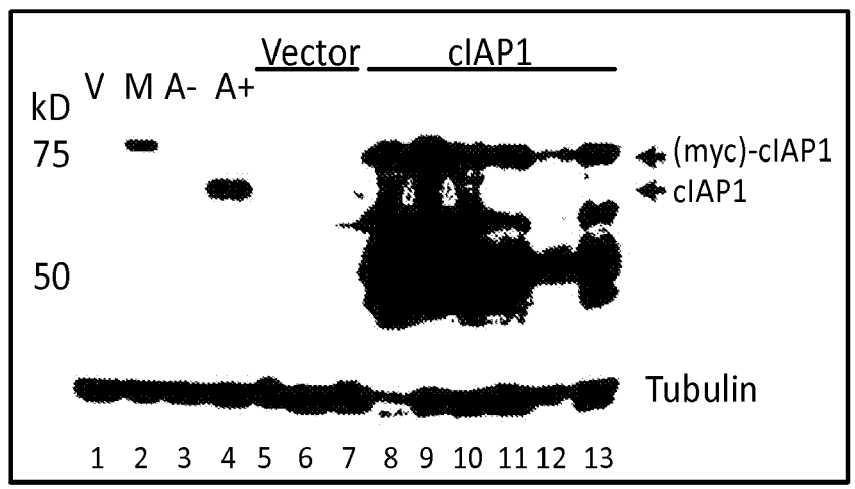
Figure 12C:
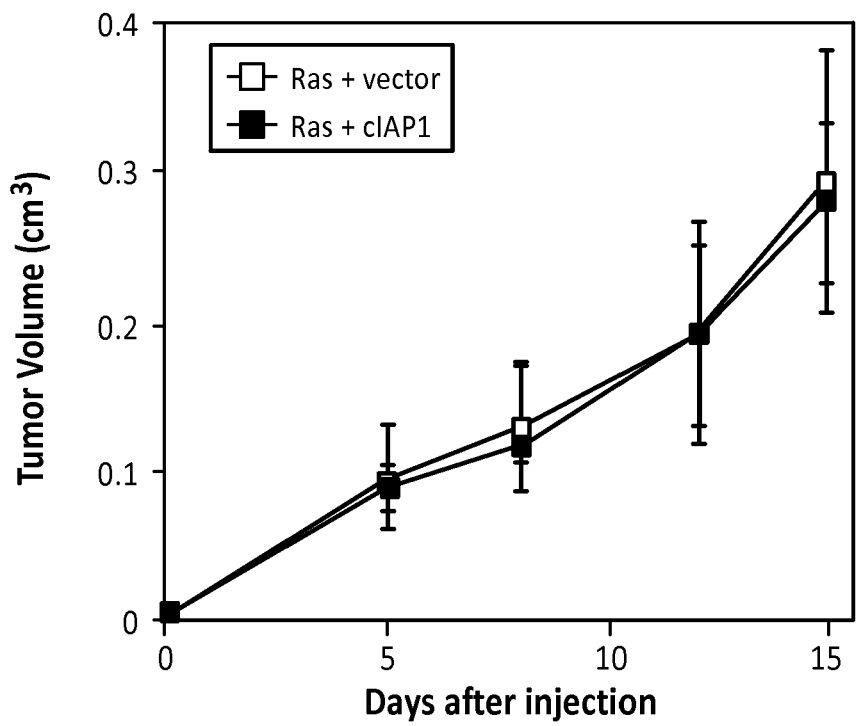

To determine whether cIAP1 could function as an oncogene in vivo, the hepatoblast cultures described above were injected subcutaneously into nude mice to facilitate precise measurement of tumor growth. cIAP1 overexpression significantly accelerated the growth of p53−/− hepatoblasts expressing Myc (FIG. 12A) (onset time of 24±2.3 for myc+cIAP1 vs. 45±12.2 for myc+vector (p=0.02)). The tumors displayed the histopathology of moderately well to poorly differentiated HCC (data not shown) and stably overexpressed the cIAP1 protein at high levels (FIG. 12B, compare lane 2 to lanes 7-13). Also present were low molecular weight forms of cIAP1, consistent with the susceptibility of this protein to proteolytic degradation. Interestingly, one control tumor that was harvested at a very small size showed elevated levels of cIAP1 (FIG. 12B, lane 6), suggesting that a subset of these cells had acquired a spontaneous alteration that upregulated the gene.

Figure 12D:
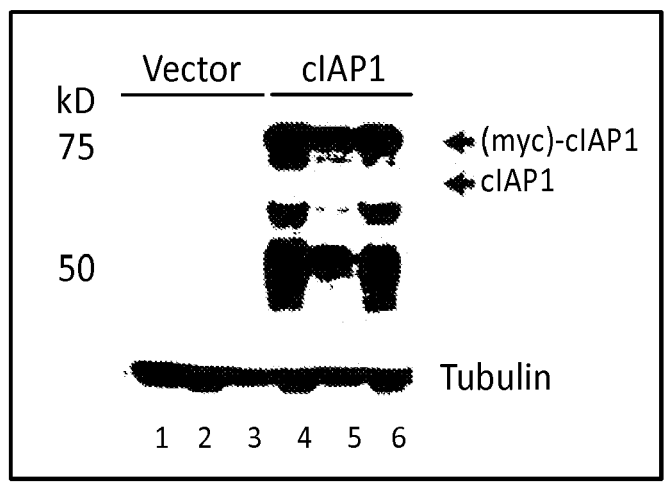
Figure 12E:
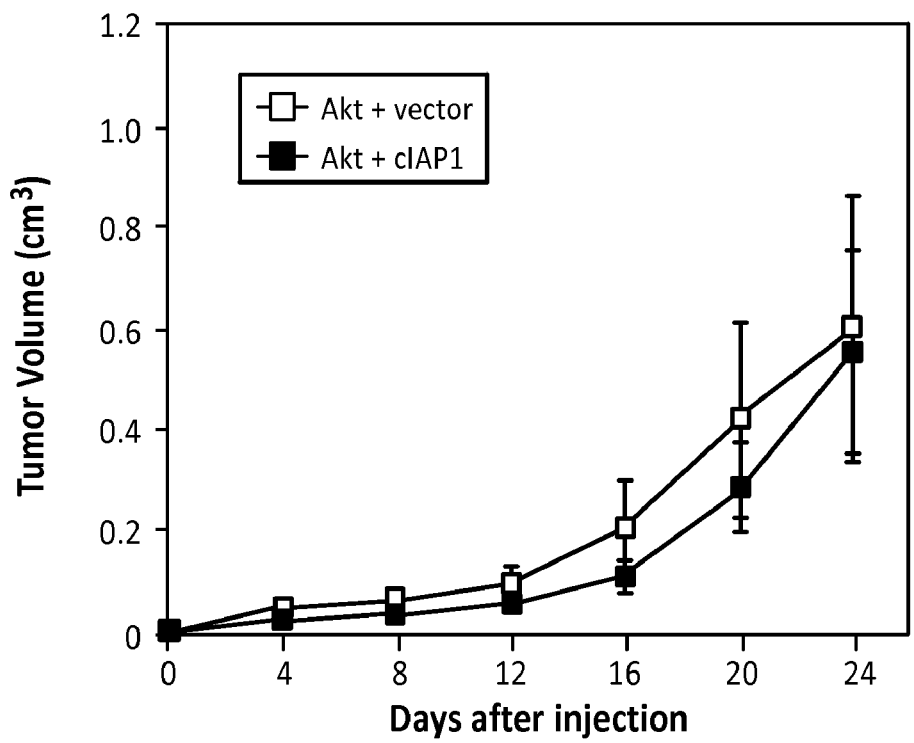
Figure 12F:
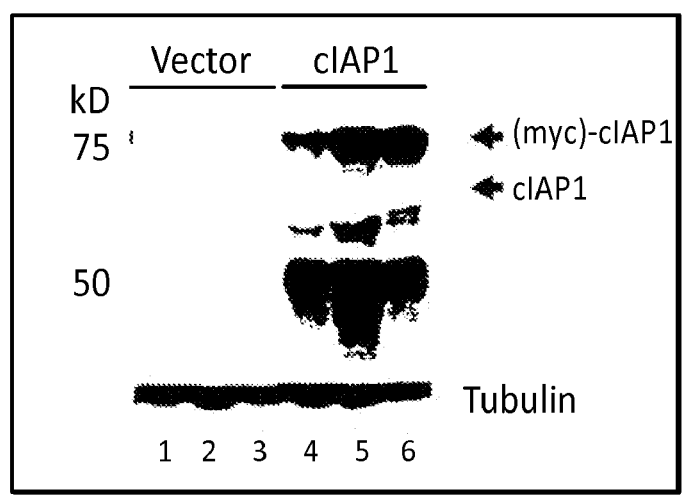

The ability of cIAP1 to promote tumorigenicity in cooperation with Akt or Ras was also examined. Using the same procedures described above, we produced p53−/− hepatoblasts expressing either Akt or Ras with or without cIAP1. In contrast to the Myc configuration, overexpression of cIAP1 has no impact on the onset or progression of tumors expressing Akt or Ras (FIGS. 12C and E), even though cIAP1 was efficiently expressed (FIGS. 12D and F). Thus, cIAP1 is selectively oncogenic in the genetic context where its amplification occurs.

cIAP1 and cIAP2 are Required for Rapid Tumor Growth

The above data demonstrates that cIAP1 can causally contribute to HCC development. To determine whether the cIAP proteins were required to sustain tumor growth, the impact of reducing cIAP levels on the growth of Myc-induced HCCs was examined in vivo. The expression of cIAP1 and cIAP2 was suppressed, since cIAP2 can be upregulated in response to cIAP1 suppression. First, a series of retroviral vectors expressing shRNAs capable of suppressing cIAP1 (hygromycin selectable) and cIAP2 (puromycin selectable) expression by RNA interference were generated. The best performing shRNAs were co-introduced into outgrown Myc-induced HCC cells containing or lacking the 9qA1 amplicon. Using these vectors, there was significant downregulation of endogenous cIAP1/2, as shown by immunoblotting using an antibody directed against cIAP1 or an antibody that cross-reacts with both cIAP1 and cIAP2 (FIG. 13). Some of these cells were also subsequently injected subcutaneously into the flanks of immuno-compromised mice, and tumor growth was assessed by caliper measurement.

Figure 13A:
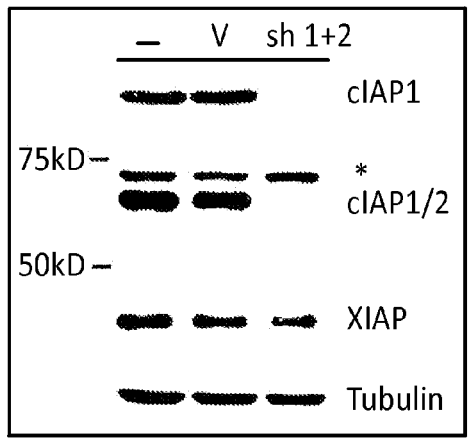
Figure 13B:
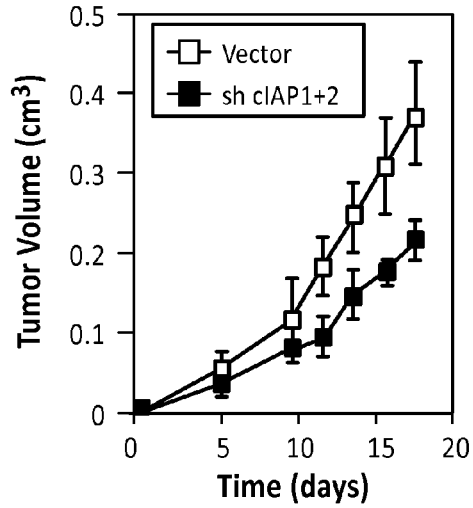
Figure 13C:
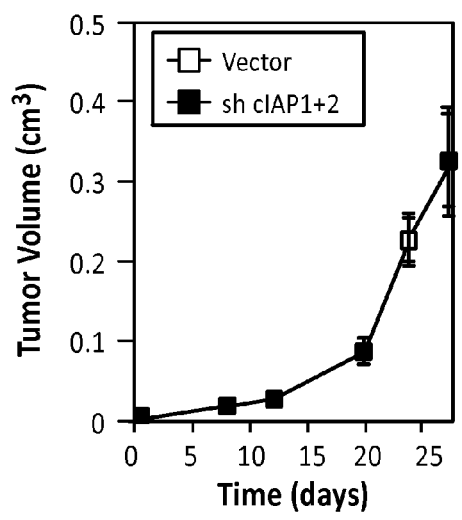
Figure 13D:
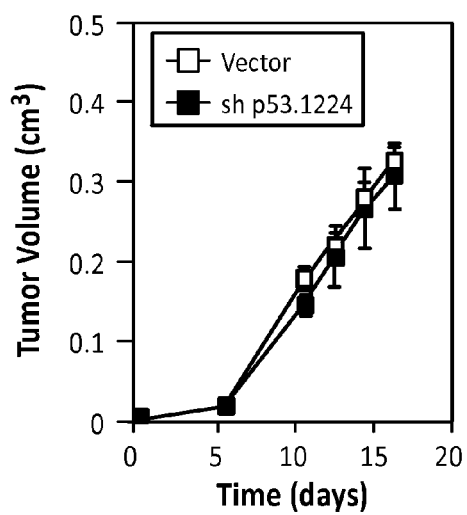

In tumors harboring the 9qA1 amplicon, suppression of cIAP1/2 had a marked impact on tumor growth. Thus, tumors expressing cIAP1 and cIAP2 shRNAs showed a reduced growth rate compared to parallel tumors expressing the control vectors (FIG. 13B). By contrast, these same shRNAs had no impact on the growth of an amplicon negative tumor derived from the same genotype (FIG. 13C), suggesting that only cells selected for cIAP overexpression are sensitive to cIAP inhibition. This latter observation also rules out off-target effects of these shRNAs on tumor growth. Consistent with this hypothesis, a p53 shRNA did not inhibit the growth of the p53−/−; myc tumor containing the 9qA1 amplicon (FIG. 13D). Therefore, cIAP1 and 2 are required for the efficient growth of tumors harboring the 9qA1 amplicon and thus may be therapeutic targets in a subset of human cancers.

Example 2

We took an integrated oncogenomic approach to identify new tumor suppressor genes in hepatocellular carcinoma. We combined microRNA based shRNA technology with a progenitor cell derived mouse model of liver cancer to perform in vivo RNA interference screens for new tumor suppressor genes in liver cancer.

Selecting RNAi Libraries Based on Human Oncogenomic Data

Figure 14A:
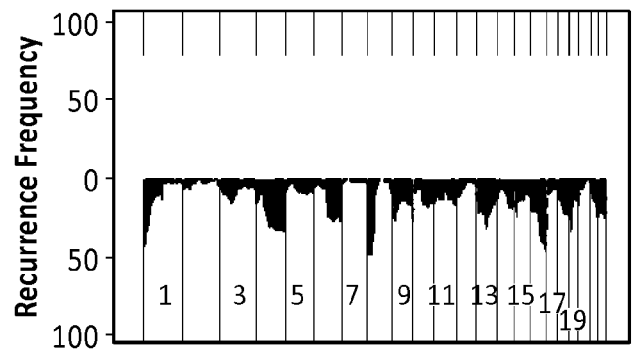
Figure 14A:
Figure 14A:
Figure 14A:
Figure 14A:
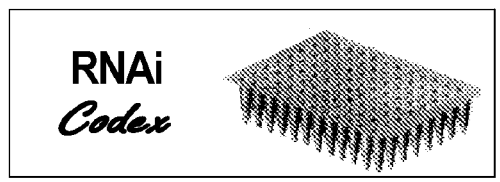
Figure 14A:
Figure 14A:
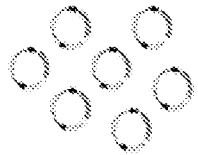

We analyzed 98 human hepatocellular carcinomas of different etiologies by Representational Oligonucleotide Microarray (ROMA) analysis, a high resolution array-CGH based platform, in order to identify recurrent focal genomic deletions. 59 focal genomic deletions (<5 MB) were identified, embedding a total of 362 known genes. For 301 of these genes we could identify mouse homologs. We obtained a total of 631 shRNAmir targeting these 301 genes from the RNAi Codex Cold Spring Harbor shRNAmir mouse library. Cultures of pSMc shRNAmir library clones were pooled to assemble low complexity shRNAmir library pools (n=48) (FIG. 14a). To allow for in vivo RNAi screening, we shuttled SalI/MluI fragments (which contains shRNAmir and a unique barcode sequence for every hairpin sequence) from the low complexity pSM2c library pools (FIG. 14b) into an MSCV based retroviral vector which has been optimized for in vivo use (FIG. 14c). In this vector the microRNA based shRNAs are driven by the retroviral LTR promoter, which has been shown to greatly improve knockdown efficiency, even at single copy integration in the genome. Resulting shRNAmir library pools underwent high throughput sequencing to confirm that subcloning of the library pools did not impact their complexity and representation (data not shown).

RNAi Constructs Targeting APC Tumor Suppressor Gene Induce Liver Carcinoma

We discovered that embryonic hepatocytes harvested from p53−/− mice are only immortalized but not transformed after transduction with a single copy c-myc transgene. We therefore used ED18 c-myc; p53−/− cells as our test system to perform in vivo RNAi screens for new tumor suppressor genes in hepatocellular carcinoma.

Deregulated Wnt-signaling is prevalent in a high percentage of human hepatocellular carcinomas, mostly due to activating mutations in the beta catenin gene, inactivating mutations in the axin tumor suppressor gene, or promoter hypermethylation of the APC tumor suppressor gene.

We therefore generated two independent populations of ED18 c-myc/p53−/− embryonic hepatocytes and transduced them with three different shRNAmir targeting the APC tumor suppressor gene or with a control shRNA and transplanted the resulting cell populations either subcutaneously on nude mice or seeded the cells into the livers of recipient mice via intrasplenic injection. While shRNAmir$^{APC}$ transduced cells gave rise to liver carcinomas in both settings (FIGS. 15, a, b), transduction with control shRNAs did not trigger tumor growth of the same cell populations. Intrahepatic tumor growth could easily be followed up by bioluminescence imaging as cell populations were initially established using a luciferase tagged myc transgene. H&E staining of sections from liver carcinomas evolving from the c-myc; p53−/−; shAPC compound mutant cells were classified as aggressive hepatocellular carcinomas, mostly showing a solid, sometimes a pseudoglandular growth pattern (FIG. 15c, top panel). Immunohistochemical analysis revealed a strong nuclear accumulation of beta catenin in these tumors.

An important prerequisite for the conduction of RNAi screens using pooled shRNAs in any biological systems is that positive controls score at a dilution which represents the representation of a single shRNA in a library pool. We therefore tested whether a 1:50 dilution of a shRNAmir$^{APC}$ would still be sufficient to induce tumor growth in our system. Furthermore, we transduced c-myc; p53−/− embryonic hepatocytes with a low complexity shRNAmir library pool which contains two of the scoring shRNAmir$^{APC}$. Both experiments resulted in tumor growth, whereas the time to tumor onset was delayed compared to the cells transduced with a pure shRNAmir$^{APC}$ construct (FIG. 15d). In addition to shRNAmirAPC mediated deregulation of Wnt signaling, we found that down-regulation of the Axin tumor suppressor also resulted in the induction of aggressive hepatocellular carcinomas (FIG. 15d).

In Vivo RNAi Screening to Identify New Tumor Suppressor Genes in HCC

We next took advantage of our established system to performed in vivo RNAi screens in order to identify new tumor suppressor genes in HCC.

Figure 16A:
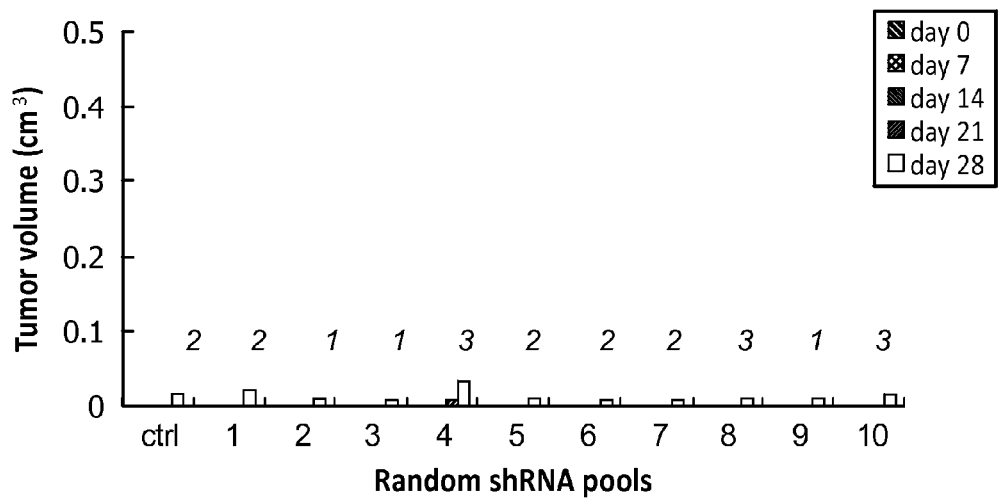
Figure 16B:
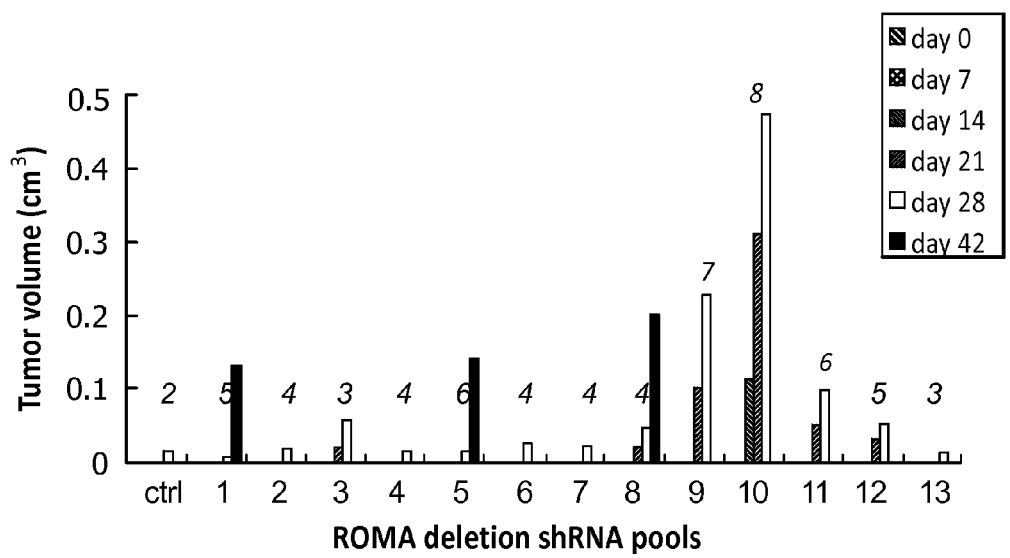

Two independent populations of ED18 c-myc; p53−/− liver progenitor cells were in infected with low complexity shRNAmir pools containing hairpins targeting the genes found in focal deletions of 98 human HCC (see, FIG. 14a, generation of the library pools). While the majority of shRNA pools from this focused library eventually triggered tumor growth, we found six pools that triggered the growth of aggressive HCCs as early as 14-21 days after injection of the cells (FIG. 16a). Importantly, only few tumors developed after long latency when the same c-myc; p53−/− cell populations were in parallel transduced with ten random shRNAmir pools (taken from a genome wide murine shRNAmir library) of the same pool size (n=48) (FIG. 16b).

Figure 16C:
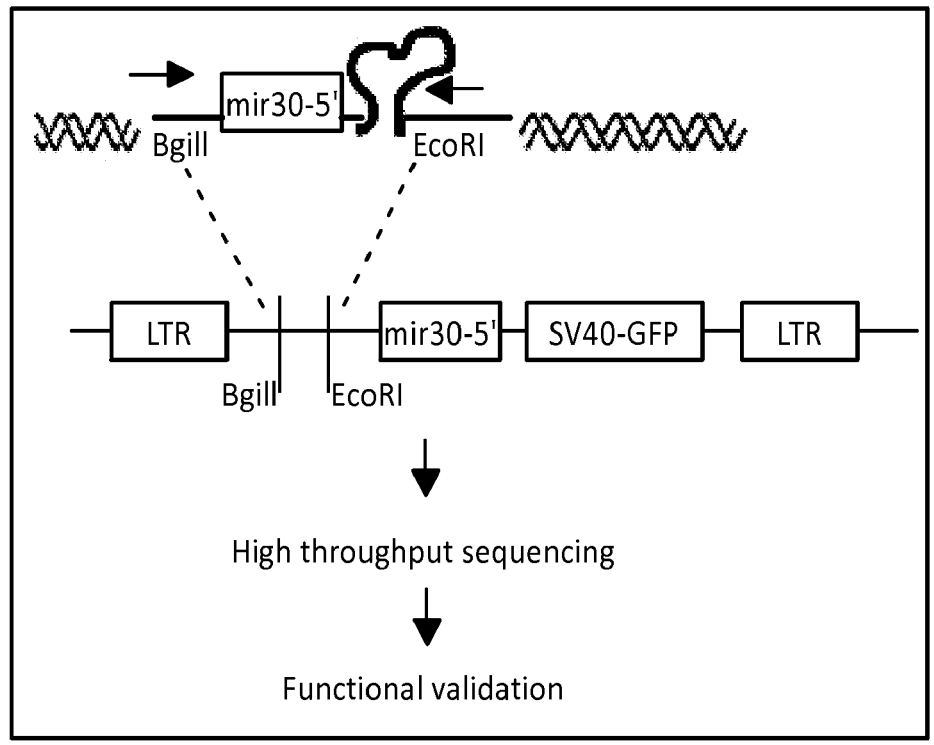

To identify scoring shRNAmir which cooperated with c-myc and p53 deficiency during tumorigenesis, we isolated genomic DNA from GFP-positive tumor nodules. Via PCR we amplified a fragment containing the mir30-5' flanking region as well as the unique shRNA sequence (FIG. 16c). PCR products were digested with BglII and EcoRI and cloned directionally into a recipient vector which contains the mir30-3' flanking region. The resulting vectors, containing the full shRNAmir cassette, were submitted for high throughput sequencing. At least hundred sequence reads were run per tumor, whereas at minimum three tumors from each pool (two independent experiments) were sequenced.

Figure 16D:
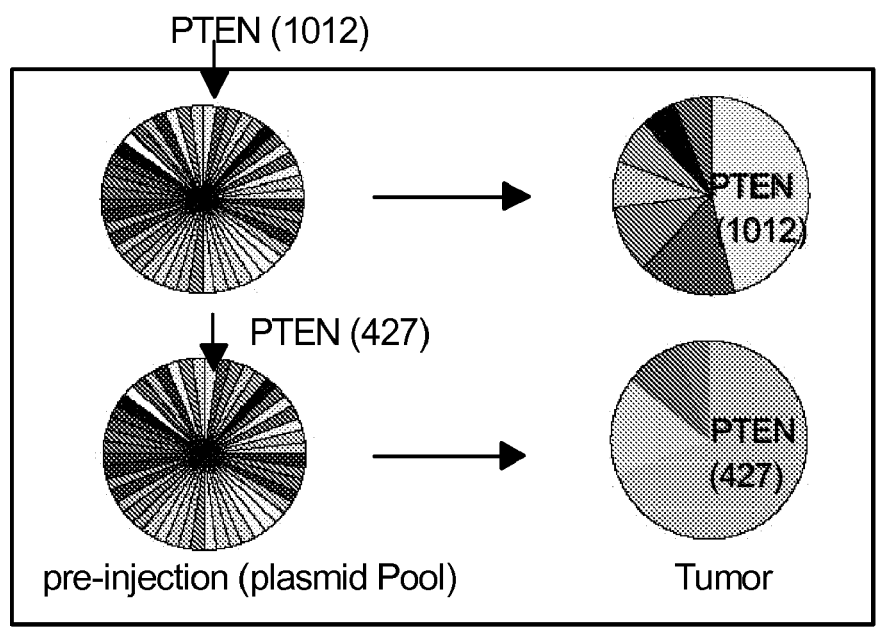

Down-Regulation of the PTEN Tumor Suppressor Cooperates with Myc and p53-Deficiency During Hepatocarcinogenesis We first analyzed shRNAmir representation in tumors which only showed moderately accelerated tumor growth. Interestingly, we found that tumors derived from two independent shRNAmir pools showed strong enrichment for two different hairpins targeting the PTEN tumor suppressor (FIG. 16d). Pie charts showing representative sequencing results from murine HCCs are shown in FIG. 16d (right panel). shRNAmirPTEN-1012 represented about 50% of all shRNAmir in the tumor, while shRNAmirPTEN-427 was even found in >40% of all sequence reads (shRNAmir representation in the low complexity shRNAmir library pool is symbolized by the pie chart in the left panel of FIG. 16d).

The hitherto results suggest that down-regulation of the PTEN tumor suppressor cooperates with myc and p53-deficiency during hepatocarcinogenesis. Our data are in accordance with published results showing activating mutations in Pi3k protein in HCCs, and biochemical activation of the Akt kinase in 40% of all human HCCs. Our ROMA analyses identified PTEN deletion in a total of four human hepatocellular carcinomas, one of them showing a focal deletion <5 MB (inclusion criterion for the focused shRNAmir library) and three additional ones with broader deletions >5 MB. A ROMA plot showing a focal, PTEN containing deletion on chromosome 10 in a human HCC is shown in FIG. 16e.

We next sought to test whether scoring shRNAmir that were identified in our in vivo RNAi screen could be functionally validated in our system. Both shRNAmirPTEN from the screen significantly knocked down PTEN protein levels. When infected into myc; p53−/− cells, both shRNAmir triggered the growth of liver carcinomas, while controls shRNAmir did not induce subcutaneous tumor growth in the same observation period (FIG. 16f). When the same shRNAmirPTEN transduced cell populations were seeded into the livers of recipient mice by intrasplenic injection, they also gave rise intrahepatic HCCs, as shown by bioluminescence imaging 4 weeks after seeding of the cells (FIG. 16g).

Identification of New Genes Associated with Tumorigenesis

We moved on to systematically analyze shRNA representation in all tumors, in particular those which showed fastest tumor growth.

A total of 3900 sequence reads were applied to 39 tumors induced by the 13 low complexity shRNAmir pools. Table 1 lists all shRNAs found enriched to >5% of the total sequencing reads in each given pool.

TABLE 1

| Hairpin ID | Mouse (HUMAN) gene name | shRNA specific reads/ total reads of pool |
|---|---|---|
| HP_76455 | Xpo4 (XPO4) | 351/560 (62.6%) |
| HP_253140 | Fgf6 (FGF6) | 175/342 (51.1%) |
| HP_345037 | Wdr49 (WDR49) | 137/342 (40%) |
| HP_89078 | Armcx2 (ARMCX2) | 88/290 (30.3%) |
| HP_465354 | Pten (PTEN) | 66/231 (28.5%) |
| HP_345044 | Fstl5 (FSTL5) | 45/201 (22.3%) |
| HP_55878 | Arid5b (ARID5B) | 49/231 (21.2%) |
| HP_484212 | Nrsn2 (NRSN2) | 60/284 (21.1%) |
| HP_246874 | Wdr37 (WDR37) | 60/284 (21.1%) |
| HP_302435 | Armcx1 (ARMCX1) | 61/290 (21%) |
| HP_238455 | Gjd4 (GJD4) | 76/396 (19.1%) |
| HP_282953 | BC050789 (FLJ23049) | 70/396 (17.6%) |
| HP_488528 | Armcx6 (ARMCX6) | 41/284 (14.4%) |
| HP_293818 | Fxr1h (FXR1) | 31/231 (13.4%) |
| HP_524 | Pten (PTEN) | 34/290 (11.7%) |
| HP_268588 | Ddx20 (DDX20) | 61/560 (10.8%) |
| HP_420314 | Pde3b (PDE3B) | 42/396 (10.6%) |
| HP_278543 | Glo1 (GLO1) | 29/284 (10.2%) |
| HP_284899 | Sh2d3c (SH2D3C) | 19/201 (9.4%) |
| HP_7310 | ITIH4 (ITIH4) | 21/231 (9%) |
| HP_283969 | Rnf125 (RNF125) | 26/290 (8.9%) |
| HP_309846 | 6530418L21Rik (C1orf183) | 18/201 (8.9%) |
| HP_322570 | 1810063B07Rik (C6orf64) | 32/396 (8%) |
| HP_353921 | Set (SET) | 32/396 (8%) |

TABLE 1-continued

| Hairpin ID | Mouse (HUMAN) gene name | shRNA specific reads/ total reads of pool |
|---|---|---|
| HP_522 | Pten (PTEN) | 18/231 (7.7%) |
| HP_22132 | Fgf6 (FGF6) | 43/560 (7.6%) |
| HP_268149 | Cc2d1a (CC2D1A) | 15/201 (7.4%) |
| HP_299169 | 1700010M22Rik (C20orf79) | 16/231 (6.9%) |
| HP_307744 | Olfr732 (OR4N4) | 19/284 (6.6%) |
| HP_272971 | Mapk4 (MAPK4) | 19/290 (6.5%) |
| HP_479490 | Olfr734 (OR4M1) | 17/284 (5.9%) |
| HP_485412 | Gm276 (FAM81B) | 22/396 (5.5%) |
| HP_270196 | Set (SET) | 31/560 (5.5%) |
| HP_265589 | Btbd9 (BTBD9) | 29/560 (5.1%) |
| HP_410182 | Mcart1 (MCART1) | 20/396 (5%) |
| HP_492873 | Fstl5 (FSTL5) | 20/396 (5%) |

A total of 36 candidate shRNAs enriched to >5% in tumors induced by the respective pool were found. Based on the enrichment factor, the two identified shRNAs targeting PTEN represent the $5^{th}$ and $15^{th}$ best scoring shRNAs, respectively.

Figure 18A:
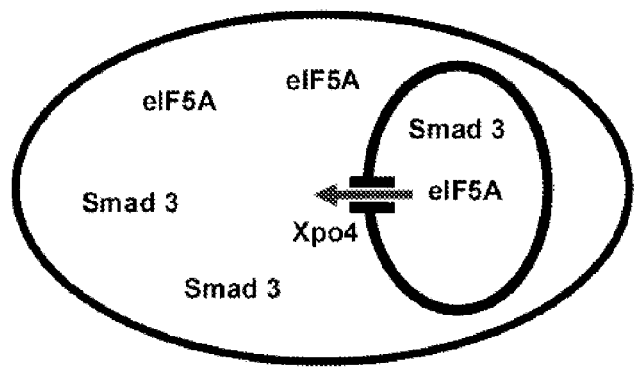
Figure 18B:
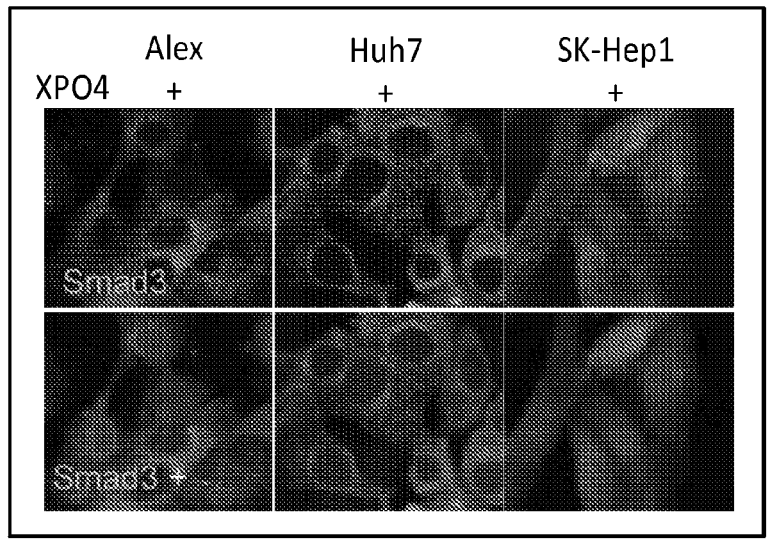
Figure 18C:
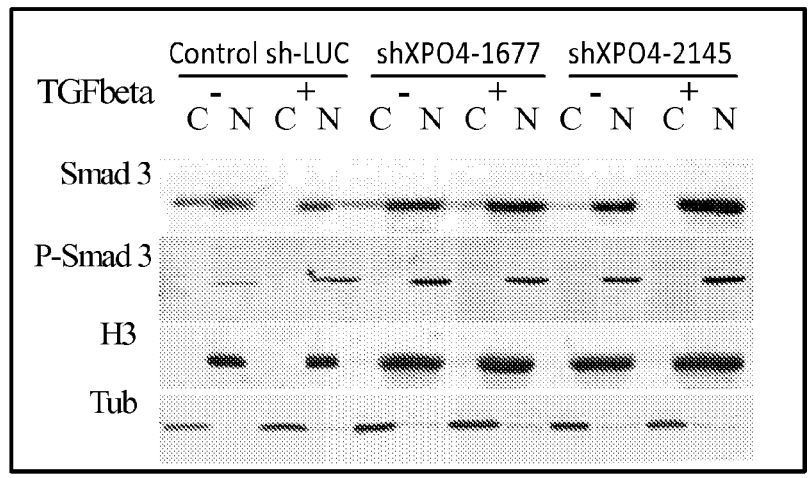
Figure 18D:
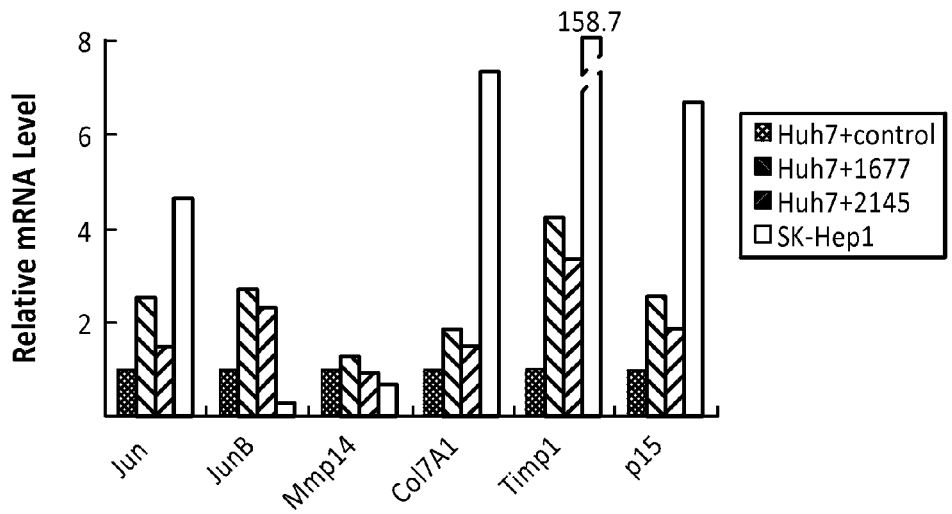
Figure 18E:
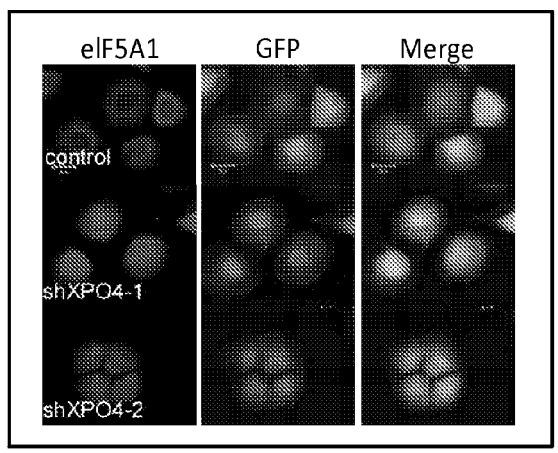
Figure 18F:
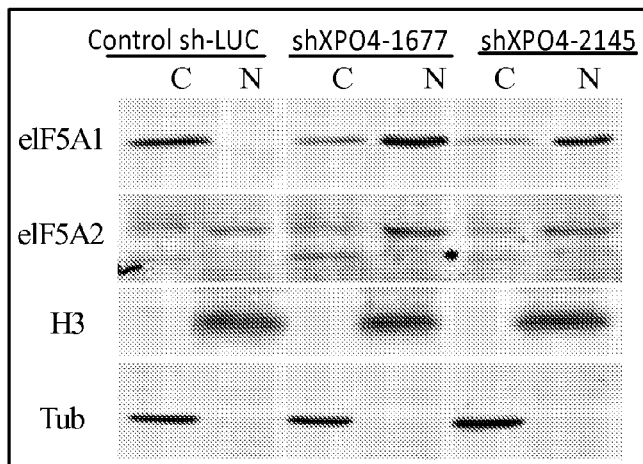
Figure 18G:
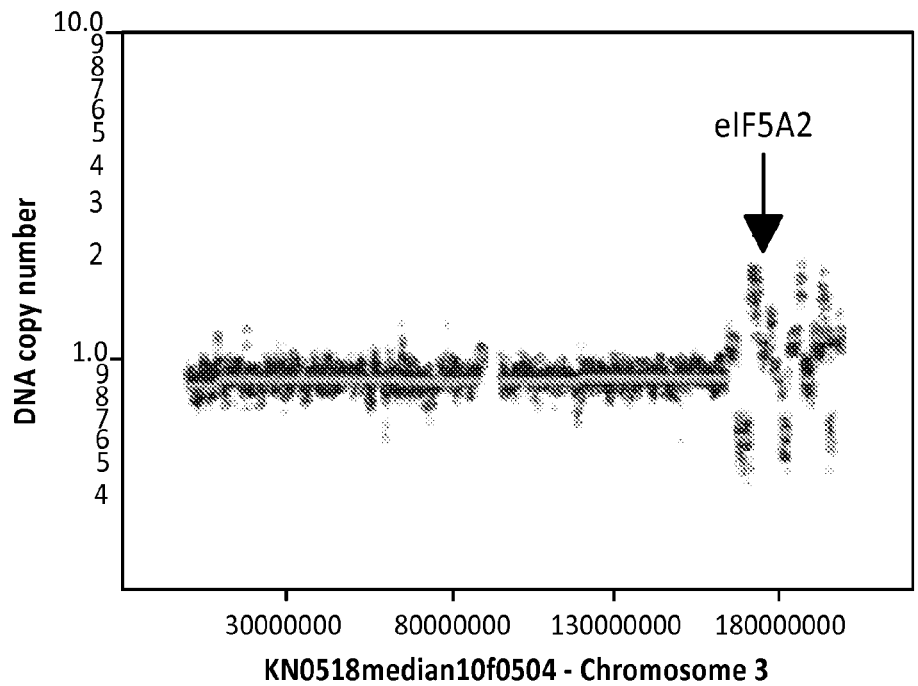

The top scoring shRNA is targeting Xpo4, a member of the importin-β superfamily. It has been shown that Xpo4 serves as a nuclear exporter for eIF5A1 and Smad3 but loss of Xpo4 expression has never been linked to cancer. Other genes targeted by the top five scoring shRNAs are FgF6, Wdr49 and Armcx2. Interestingly, none of these genes have been linked to tumorigenesis before. FIG. 18A shows pie charts which reveal the shRNA representation in five representative tumors. As shown, the top scoring shRNA targeting Xpo4 is enriched to >75 of all sequencing reads of the respective tumor. Other candidates like Cx40.1, Fstl5 and Gm123 show significant enrichment, however to a lesser extend than Xpo4. A systematic analysis of the sequencing results from all tumors derived from a respective pool is shown in Table 2.

TABLE 2

| Pool | Tumor incidence | Tumor ID (shRNA sequence reads) | shRNA ID | Mouse (HUMAN) gene name | No of reads |
|---|---|---|---|---|---|
| 1 | | 1-1 (68 reads) | HP_465354 | Pten (PTEN) | 45 |
| | | | HP_55878 | Arid5b (ARID5B) | 10 |
| | | | HP_17666 | Fxr1h (FXR1) | 6 |
| | | 1-2 (79 reads) | HP_465354 | Pten (PTEN) | 20 |
| | | | HP_55878 | Arid5b (ARID5B) | 18 |
| | | | HP_293818 | Fxr1h (FXR1) | 15 |
| | | | HP_48964 | Sh3glb2 (SH3GLB2) | 8 |
| | | | HP_299169 | 1700010M22Rik (C20orf79) | 8 |
| | | 1-3 (84 reads) | HP_55878 | Arid5b (ARID5B) | 21 |
| | | | HP_7310 | ITIH4 (ITIH4) | 16 |
| | | | HP_293818 | Fxr1h (FXR1) | 16 |
| | | | HP_522 | Pten (PTEN) | 13 |
| 5 | | 5-1 (73 reads) | HP_524 | Pten (PTEN) | 30 |
| | | | HP_283949 | Rnf125 (RNF125) | 11 |
| | | | HP_295488 | Itpr1 (ITPR1) | 7 |
| | | 5-2 (81 reads) | HP_89078 | Armcx2 (ARMCX2) | 34 |
| | | | HP_272971 | Mapk4 (MAPK4) | 14 |
| | | | HP_283949 | Rnf125 (RNF125) | 12 |
| | | | HP_288339 | Rin2 (RIN2) | 8 |
| | | 5-3 (77 reads) | HP_89078 | Armcx2 (ARMCX2) | 49 |
| | | | HP_291484 | St6galnac4 (ST6GALNAC4) | 6 |
| | | 5-4 (62 reads) | HP_302435 | Armcx1 (ARMCX1) | 59 |
| 8 | | 8-1 (84 reads) | HP_345037 | Wdr49 (WDR49) | 38 |
| | | | HP_253140 | Fgf6 (FGF6) | 33 |
| | | | HP_415905 | Zmym2 (ZMYM2) | 7 |
| | | 8-2 (86 reads) | HP_253140 | Fgf6 (FGF6) | 56 |
| | | | HP_345037 | Wdr49 (WDR49) | 28 |
| | | 8-3 (90 reads) | HP_253140 | Fgf6 (FGF6) | 48 |
| | | | HP_345037 | Wdr49 (WDR49) | 41 |
| | | 8-4 (82 reads) | HP_253140 | Fgf6 (FGF6) | 38 |
| | | | HP_345037 | Wdr49 (WDR49) | 30 |
| | | | HP_415905 | Zmym2 (ZMYM2) | 6 |
| | | | HP_229153 | Polr3f (POLR3F) | 6 |
| 9 | | 9-1 (69 reads) | HP_484212 | Nrsn2 (NRSN2) | 23 |
| | | | HP_488528 | Armcx6 (ARMCX6) | 15 |
| | | | HP_278543 | Glo1 (GLO1) | 11 |
| | | | HP_246874 | Wdr37 (WDR37) | 8 |
| | | 9-2 (64 reads) | HP_484212 | Nrsn2 (NRSN2) | 36 |
| | | | HP_353467 | Ccny (CCNY) | 6 |
| | | 9-3 (77 reads) | HP_246874 | Wdr37 (WDR37) | 31 |
| | | | HP_479490 | Olfr734 (OR4M1) | 15 |
| | | | HP_307744 | Olfr732 (OR4N4) | 14 |
| | | 9-4 (74 reads) | HP_488528 | Armcx6 (ARMCX6) | 20 |
| | | | HP_246874 | Wdr37 (WDR37) | 19 |
| | | | HP_278543 | Glo1 (GLO1) | 18 |
| 10 | | 10-1 (72 reads) | HP_76455 | Xpo4 (XPO4) | 35 |
| | | | HP_477212 | Serpini2 (SERPINI2) | 7 |
| | | | HP_268588 | Ddx20 (DDX20) | 7 |
| | | | HP_265589 | Btbd9 (BTBD9) | 6 |
| | | 10-2 (53 reads) | HP_22132 | Fgf6 (FGF6) | 43 |
| | | 10-3 (86 reads) | HP_76455 | Xpo4 (XPO4) | 68 |
| | | | HP_268588 | Ddx20 (DDX20) | 16 |

TABLE 2-continued

| Pool | Tumor incidence | Tumor ID (shRNA sequence reads) | shRNA ID | Mouse (HUMAN) gene name | No of reads |
|---|---|---|---|---|---|
| | | 10-4 (89 reads) | HP_76455 | Xpo4 (XPO4) | 78 |
| | | | HP_268588 | Ddx20 (DDX20) | 10 |
| | | 10-5 (85 reads) | HP_76455 | Xpo4 (XPO4) | 72 |
| | | | HP_268588 | Ddx20 (DDX20) | 12 |
| | | 10-6 (89 reads) | HP_76455 | Xpo4 (XPO4) | 48 |
| | | | HP_265589 | Btbd9 (BTBD9) | 23 |
| | | | HP_268588 | Ddx20 (DDX20) | 9 |
| | | 10-7 (86 reads) | HP_76455 | Xpo4 (XPO4) | 50 |
| | | | HP_270196 | Set (SET) | 29 |
| | | | HP_268588 | Ddx20 (DDX20) | 7 |
| 11 | | 11-1 (69 reads) | HP_284899 | Sh2d3c (SH2D3C) | 19 |
| | | | HP_278543 | Glo1 (GLO1) | 14 |
| | | | HP_268149 | Cc2d1a (CC2D1A) | 11 |
| | | | HP_345044 | Fstl5 (FSTL5) | 10 |
| | | 11-2 (62 reads) | HP_309846 | 6530418L21Rik (C1orf183) | 15 |
| | | | HP_278543 | Glo1 (GLO1) | 13 |
| | | | HP_345044 | Fstl5 (FSTL5) | 7 |
| | | | HP_278031 | Maob (MAOB) | 6 |
| | | 11-3 (70 reads) | HP_278543 | Glo1 (GLO1) | 29 |
| | | | HP_345044 | Fstl5 (FSTL5) | 28 |
| 12 | | 12-1 (69 reads) | HP_420314 | Pde3b (PDE3B) | 13 |
| | | | HP_353921 | Set (SET) | 12 |
| | | | HP_353122 | Qtrtd1 (QTRTD1) | 11 |
| | | | HP_271204 | Bmp2k (BMP2K) | 6 |
| | | 12-1 (59 reads) | HP_322570 | 1810063B07Rik (C6orf64) | 21 |
| | | | HP_420314 | Pde3b (PDE3B) | 17 |
| | | | HP_485412 | Gm276 (FAM81B) | 11 |
| | | | HP_353921 | Set (SET) | 10 |
| | | 12-3 (77 reads) | HP_238455 | Gjd4 (GJD4) | 20 |
| | | | HP_477682 | Cryz (CRYZ) | 13 |
| | | | HP_420314 | Pde3b (PDE3B) | 11 |
| | | | HP_322570 | 1810063B07Rik (C6orf64) | 10 |
| | | | HP_485412 | Gm276 (FAM81B) | 7 |
| | | | HP_353921 | Set (SET) | 6 |
| | | 12-4 (65 reads) | HP_492873 | Fstl5 (FSTL5) | 20 |
| | | | HP_410182 | Mcart1 (MCART1) | 17 |
| | | | HP_483780 | Erich1 (ERICH1) | 10 |
| | | 12-5 (60 reads) | HP_282953 | BC050789 (FLJ23049) | 31 |
| | | | HP_238455 | Gjd4 (GJD4) | 26 |
| | | 12-6 (66 reads) | HP_282953 | BC050789 (FLJ23049) | 39 |
| | | | HP_238455 | Gjd4 (GJD4) | 26 |

We next sought to determine which candidates should be followed up in functional validation experiments. We decided to nominate candidates based on two criteria: i) overall enrichment of an shRNA in tumors triggered by a particular shRNA pool (high enrichment coefficient) and ii) detection of more than one scoring shRNA against a target. Based on these criteria a total of 17 shRNAs went into functional validation experiments using the same setup as used for the conduction of the initial screen (including a shRNA targeting the PTEN tumor suppressor, which already had been validated before).

Figure 17A:
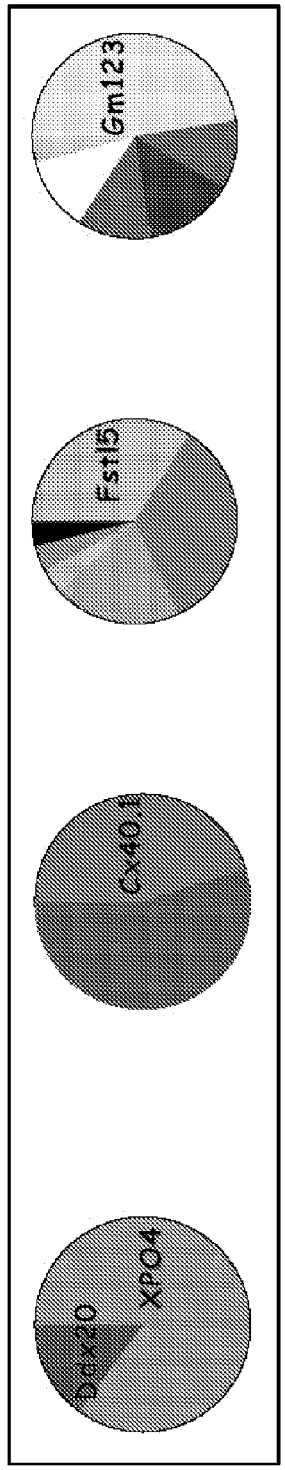
Figure 17B:
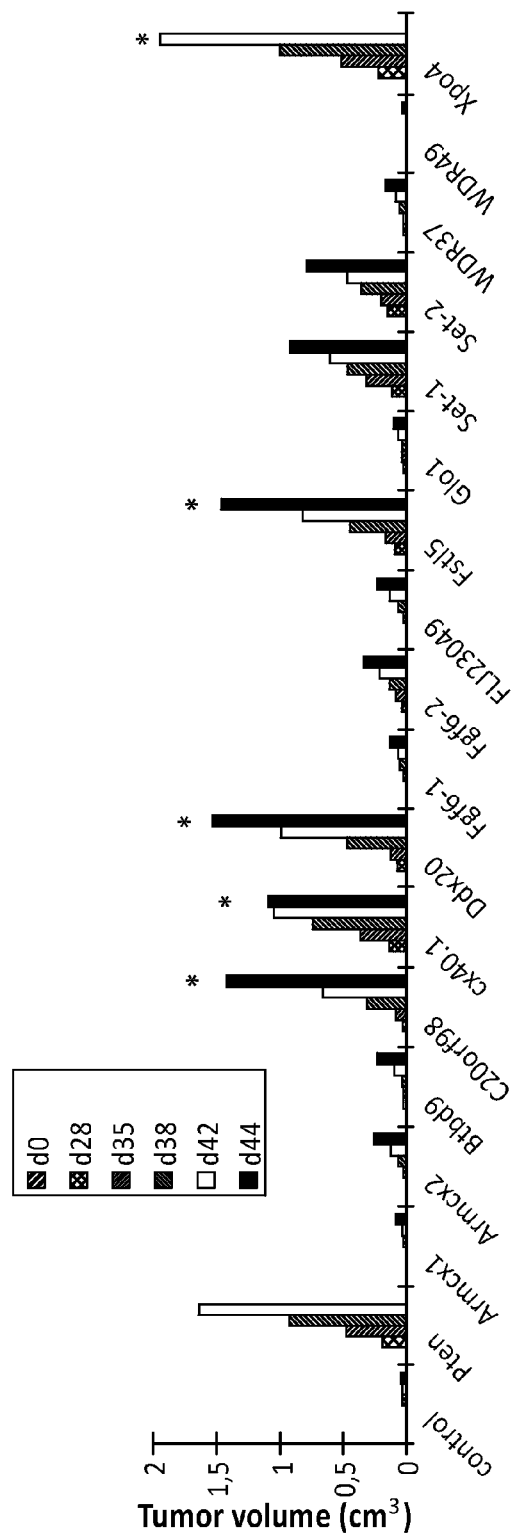
Figure 17D:
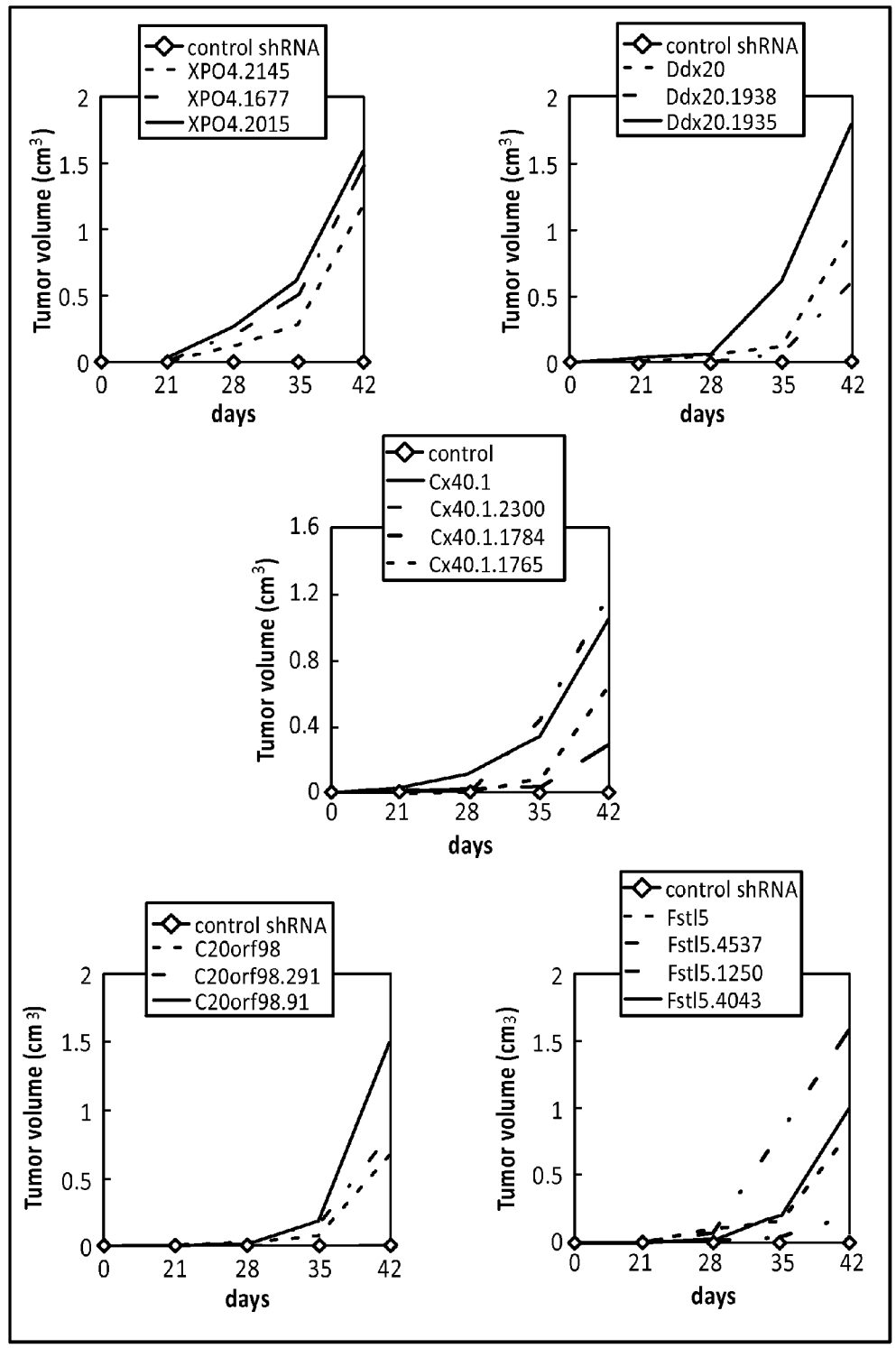

As shown in FIG. 17b, in addition to the PTEN shRNA, five other candidate shRNAs were capable of accelerating tumor growth of subcutaneous liver carcinomas (C20orf98, Cx40.1, Ddx20, Fstl5 and Xpo4). Interestingly, the top scoring candidate Xpo4 showed the most rapid acceleration of tumor growth. FIG. 17C reveals the focal genomic deletions in human HCCs (high resolution ROMA profiles) which are embedding the identified candidate genes. Of note, several of the 17 tested shRNAs showed acceleration of tumor growth above background, albeit less pronounced than the top scoring genes.

Figure 17E:
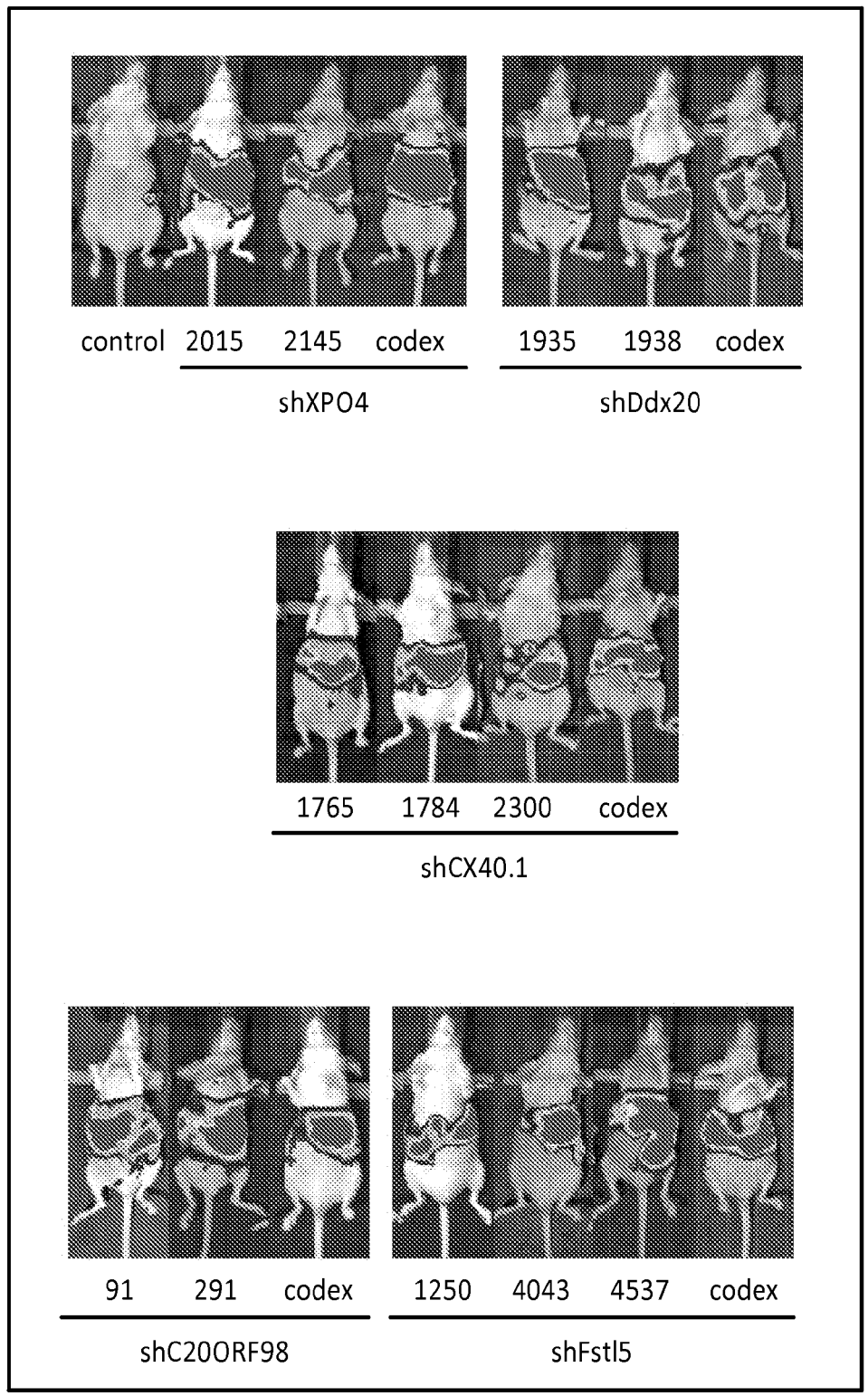

Using the biopred webtool we next generated de novo additional shRNAs targeting our top scoring candidate genes. In addition to our scoring shRNAs libraries, the RNAi Codex library, we generated at least two additional shRNAs (FIG. 17, D and E). These shRNAs were infected into p53−/−; myc liver progenitor cells side by side with the original Codex shRNAs and cell populations were either injected subcutaneously (FIG. 17D) or seeded into the livers of recipient mice by intrasplenic injection (FIG. 17E). Importantly, all shRNAs that were tested accelerated tumor growth with an efficiency similar or greater than the Codex shRNAs (FIG. 17, D, E).

Functional Characterization of Xpo4

We next aimed to gain mechanistic insight how loss of Xpo4, the top scoring candidate in our RNAi screen, promotes tumorigenesis. To date, two substrates for Xpo4 have been identified: Smad3, (give background) and eIF5A1 (see, FIG. 18A).

To address whether Xpo4 expression correlates with the amount of nuclear total and phospho-Smad3, we used murine hepatoma cells (p53−/−; myc) which were either infected with a control hairpin (shRNAmir luciferase) or two different hairpins targeting Xpo4. As shown by western blot in FIG. 18C, knockdown of Xpo4 with both shRNAmir leads to increased nuclear levels for total smad 3 and the transcriptionally active phosphor-Smad3. Results from western blot were confirmed by immunofluorescence (data not shown).

We next analyzed whether there is a correlation between Xpo4 status and Smad3 localization in human hepatoma cells. SK-Hep-1 human hepatoma cells harbor a homozygous deletion of Xpo4 (data not shown). Accordingly, we could not detect Xpo4 mRNA levels in SK-Hep-1 cells, while significant levels of Xpo4 mRNA could be detected by RT-Q-PCR in Huh7 and Alexander human hepatoma cells which display wild type status for the Xpo4 gene. While Huh7 and Alex hepatoma cells show a prominent cytoplasmic staining and no staining for Smad3 in the nucleus when analyzed by immunofluorescence, SK-Hep1 cells display a homogenous distribution of Smad3 protein in cytoplasm and nucleus.

TGF-beta signaling has been shown to be a double edged sword in tumorigenesis. Stimulation of TGF-beta receptor results in nuclear accumulation of Smad3 which, together with other transcription factor leads to the trans-activation of TGF-beta target genes.

To test whether increased nuclear levels of Smad3/p-Smad3 indeed lead to increased transcription of TGF-beta target genes, we performed RT-Q-PCR analysis for classical TGF-beta/Smad target genes. We observed that RNAi mediated reduction of Xpo4 gene expression results in increased mRNA levels for the pivotal TGF-beta target genes Jun, JunB, Mmp14, Co17A1, Timp1 and p15 (data not shown). As it is well established that increased TGF-beta signaling increases tumor progression, invasion and metastasis in later stager of tumor development, our results suggest that, at least in part, reduction of Xpo4 expression is pro-tumorigenic by inducing TGF-beta target genes.

In addition to Smad3, it has been shown that elongation initiation factor 5A1 (eIF5A1) is a substrate for Xpo4. To confirm nuclear export of eIF5A1 by Xpo4 in hepatoma cells, we first performed immunofluorescence experiments against eIF5A1 in murine hepatoma cells with or without shRNAmir mediated knockdown of Xpo4. While cells infected with the control shRNA showed almost no nuclear staining of eIF5A1, upon RNAi mediated knockdown of Xpo4 we detected a strong nuclear enrichment of eIF5A1. Results could be confirmed by western blot using cytoplasmic and nuclear protein preparations.

In addition to eIF5A1, a second eIF5 isoform has been identified, designated eIF5A2. Under normal conditions expression of eIF5A isoforms is regulated in a tissue specific manner. Normal tissues usually shown eIFA1 expression but lack eIF5A2 expression. However, increased eIF5A2 expression has been found in various cancer types, making eIF5A2 a candidate oncogene.

Interestingly, among our 98 human analyzed human HCCs, we found a tumor which displayed a focal amplicon for eIF5A2, thus further supporting the idea of eIF5A2 as a candidate oncogene downstream of Xpo4. We investigated whether loss of Xpo4 would affect cellular localization of eIF5A2. While the commercially available antibodies did not allow to analyze cellular localization of eIF5A2 by immunofluorescence, using immunoblot analysis on nuclear and cytoplasmic extracts, we found that Xpo4 knockdown leads to a moderate but significant nuclear retention of eIF5A2.

Although not wishing to be bound by particular theories, we believe a possible explanation to link the mislocalization of eIF5A1/2 with tumorigenesis is that, mislocalization of eIF5A1 and A2 via a feedback loop leads to a compensatory increase of A1 and A2, the second of which promotes tumorigenesis. In accordance with this model, we found a strong upregulation of eIF5A1 and eIF5A2 mRNA levels in murine and human hepatoma cell upon Xpo4 knockdown (data not shown). Interestingly, increased transcript levels only resulted in higher protein levels in the case eIF5A2 but not A1 (data not shown).

Figure 18H:
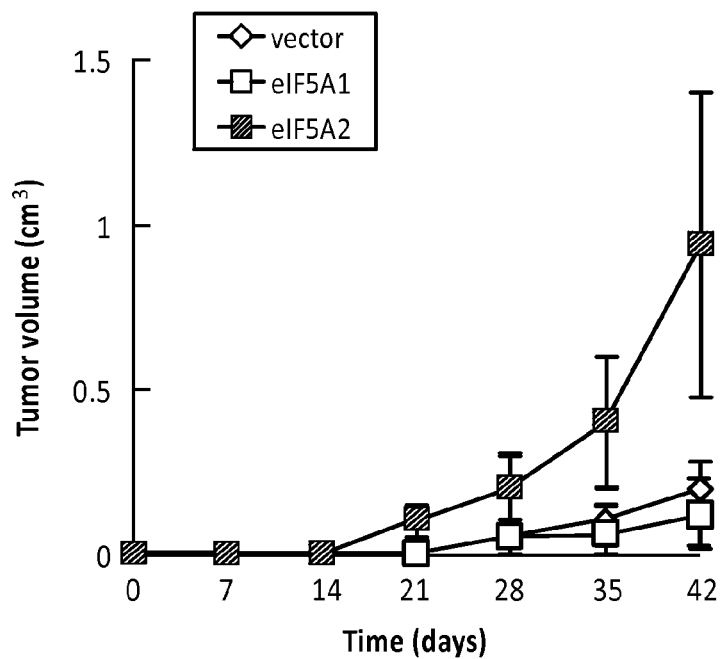

Our data suggest that loss of Xpo4 increases hepatocarcinigenesis by upregulation of eIF5A2 expression. To address whether increased expression of eIF5A1 or A2 can increase hepatocarcinogenesis in vivo, we infected p53–/–; myc liver progenitor cells with retroviruses encoding eIF5A1 or eIF5A2. As shown in FIG. 18h, we found that enforced overexpression of eIF5A2 but not A1 increases tumorigenesis of p53–/–; myc liver progenitor cells. Thus we confirmed eIF5A2 as an oncogene in hepatocarcinogenesis.

Those skilled in the art will recognize, or be able to ascertain using no more than routine experimentation, many equivalents to the specific embodiments of the invention described herein. Such equivalents are intended to be encompassed by the following embodiments.

What is claimed is:

1. A method for determining the status of a tumor suppressor gene in a subject suspected of having liver cancer, the method comprising:
   measuring the expression level of at least one tumor-suppressor gene by using an antibody against a tumor suppressor protein selected from the group consisting of XPO4, FGF6, WDR49, and PTEN to measure the level of the tumor suppressor protein in a biological sample from the subject,
   wherein a decrease in the expression level of the tumor-suppressor gene as compared to a control indicates that the subject is susceptible to liver cancer.

2. The method of claim 1, wherein the tumor-suppressor gene is XPO4.

3. The method of claim 1, further comprising measuring the expression level of at least two tumor-suppressor genes listed in Table 1.

4. A method for determining whether a subject is susceptible to developing liver cancer, the method comprising:
   (a) obtaining a biological sample from a subject,
   (b) measuring the level of expression of a tumor suppressor gene selected from the group consisting of XPO4, FGF6, WDR49, and PTEN in the biological sample, and
   (c) comparing the level of expression of the tumor suppressor gene in the biological sample from the subject to the level of expression of the tumor suppressor gene in a control sample,
   wherein a level of expression of the tumor suppressor gene in the biological sample from the subject that is lower than the level of expression of the tumor suppressor gene in the control sample indicates that the subject is susceptible to developing liver cancer.

5. The method of claim 4, wherein the tumor-suppressor gene is XPO4.

6. The method of claim 4, further comprising measuring the expression level of at least two tumor-suppressor genes listed in Table 1.

7. The method of claim 4 wherein the measuring step comprises measuring the level of a tumor suppressor protein selected from the group consisting of the XPO4, FGF6, WDR49, and PTEN tumor suppressor proteins.

8. The method of claim 4, wherein the measuring step comprises contacting the biological sample with an antibody that binds to the tumor suppressor protein.

9. The method of claim 4, wherein the measuring step comprises performing an assay selected from the group consisting of an enzyme linked immunosorbent assay (ELISA), performing a radioimmunoassay (RIA), immunoblotting, an immunohistochemical assay, immunoprecipitation, wherein the assay uses an antibody that binds to the tumor suppressor protein.

10. The method of claim 4, wherein the measuring step comprises performing 2-D gel electrohporesis.

11. The method of claim 4, wherein the measuring step comprises performing mass spectrometry.

12. The method of claim 4, wherein the measuring step comprises measuring the level of an mRNA selected from the group consisting of a XPO4, FGF6, WDR49, and PTEN mRNA.

13. The method of claim 12, wherein the measuring step comprises performing a polymerase chain reaction (PCR) method.

14. The method of claim 12, wherein the measuring step comprises performing a quantitative real time PCR (QRT-PCR) method.

15. The method of claim 4, wherein the control sample is biological sample from a healthy individual.

16. The method of claim 4, wherein the control sample is a biological sample from an individual without liver cancer.

17. The method of claim 4, wherein the control sample is a non-cancerous tissue sample.

18. A method for determining the level of expression of a tumor suppressor gene in a subject suspected of having liver cancer, the method comprising:
(a) obtaining a biological sample from a subject suspected of having liver cancer, and
(b) determining the level of expression of a tumor suppressor gene selected from the group consisting of XPO4, FGF6, WDR49, and PTEN in the biological sample.

* * * * *